(12) United States Patent
Kabbash et al.

(10) Patent No.: US 6,531,291 B1
(45) Date of Patent: Mar. 11, 2003

(54) ANTIMICROBIAL ACTIVITY OF GEMFIBROZIL AND RELATED COMPOUNDS AND DERIVATIVES AND METABOLITES THEREOF

(75) Inventors: Christina Kabbash, Greenwich, CT (US); Samuel C. Silverstein, New York, NY (US); Howard A. Shuman, Larchmont, NY (US); John S. Blanchard, Larchmont, NY (US)

(73) Assignees: The Trustees of Columbia University in the City of New York, New York, NY (US); Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/438,144

(22) Filed: Nov. 10, 1999

(51) Int. Cl.[7] .............................. C12N 9/02; C12Q 1/26
(52) U.S. Cl. ......................... 435/25; 435/189
(58) Field of Search .................... 435/25, 189

(56) References Cited

U.S. PATENT DOCUMENTS

| 4,859,703 A | 8/1989 | Krause ................... 514/543 |
| 4,891,220 A | 1/1990 | Donzis ................... 514/356 |
| 5,422,372 A | 6/1995 | Silverstein et al. ......... 514/571 |
| 5,837,480 A | * 11/1998 | Sacchettini et al. ........... 435/25 |

FOREIGN PATENT DOCUMENTS

| WO | 97/31530 | * 9/1997 |
| WO | 99/37800 | * 7/1999 |

OTHER PUBLICATIONS

Bergler et al. The enoyl–[acyl carrier protein] reductase . . . Eur. J. Biochem. vol. 242, pp. 689–694, 1996.*
Cardon et al. Kinetic and Structural Investigation of Acyl . . . J. Biol. Chem. vol. 258, No. 8, pp. 4802–4807, Apr. 25, 1983.*
Clements et al. Irreversible inhibition of fatty acid synthase . . . Biochem. J. vol. 207, pp. 291–296, 1982.*
Heath et al. Regulation of Fatty Acid Elongation and Initiation . . . J. Biol. Chem. vol. 271, No. 4, pp. 1833–1836, Jan. 26, 1996.*
Vernon et al. The Presence of Essential Arginine Residues . . . Biochim. et Biophys. Acta. vol. 788, pp. 124–131, 1989.*
The Merck Index, 10th ed., Merck & Co., Inc., Rathway, N.J., 1983, #4246.

* cited by examiner

Primary Examiner—Jeffrey E. Russel
(74) Attorney, Agent, or Firm—John P. White; Cooper & Dunham LLP

(57) ABSTRACT

The present invention provides a method of selecting a compound which inhibits the enzymatic activity of enoyl reductase which comprises: (A) contacting enoyl reductase with the compound linked to an acyl carrier protein; (B) measuring the enzymatic activity of the entoy reductase of step (A) compared with the enzymatic activity of enoyl reductase in the absence of the compound and selecting the compound which inhibits the enzymatic activity of enoyl reductase.

7 Claims, 57 Drawing Sheets

FIG. 1

| *E. coli* | *L. pneumophila* |
|---|---|
| 16:0 | i-16:0 |
| 16:1$^9$ | a-15:0 |
| 18:0 | 16:1$^9$ |
| 18:1$^{11}$ | a17:0 |
| | 3-OH-12:0 |
| 14:0 (LPS) | 16:0 |
| 3-OH-14:0 (LPS) | i-16:1$^9$ |
| | 20:0 |
| | Δ17:0 |
| | 18:0 |
| | 17:0 |
| | 15:0 |
| | 19:0 |
| | 14:0 |
| | 18:1$^9$ |
| | |
| | 3-OH-14:0 (LPS) |
| | 3-OH i-14:0 (LPS) |
| | 3-OH-18:0 (LPS) |
| | 3-OH-i-18:0 (LPS) |
| | 3-OH-19:0 (LPS) |
| | 3-OH-20:0 (LPS) |
| | 3-OH-i-20:0 (LPS) |
| | 3-OH-21:0 (LPS) |
| | 3-OH-i-22:0 (LPS) |
| | 2,3-diOH-14:0 (LPS) |
| | 2,3 di-OH-i-14:0 (LPS) |
| | (27-oxo)28:0 (LPS) |
| | 27:0-dioic (LPS) |

Fatty Acid Synthesis Pathway in *E. coli*

Hours after HL-60 infection
with *L. pneumophila*

FIG. 7
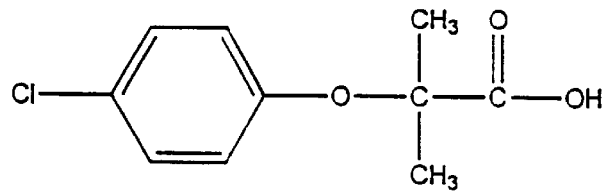
CFA
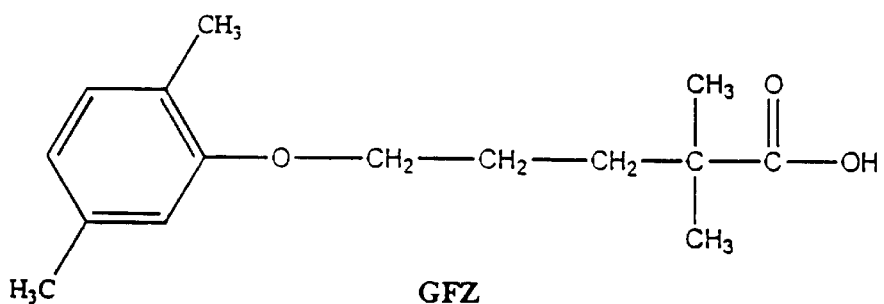
GFZ
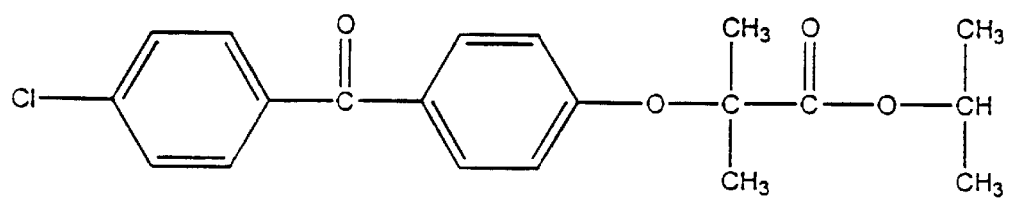
FNF
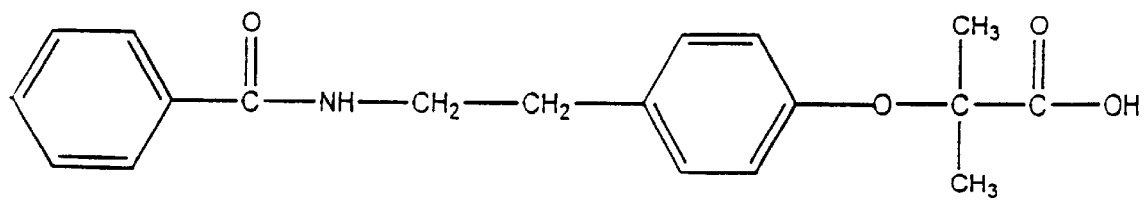
BZF

FIGURE 8

Susceptibility to GFZ as Measured by a Zone of Inhibition Assay

Zone of Inhibiton Present

Bacillus subtilis  (1/1)
Bacillus aureus  (1/1)
Candida albicans  (1/1)
Caulobacter crescentus  (1/1)
Group A Streptococcus sp.  (1/6)
Legionella pneumophila  (39/39)
Mycobacterium intracellulare  (1/2)
Mycobacterium tuberculosis  (27/27)
Nocardia sp.  (12/12)
Rhodobacter spheroides  (1/1)
Saccharomyces cerevisiae  (2/2)
Staphylococcus aureus  (4/4)
Staphylococcus epidermis  (1/1)

No Zone of Inhibition

Acinetobacter sp.  (2/2)
Actinobacillus sp.  (1/1)
Azobacter vinlandi  (1/1)
Cardiobacterium sp.  (1/1)
Citrobacter freundi  (1/1)
Corynebacterium sp.  (4/4)
Enterobacter cloacae  (2/2)
Enterococcus faecalis  (4/4)
Escherichia coli  (4/4)
Group A Streptococcus sp.  (5/6)
Klebsiella pneumoniae  (3/3)
Leuconostoc sp.  (2/2)
Mycobacterium chelonei  (2/2)
Mycobacterium fortuitum  (3/3)
Pediococcus sp.  (1/1)
Proteus mirabilis  (2/2)
Pseudomonas aeruginosa  (7/7)
Rhizobium nulilo  (1/1)
Rhodococcus sp.  (3/3)
Salmonella sp  (2/2)
Serratia marcescens  (2/2)
Shigella sp.  (1/1)
Xanthomonas sp.  (1/1)

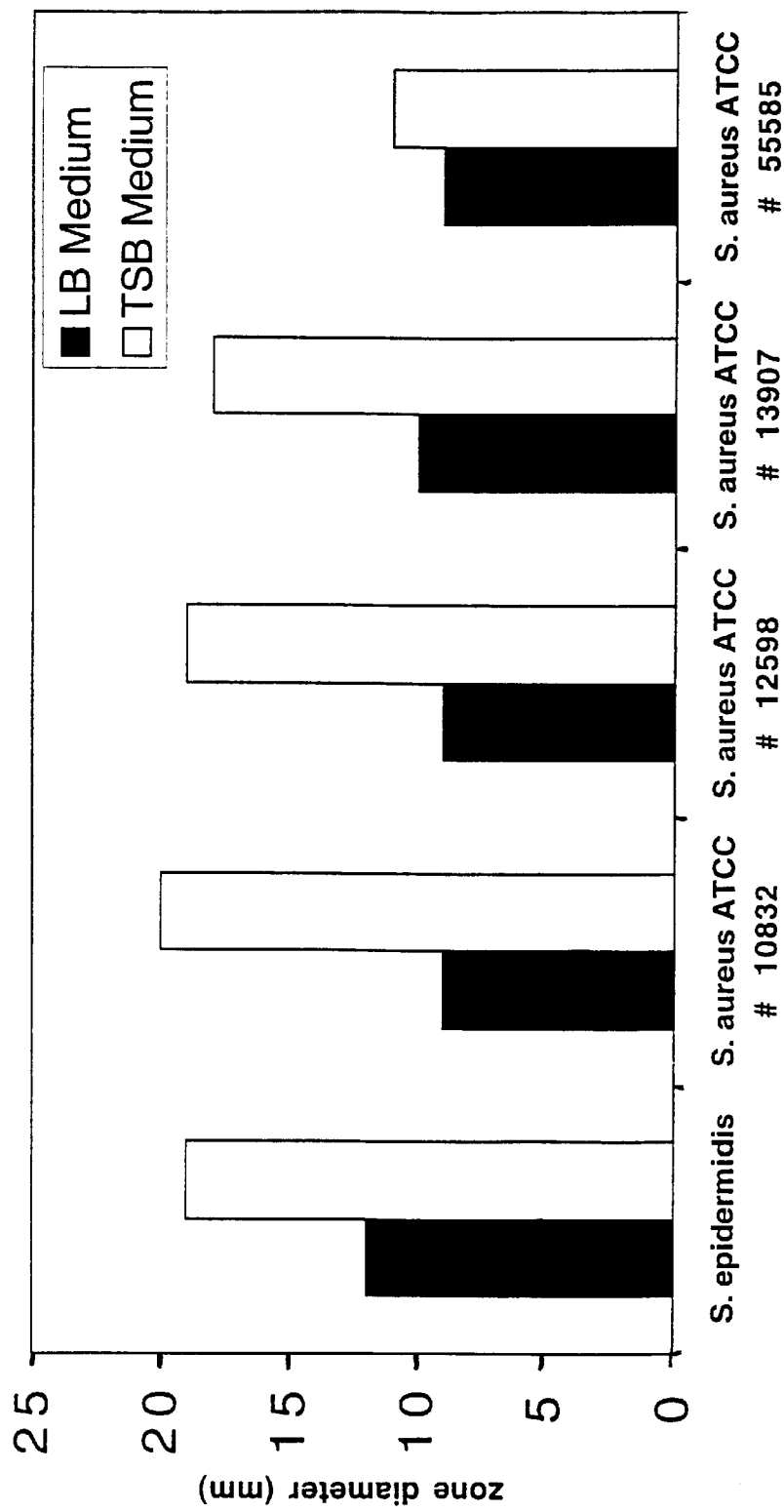

FIG. 10

Inhibition of *M. tuberculosis* Strains by GFZ

| Drug Resistance Profiles‡ S | I | R | E | K | O | C | Strain | GFZ 0 μg/ml | GFZ 100 μg/ml | GFZ 200 μg/ml |
|---|---|---|---|---|---|---|---|---|---|---|
| S | R | R | S | S | S | S | JJ | +++ | 0 | 0 |
| S | R | S | S | S | S | S | NM | ++++ | 0 | 0 |
| R | R | R | R | S | S | S | W54410 | ++ | 0 | 0 |
| S | R | R | S | S | S | S | F5260 | ++ | 0 | 0 |
| S | R | R | R | S | S | S | T30234 | ++ | 0 | 0 |
| R | R | R | R | S | S | S | O81256 | ++ | 0 | 0 |
| S | R | R | R | S | S | S | W19521 | ++ | 0 | 0 |
| S | S | S | S | S | S | S | O80154 | +++ | 0 | 0 |
| S | S | R | S | S | S | S | CDCN | ++ | 0 | 0 |
| R | S | S | S | S | S | S | H52578 | ++ | 0 | 0 |
| R | R | R | R | S | S | S | RF | ++++ | 0 | 0 |
| S | $R^L$ | S | S | S | S | S | CDCP | +++ | 0 | 0 |
| S | $R^L$ | S | S | S | S | S | CDCT | +++ | 0 | 0 |
| S | $R^L$ | S | S | S | S | S | CDCD | +++ | 0 | 0 |
| S | S | S | S | S | S | S | H37RV | +++ | 1 | 0 |
| R | R | R | S | S | S | S | O80711 | ++ | 6 | 0 |
| S | R | S | S | S | S | ND | S15674 | ++ | 10 | 0 |
| S | S | S | R | S | S | S | M23294 | ++ | 4.5 | 0 |
| S | S | S | S | S | S | S | CDCK | +++ | 6 | 0 |
| S | S | S | R | S | S | S | M41151 | ++ | 7.5 | 0 |
| S | R | S | S | S | S | S | F16285 | ++ | 10 | 0 |
| R | R | R | R | R | R | R | T45777 | +++ | + | 0 |
| R | R | R | R | R | R | R | AA | +++ | + | 0 |
| S | S | S | S | S | S | S | MH | +++ | + | 0 |
| R | S | R | S | S | S | S | CDCL | +++ | ++ | 0 |
| R | S | S | S | S | S | S | CM | ++++ | ++ | 0 |
| S | S | S | S | S | S | S | MTB25177 | ++++ | ++ | 0 |

Symbols: 0 = no growth; numbers = average number of colonies in duplicate quadrants with < 50 colonies; + = 50-100 colonies/quadrant; ++ = 100-500 colonies/quadrant; +++ = 200-500 colonies/quadrant; ++++ = confluent growth ‡ Sensitivity (S) or resistance (R) to antibiotics: S= streptomycin 2 mg/ml; I= isoniazid 1 mg/ml; R= rifampin 1 mg/ml; E= ethambutol 5 mg/ml; K= kanamycin 6 mg/ml; O= ofloxacin 4 mg/ml; C= ciprofloxacin 2 mg/ml; $R^L$ = low level resistance to isoniazid at 0.2 mg/ml; ND = not done

FIG. 11

| Strain | GFZ 0 µg/ml | GFZ 50 µg/ml | GFZ 300 µg/ml |
|---|---|---|---|
| NM | ++ | + | - |
| RF | + | - | - |
| JJ | ++ | + | - |
| CDC T | ++ | + | - |
| H37RV | ++ | + | - |

Symbols: ++ = thick growth; + = sparse growth; - = no growth

FIG. 13
SAL 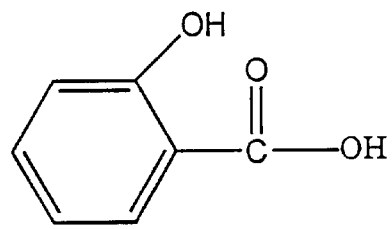
4-HPA 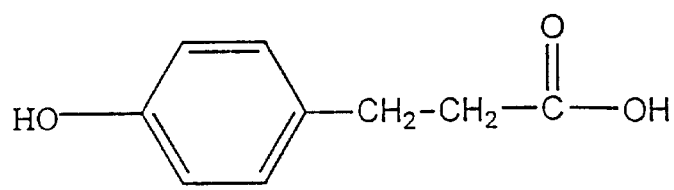
3,4-HPA 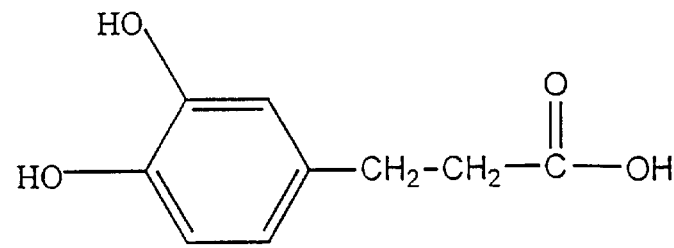
GFZ 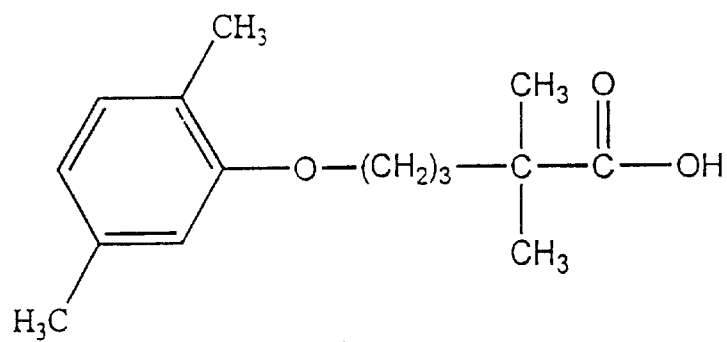

FIG. 15A  
FIG. 15B  
FIG. 15C  
FIG. 15D
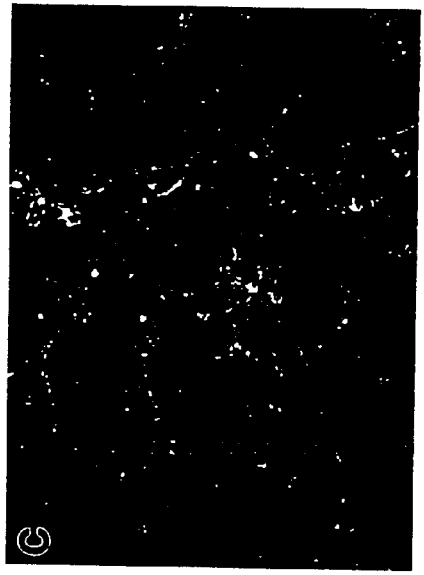
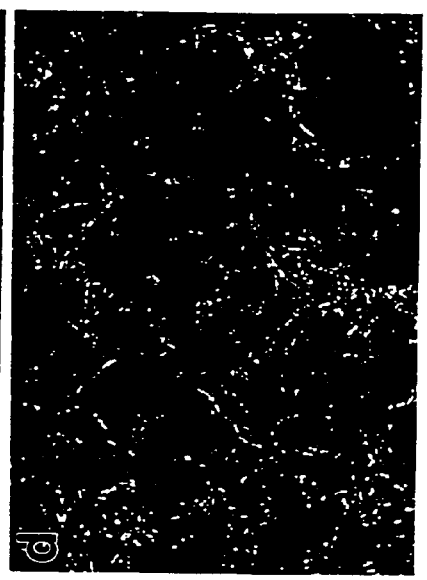

FIG. 16

Effect of GFZ on 3-HB Content
in *L. pneumophila*

| agar medium | mg of 3-HB (+/- SEM) per 40 mg of lyophilized *L. pneumophila* |
|---|---|
| CYE | 0.03 (+/- 0.03) |
| CYE + GFZ | 1.7 (+/- 0.30) |

FIGURE 17        Fatty Acid Synthesis Pathway

Model for PHB Accumulation in *L. pneumophila*

Fatty Acid Synthesis Pathway

FIG. 30

```
L.pneumophila     MGGDTIVGFLTGKKALIVGLASNRSIAYGIAKAFHNQGAELAFTYQNEKLQSRVETMASE
E.coli            ------MGFLSGKRILVTGVASKLSIAYGIAQAMHREGAELAFTYQNDKLKGRVEEFAAQ
S.typhimurium     ------MGFLSGKRILVTGVASKLSIAYGIAQAMHREGAELAFTYQNDKLKGRVEEFAAQ
H.influenza       ------MGFLTGKRILVTGLASNRSIAYGIAKSMKEQGAELAFTYLNDKLQPRVEEFAKE
M.tuberculosis    -----MTGLLDGKRILVSGIITDSSIAFHIARVAQEQGAQLVLTG-FDRLRLIQRITDRL
                               *   * * *     *   *   * *  *      ** *

L.pneumophila     FNSTLVFPCDVASD---EEIKAVFDNLRNHWDKLDILVHSVAYAPADQISGDFVECANRE
E.coli            LGSDIVLQCDVAED---ASIDTMFAELGKVWPKFDGFVHSIGFAPGDQLDGDYVNAVTRE
S.typhimurium     LGSSIVLPCDVAED---ASIDAMFAELGNVWPKFDGFVHSIGFAPGDQLDGDYVNAVTRE
H.influenza       FGSDIVLPLDVATD---ESIQNCFAELSKRWDKFDGFIHAIAFAPGDQLDGDYVNAATRE
M.tuberculosis    PAKAPLLELDVQNEEHLASLAGRVTEAIGAGNKLDGVVHSIGFMPQTGMGINPFFDAPYA
                       *       *     *                 * ** *     *

L.pneumophila     GFRIAHDISAYSLIGLSQAALPMMLDTQGSILTLSYYGAEKAVPNYNVMGVAKASLEASV
E.coli            GFKIAHDISSYSFVAMAKACR-SMLNPGSALLTLSYLGAERAIPNYNVMGLAKASLEANV
S.typhimurium     GFKVAHDISSYSFVAMAKACR-TMLNPGSALLTLSYLGAERAIPNYNVMGLAKASLEANV
H.influenza       GYRIAHDISAYSFVAMAQAAR-PYLNPNAALLTLSYLGAERAIPNYNVMCLAKASLEAAT
M.tuberculosis    DVSKGIHISAYSYASMAKALLPIMN-PGGSIVGMDFD-PSRAMPAYNWMTVAKSALESVN
                           *     ***           *** * *    * *       *  **  *

L.pneumophila     RYLAASLGSRGLRINAISAGPIKTLAAAGIKDFRKIHAAYANITPLQR-----------N
E.coli            RYMANAMGPEGVRVNAISAGPIRTLAASGIKDFRKMLAHCEAVTPIRR-----------T
S.typhimurium     RYMANAMGPEGVRVNAISAGPIRTLAASGIKDFRKMLAHCEAVTPIRR-----------T
H.influenza       RVMAADLGKEGIRVNAISAGPIRTLAASGIKNFKKMLSTFEKTAALRR-----------T
M.tuberculosis    RFVAREAGKYGVRSNLVAAGPIRTLAMSAIVGGALGEEAGAQIQLLEEGWDQRAPIGWNM
                    *         *   **    *    *                  *
```

FIG. 33

**Alignment of the two *L. pneumophila* enoyl reductase proteins**

```
Fab T    1 .........MKNKKGLIIGIANEHSIAWGCAKVLYEANCELAITYQNEKA 41

Fab X    1 MGGDTIVGFLTGKKALIVGLASNRSIAYGIAKAFHNQGAELAFTYQNEKL 50

42 KSYVQSLAEQVSASIFMPLDVTDKAQFDALFQRIKESWSHLDFVIHAIAF 91

51 QSRVETMASEFNSTLVFPCDVASDEEIKAVFDNLRNHWDKLDILVHSVAY 100

92 APKADLQGRVVDC.SKEGFMVAMDVSCHSLIRLAKAAEPLMVN.GGSIMT 139

101 APADQISGDFVECANREGFRIAHDISAYSLIGLSQAALPMMLDTQGSILT 150

140 MSYYGAEKVVKNYNLMGPVKAALETSVRYLAMELGSKKIRVNAISPGPIS 189

151 LSYYGAEKAVPNYNVMGVAKASLEASVRYLAASLGSRGLRINAISAGPIK 200

190 TRAASGLADFDKLMEKAANEAPLHQLVTIEAIGEMAAFLVSDKAVSITGQ 239

201 TLAAAGIKDFRKIHAAYANITPLQRNVTADEVGNTAAFLCSDLASGITGE 250

240 ILYVDAGYNIKG...... 251

251 VLHVDAGYHAVSAMSELG 268
```

Percent Similarity: 61.753   Percent Identity: 48.207

FIG. 36
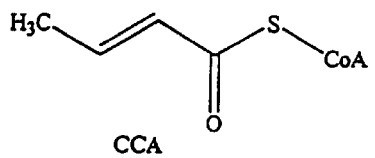
CCA
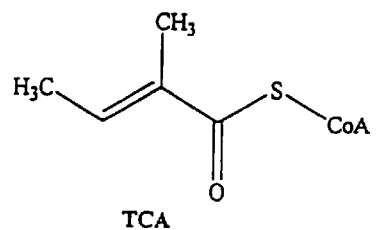
TCA
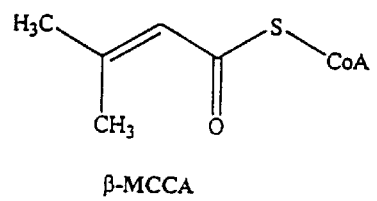
β-MCCA
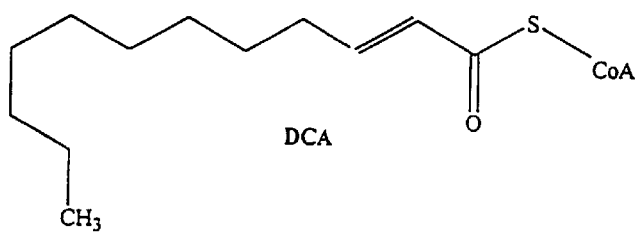
DCA
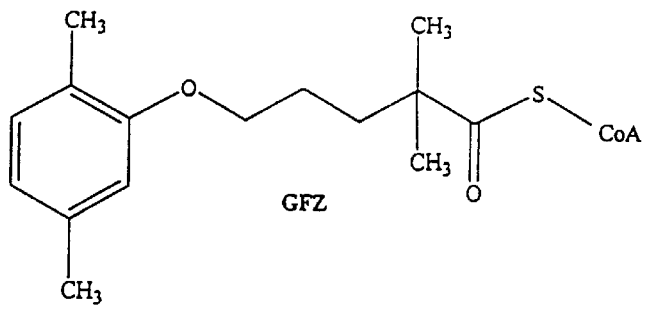
GFZ
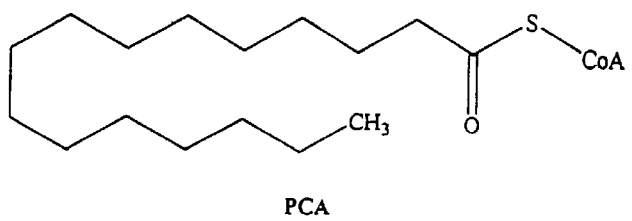
PCA 1/[DCA]  mM

*In vivo* $^3$H-GFZ Labeling of *L. pneumophila*

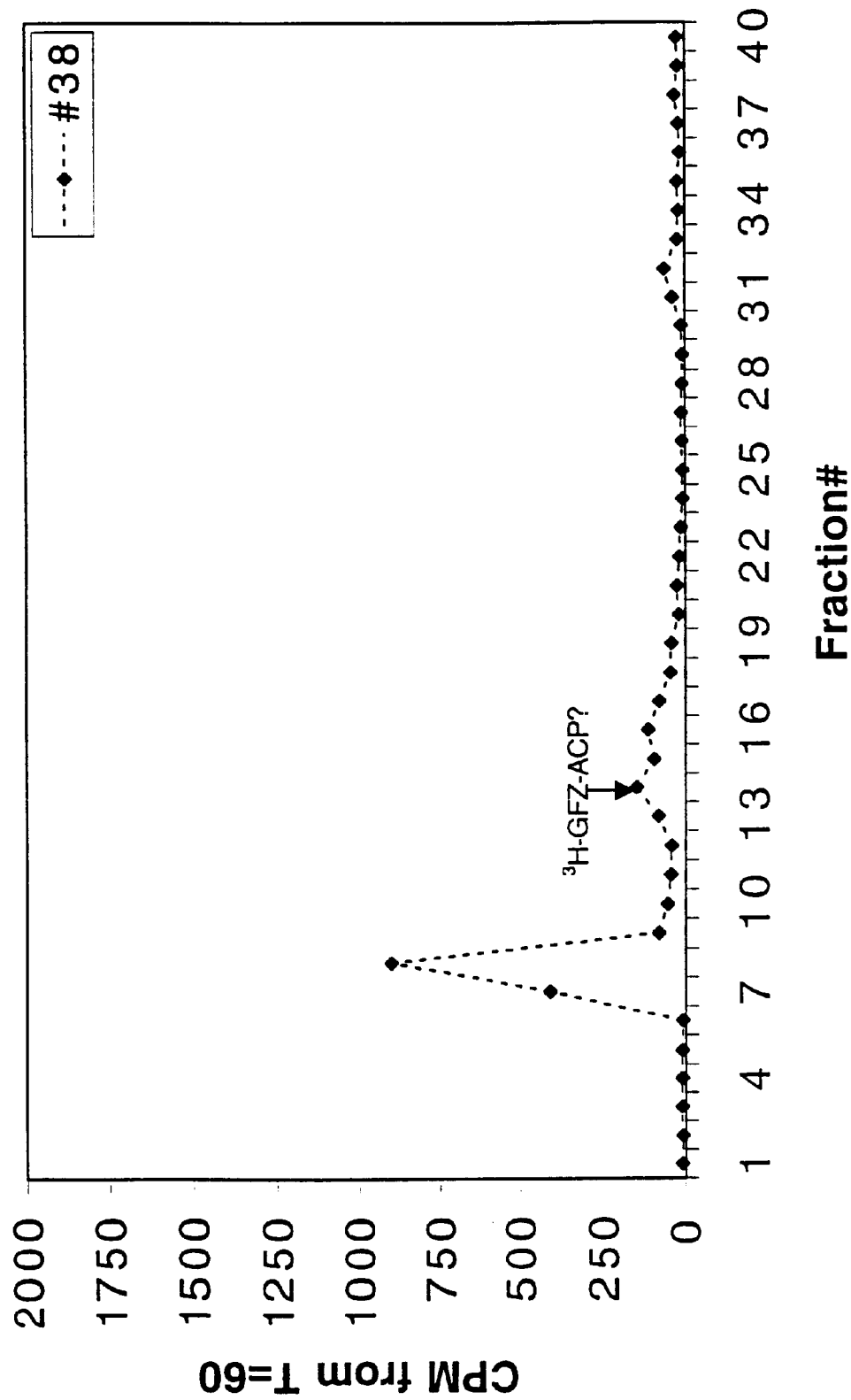

SEQUENCE LISTING

<160> NUMBER OF SEQ ID NOS: 7

<210> SEQ ID NO 1
<211> LENGTH: 226
<212> TYPE: PRT
<213> ORGANISM: L. pneumophila

<400> SEQUENCE: 1

```
Met Gly Gly Asp Thr Ile Val Gly Phe Leu Thr Gly Lys Lys Ala Leu
1               5                   10                  15

Ile Val Gly Leu Ala Ser Asn Arg Ser Ile Ala Tyr Gly Ile Ala Lys
            20                  25                  30

Ala Phe His Asn Gln Gly Ala Glu Leu Ala Phe Thr Tyr Gln Asn Glu
        35                  40                  45

Lys Leu Gln Ser Arg Val Glu Thr Met Ala Ser Glu Phe Asn Ser Thr
    50                  55                  60

Leu Val Phe Pro Cys Asp Val Ala Ser Asp Glu Glu Ile Lys Ala Val
65                  70                  75                  80

Phe Asp Asn Leu Arg Asn His Trp Asp Lys Leu Asp Ile Leu Val His
                85                  90                  95

Ser Val Ala Tyr Ala Pro Ala Asp Gln Ile Ser Gly Asp Phe Val Glu
            100                 105                 110

Cys Ala Asn Arg Glu Gly Phe Arg Ile Ala His Asp Ile Ser Ala Tyr
        115                 120                 125

Ser Leu Ile Gly Leu Ser Gln Ala Ala Leu Pro Met Met Leu Asp Thr
    130                 135                 140

Gln Gly Ser Ile Leu Thr Leu Ser Tyr Tyr Gly Ala Glu Lys Ala Val
145                 150                 155                 160

Pro Asn Tyr Asn Val Met Gly Val Ala Lys Ala Ser Leu Glu Ala Ser
                165                 170                 175

Val Arg Tyr Leu Ala Ala Ser Leu Gly Ser Arg Gly Leu Arg Ile Asn
            180                 185                 190

Ala Ile Ser Ala Gly Pro Ile Lys Thr Leu Ala Ala Ala Gly Ile Lys
        195                 200                 205

Asp Phe Arg Lys Ile His Ala Ala Tyr Ala Asn Ile Thr Pro Leu Gln
    210                 215                 220

Arg Asn
225
```

<210> SEQ ID NO 2
<211> LENGTH: 220
<212> TYPE: PRT
<213> ORGANISM: E. coli

<400> SEQUENCE: 2

```
Met Gly Phe Leu Ser Gly Lys Arg Ile Leu Val Thr Gly Val Ala Ser
1               5                   10                  15

Lys Leu Ser Ile Ala Tyr Gly Ile Ala Gln Ala Met His Arg Glu Gly
            20                  25                  30

Ala Glu Leu Ala Phe Thr Tyr Gln Asn Asp Lys Leu Lys Gly Arg Val
        35                  40                  45
```

-continued

```
Glu Glu Phe Ala Ala Gln Leu Gly Ser Asp Ile Val Leu Gln Cys Asp
    50                  55                  60

Val Ala Glu Asp Ala Ser Ile Asp Thr Met Phe Ala Glu Leu Gly Lys
 65                  70                  75                  80

Val Trp Pro Lys Phe Asp Gly Phe Val His Ser Ile Gly Phe Ala Pro
                 85                  90                  95

Gly Asp Gln Leu Asp Gly Asp Tyr Val Asn Ala Val Thr Arg Glu
                100                 105                 110

Gly Phe Lys Ile Ala His Asp Ile Ser Ser Tyr Ser Phe Val Ala Met
            115                 120                 125

Ala Lys Ala Cys Arg Ser Met Leu Asn Pro Gly Ser Ala Leu Leu Thr
130                 135                 140

Leu Ser Tyr Leu Gly Ala Glu Arg Ala Ile Pro Asn Tyr Asn Val Met
145                 150                 155                 160

Gly Leu Ala Lys Ala Ser Leu Glu Ala Asn Val Arg Tyr Met Ala Asn
                165                 170                 175

Ala Met Gly Pro Glu Gly Val Arg Val Asn Ala Ile Ser Ala Gly Pro
            180                 185                 190

Ile Arg Thr Leu Ala Ala Ser Gly Ile Lys Asp Phe Arg Lys Met Leu
            195                 200                 205

Ala His Cys Glu Ala Val Thr Pro Ile Arg Arg Thr
210                 215                 220

<210> SEQ ID NO 3
<211> LENGTH: 219
<212> TYPE: PRT
<213> ORGANISM: S. typhimurium

<400> SEQUENCE: 3

Met Gly Phe Leu Ser Gly Lys Arg Ile Leu Val Thr Gly Val Ala Ser
 1               5                  10                  15

Lys Leu Ser Ile Ala Tyr Gly Ile Ala Gln Ala Met His Arg Glu Gly
            20                  25                  30

Ala Glu Leu Ala Phe Thr Tyr Gln Asn Asp Lys Leu Lys Gly Arg Val
        35                  40                  45

Glu Glu Phe Ala Ala Gln Leu Gly Ser Ser Ile Val Leu Pro Cys Asp
    50                  55                  60

Val Ala Glu Asp Ala Ser Ile Asp Ala Met Phe Ala Glu Leu Gly Asn
 65                  70                  75                  80

Val Trp Pro Lys Phe Asp Gly Phe Val His Ser Ile Gly Phe Ala Pro
                 85                  90                  95

Gly Asp Gln Leu Asp Gly Asp Tyr Val Asn Ala Val Thr Arg Glu Gly
                100                 105                 110

Phe Lys Val Ala His Asp Ile Ser Ser Tyr Ser Phe Val Ala Met Ala
            115                 120                 125

Lys Ala Cys Arg Thr Met Leu Asn Pro Gly Ser Ala Leu Leu Thr Leu
130                 135                 140

Ser Tyr Leu Gly Ala Glu Arg Ala Ile Pro Asn Tyr Asn Val Met Gly
145                 150                 155                 160

Leu Ala Lys Ala Ser Leu Glu Ala Asn Val Arg Tyr Met Ala Asn Ala
                165                 170                 175

Met Gly Pro Glu Gly Val Arg Val Asn Ala Ile Ser Ala Gly Pro Ile
            180                 185                 190

Arg Thr Leu Ala Ala Ser Gly Ile Lys Asp Phe Arg Lys Met Leu Ala
```

-continued

```
                195                 200                 205
His Cys Glu Ala Val Thr Pro Ile Arg Arg Thr
    210                 215
```

<210> SEQ ID NO 4
<211> LENGTH: 219
<212> TYPE: PRT
<213> ORGANISM: H. influenza

<400> SEQUENCE: 4

```
Met Gly Phe Leu Thr Gly Lys Arg Ile Leu Val Thr Gly Leu Ala Ser
1               5                   10                  15

Asn Arg Ser Ile Ala Tyr Gly Ile Ala Lys Ser Met Lys Glu Gln Gly
            20                  25                  30

Ala Glu Leu Ala Phe Thr Tyr Leu Asn Asp Lys Leu Gln Pro Arg Val
        35                  40                  45

Glu Glu Phe Ala Lys Glu Phe Gly Ser Asp Ile Val Leu Pro Leu Asp
    50                  55                  60

Val Ala Thr Asp Glu Ser Ile Gln Asn Cys Arg Ala Glu Leu Ser Lys
65                  70                  75                  80

Arg Trp Asp Lys Phe Asp Gly Phe Ile His Ala Ile Ala Phe Ala Pro
                85                  90                  95

Gly Asp Gln Leu Asp Gly Asp Tyr Val Asn Ala Ala Thr Arg Glu Gly
            100                 105                 110

Tyr Arg Ile Ala His Asp Ile Ser Ala Tyr Ser Phe Val Ala Met Ala
        115                 120                 125

Gln Ala Ala Arg Pro Tyr Leu Asn Pro Asn Ala Ala Leu Leu Thr Leu
    130                 135                 140

Ser Tyr Leu Gly Ala Glu Arg Ala Ile Pro Asn Tyr Asn Val Met Cys
145                 150                 155                 160

Leu Ala Lys Ala Ser Leu Glu Ala Ala Thr Arg Val Met Ala Ala Asp
                165                 170                 175

Leu Gly Lys Glu Gly Ile Arg Val Asn Ala Ile Ser Ala Gly Pro Ile
            180                 185                 190

Arg Thr Leu Ala Ala Ser Gly Ile Lys Asn Phe Lys Lys Met Leu Ser
        195                 200                 205

Thr Phe Glu Lys Thr Ala Ala Leu Arg Arg Thr
    210                 215
```

<210> SEQ ID NO 5
<211> LENGTH: 232
<212> TYPE: PRT
<213> ORGANISM: M. tuburculosis

<400> SEQUENCE: 5

```
Met Thr Gly Leu Leu Asp Gly Lys Arg Ile Leu Val Ser Gly Ile Ile
1               5                   10                  15

Thr Asp Ser Ser Ile Ala Phe His Ile Ala Arg Val Ala Gln Glu Gln
            20                  25                  30

Gly Ala Gln Leu Val Leu Thr Gly Phe Asp Arg Leu Arg Leu Ile Gln
        35                  40                  45

Arg Ile Thr Asp Arg Leu Pro Ala Lys Ala Pro Leu Leu Glu Leu Asp
    50                  55                  60

Val Gln Asn Glu Glu His Leu Ala Ser Leu Ala Gly Arg Val Thr Glu
65                  70                  75                  80

Ala Ile Gly Ala Gly Asn Lys Leu Asp Gly Val Val His Ser Ile Gly
```

-continued

```
                85                  90                  95

Phe Met Pro Gln Thr Gly Met Gly Ile Asn Pro Phe Phe Asp Ala Pro
            100                 105                 110

Tyr Ala Asp Val Ser Lys Gly Ile His Ile Ser Ala Tyr Ser Tyr Ala
        115                 120                 125

Ser Met Ala Lys Ala Leu Leu Pro Ile Met Asn Pro Gly Gly Ser Ile
    130                 135                 140

Val Gly Met Asp Phe Asp Pro Ser Arg Ala Met Pro Ala Tyr Asn Trp
145                 150                 155                 160
Met Thr Val Ala Lys Ser Ala Leu Glu Ser Val Asn Arg Phe Val Ala
                165                 170                 175
Arg Glu Ala Gly Lys Tyr Gly Val Arg Ser Asn Leu Val Ala Ala Gly
            180                 185                 190

Pro Ile Arg Thr Leu Ala Met Ser Ala Ile Val Gly Gly Ala Leu Gly
        195                 200                 205

Glu Glu Ala Gly Ala Gln Ile Gln Leu Leu Glu Glu Gly Trp Asp Gln
    210                 215                 220
Arg Ala Pro Ile Gly Trp Asn Met
225                 230

<210> SEQ ID NO 6
<211> LENGTH: 251
<212> TYPE: PRT
<213> ORGANISM: L. pneumophila enoyl reductase

<400> SEQUENCE: 6

Met Lys Asn Lys Lys Gly Leu Ile Ile Gly Ile Ala Asn Glu His Ser
1               5                   10                  15

Ile Ala Trp Gly Cys Ala Lys Val Leu Tyr Glu Ala Asn Cys Glu Leu
            20                  25                  30

Ala Ile Thr Tyr Gln Asn Glu Lys Ala Lys Ser Tyr Val Gln Ser Leu
        35                  40                  45

Ala Glu Gln Val Ser Ala Ser Ile Phe Met Pro Leu Asp Val Thr Asp
    50                  55                  60

Lys Ala Gln Phe Asp Ala Leu Phe Gln Arg Ile Lys Glu Ser Trp Ser
65                  70                  75                  80

His Leu Asp Phe Val Ile His Ala Ile Ala Phe Ala Pro Lys Ala Asp
                85                  90                  95

Leu Gln Gly Arg Val Val Asp Cys Ser Lys Glu Gly Phe Met Val Ala
            100                 105                 110

Met Asp Val Ser Cys His Ser Leu Ile Arg Leu Ala Lys Ala Ala Glu
        115                 120                 125

Pro Leu Met Val Asn Gly Gly Ser Ile Met Thr Met Ser Tyr Tyr Gly
    130                 135                 140

Ala Glu Lys Val Val Lys Asn Tyr Asn Leu Met Gly Pro Val Lys Ala
145                 150                 155                 160

Ala Leu Glu Thr Ser Val Arg Tyr Leu Ala Met Glu Leu Gly Ser Lys
                165                 170                 175

Lys Ile Arg Val Asn Ala Ile Ser Pro Gly Pro Ile Ser Thr Arg Ala
            180                 185                 190

Ala Ser Gly Leu Ala Asp Phe Asp Lys Leu Met Glu Lys Ala Ala Asn
        195                 200                 205

Glu Ala Pro Leu His Gln Leu Val Thr Ile Glu Ala Ile Gly Glu Met
    210                 215                 220
```

-continued

```
Ala Ala Phe Leu Val Ser Asp Lys Ala Val Ser Ile Thr Gly Gln Ile
225                 230                 235                 240

Leu Tyr Val Asp Ala Gly Tyr Asn Ile Lys Gly
                245                 250

<210> SEQ ID NO 7
<211> LENGTH: 268
<212> TYPE: PRT
<213> ORGANISM: L. pneumophila enoyl reductase

<400> SEQUENCE: 7

Met Gly Gly Asp Thr Ile Val Gly Phe Leu Thr Gly Lys Lys Ala Leu
1               5                   10                  15

Ile Val Gly Leu Ala Ser Asn Arg Ser Ile Ala Tyr Gly Ile Ala Lys
            20                  25                  30

Ala Phe His Asn Gln Gly Ala Glu Leu Ala Phe Thr Tyr Gln Asn Glu
        35                  40                  45

Lys Leu Gln Ser Arg Val Glu Thr Met Ala Ser Glu Phe Asn Ser Thr
    50                  55                  60

Leu Val Phe Pro Cys Asp Val Ala Ser Asp Glu Glu Ile Lys Ala Val
65                  70                  75                  80

Phe Asp Asn Leu Arg Asn His Trp Asp Lys Leu Asp Ile Leu Val His
                85                  90                  95

Ser Val Ala Tyr Ala Pro Ala Asp Gln Ile Ser Gly Asp Phe Val Glu
            100                 105                 110

Cys Ala Asn Arg Glu Gly Phe Arg Ile Ala His Asp Ile Ser Ala Tyr
        115                 120                 125

Ser Leu Ile Gly Leu Ser Gln Ala Ala Leu Pro Met Met Leu Asp Thr
    130                 135                 140

Gln Gly Ser Ile Leu Thr Leu Ser Tyr Tyr Gly Ala Glu Lys Ala Val
145                 150                 155                 160

Pro Asn Tyr Asn Val Met Gly Val Ala Lys Ala Ser Leu Glu Ala Ser
                165                 170                 175

Val Arg Tyr Leu Ala Ala Ser Leu Gly Ser Arg Gly Leu Arg Ile Asn
            180                 185                 190

Ala Ile Ser Ala Gly Pro Ile Lys Thr Leu Ala Ala Ala Gly Ile Lys
        195                 200                 205

Asp Phe Arg Lys Ile His Ala Ala Tyr Ala Asn Ile Thr Pro Leu Gln
    210                 215                 220

Arg Asn Val Thr Ala Asp Glu Val Gly Asn Thr Ala Ala Phe Leu Cys
225                 230                 235                 240

Ser Asp Leu Ala Ser Gly Ile Thr Gly Glu Val Leu His Val Asp Ala
                245                 250                 255

Gly Tyr His Ala Val Ser Ala Met Ser Glu Leu Gly
            260                 265
```

ANTIMICROBIAL ACTIVITY OF GEMFIBROZIL AND RELATED COMPOUNDS AND DERIVATIVES AND METABOLITES THEREOF

The invention disclosed herein was made with Government support under Grant Nos. AI23549 and AI20516 from NIAID. Accordingly, the U.S. Government has certain rights in this invention.

BACKGROUND OF THE INVENTION

Throughout this application, various publications are referenced by a number in brackets. Full citations for these publications may be found listed by number at the end of the specification immediately preceding the claims. The disclosures of these publications in their entireties are hereby incorporated by reference into this application in order to more fully describe the state of the art as known to those skilled therein as of the date of the invention described and claimed herein.

Gemfibrozil (GFZ) is a compound that has been utilized as a drug for increasing intracellular accumulation of hydrophilic anionic agents (U.S. Pat. No. 5,422,372, issued Jun. 6, 1995) and as a lipid regulating composition (U.S. Pat. No. 4,859,703, issued Aug. 22, 1989). Gemfibrozil has been shown to be effective in increasing the amount of cholesterol excreted in to bile. (Ottmar Leiss et al., Metabolism, 34(1):74–82 (1985)). Gemfibrozil is described in U.S. Pat. No. 3,674,836 and in The Merck Index, 11 ed., Merck & Co., Inc. Rahway, N.J. 1989; #4280. Gemfibrozil, a drug which therapeutically lowers triglycerides and raises HDL-cholesterol levels, previously has not been reported to have antimicrobial activity. (Brown, 1987; Oliver et al., 1978 and Palmer et al., 1978).

SUMMARY OF THE INVENTION

The present invention provides for a method of inhibiting activity of an enoyl reductase enzyme in a cell which comprises contacting the cell with a compound having the structure:

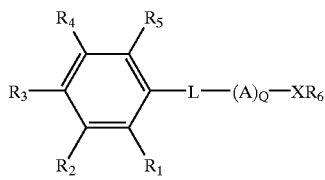

wherein each of $R_1$, $R_2$, $R_3$, $R_4$, $R_5$ and $R_6$ is independently selected from the group consisting of: —H, —F, —Cl, —Br, —I, —OH, —$OR_7$, —CN, —$COR_7$, —$SR_7$, —$N(R_7)_2$, —NR; —$COR_8$, —$NO_2$, —$(CH_2)_p$ —$OR_7$, —$COSR_7$, —COOH, —$CONH_2$, —$NH_2$, a straight chain or branched, substituted or unsubstituted $C_1$–$C_{10}$ alkyl, $C_2$–$C_{10}$ alkenyl, $C_2$–$C_{10}$ alkynyl, $C_3$–$C_{10}$ cycloalkyl, $C_3$–$C_{10}$ cycloalkenyl, thioalkyl, methylene thioalkyl, acyl, phenyl, substituted phenyl, or heteroaryl;

wherein L is alternatively —N—, —S—, —C— or —C—;

wherein $R_7$ is independently selected from the group consisting of —H, —F, —Cl, —Br, —I, —OH, —CN, —COH, —$SH_2$, —$NH_2$, —NHCOH, —$(CH_2)_p$OH, a straight chain or branched, substituted or unsubstituted $C_1$–$C_{10}$ alkyl, $C_2$–$C_{10}$ alkenyl, $C_2$–$C_{10}$ alkynyl, $C_3$–$C_{10}$ cycloalkyl, $C_3$–$C_{10}$ cycloalkenyl, thioalkyl, methylene thioalkyl, acyl, phenyl, substituted phenyl, or heteroaryl;

wherein A is selected from the group consisting of —$N_2$—, —NH—, —C=C=$CH_2$—, —C≡C—$C_2HOH$—, —C≡C—$CH_2$—, —$CH_2$—$CH_2$—O—, —$CH_2$—$CH_2$—$CH_2$—O—, —S—, —S (=O)$_2$—, —C=O—, —C=O—O—, —NH—C=O—, —C=O—NH—;

wherein Q is independently an integer from 1 to 10, or if Q is 1, A may be a ($C_1$–$C_{10}$)-alkyl chain, ($C_1$–$C_{10}$)-alkenyl chain or ($C_1$–$C_{10}$)-alkynyl chain which is branched or unbranched, substituted or unsubstituted and is optionally interrupted 1 to 3 times by —O— or —S— or —N—;

wherein X is —$CO_2$—, —CH=$CH_3$, phenyl, substituted phenyl, or heteroaryl, —O-phenyl$(CH_3)_2$, —C($CH_2$)$_2$—CO—$NH_2$, —C($CH_2$)$_2$—COOH;

or a pharmaceutically acceptable salt or ester thereof, which compound is present in a concentration effective to inhibit activity of the enzyme.

BRIEF DESCRIPTION OF THE FIGURES

FIG. 1. Comparison of fatty acids synthesized by *E. coli* [5], and *L. pneumophila* [6, 7]. The number immediately preceding the colon refers to the number of carbons, the number following the colon refers to the number of double bonds, the superscript number refers to the location of the double bonds. a=anteiso; i=iso; OH=hydroxy.

FIG. 7. Structures of the fibric acids used in these experiments; gemfibrozil (GFZ), clofibrate (CFX), bezafibrate (BZF), fenofibrate (FNF). Note that GFZ, CFA, BZF, were used as the free acids, while FNF was used as the isopropyl ester.

FIG. 8. Bacteria were screened for sensitivity to gemfibrozil using a zone of inhibition assay. The assay was performed by overlaying bacteria on a suitable nutrient agar plate, adding a disk containing 2 mg gemfibrozil to the plate, and incubating the plate at the appropriate temperature until bacterial growth was apparent. The presence of a zone of inhibition was considered positive for sensitivity. The fraction in parenthesis after each bacterial species indicates how many of the strains tested of each species was sensitive to GFZ.

FIG. 9. GFZ zones of inhibition for S. aureus and S. epidermidis on LB versus TSB agar medium. Four ATTC S. aureus strains and one S. epidermidis strain were grown overnight in Brain-Heart Infusion (BHI) broth. The cultures were diluted to $10^7$ and $10^6$ CFUs/ml in BHI, and 100 µl aliquots of each dilution were plated on LB or TSB agar in duplicate. The plates were incubated at 37° C. overnight prior to measuring the diameter of the zones in mm.

FIG. 10. Susceptibility of M. tuberculosis to GFZ. Twenty seven M. tuberculosis strains, demonstrating different drug resistance profiles, were tested for sensitivity to gemfibrozil. OADC-enriched Middlebrook agar plates with quadrants containing 0, 100, or 200 µg/ml of GFZ in were prepared. 100 µls of a standard dilution of each resuspended M. Tuberculosis strain in sterile water was added to each quadrant, and the plates were incubated for three weeks at 37° C. No growth was indicated by (O); quadrants containing fewer than 50 colonies were counted, and the numbers given are the average number of colonies in duplicate quadrants; quadrants containing 50–100 colonies are indicated by a (+); quadrants containing 100–200 colonies are indicated by a (++); quadrants containing 200–500 colonies are indicated by a (+++); and quadrants with confluent growth are indicated by (++++). The drugs to which each strain are resistant are indicated to the left of each strain; S=streptomycin 2 µg/ml; I=isoniazid 1 µg/ml; R=rifampin 1 µg/ml; E=ethambutol 5 µg/ml; K=kanamycin 6 µg/ml; O=ofloxacin 4 µg/ml; C=ciprofloxacin 2 µg/ml; $R^L$=Low level resistance to isoniazid at 0.2 µg/µl, but sensitive to isoniazid at higher concentrations.

FIG. 11. GFZ inhibits the growth of M. tuberculosis strains in 7H9 broth. Approximately $10^7$ bacteria were added to 5 mls of Middlebrook 7H9 broth with glycerol and incubated at 37° C. After 21 days the cultures were visually assessed for turbidity.

FIG. 36. Structures of the enoyl reductase substrates and inhibitors.

Therefore, the large boxes correspond to 5 mls or 10 minutes, while the small boxes correspond to 1 ml or 2 minutes. 0.5 ml fractions were collected post 280 nm detection. The injection is on the right side of the tracing and the four major peaks are numbered in order of appearance. The radioactive fractions are indicated as dots along the X-axis.

Figure 40:
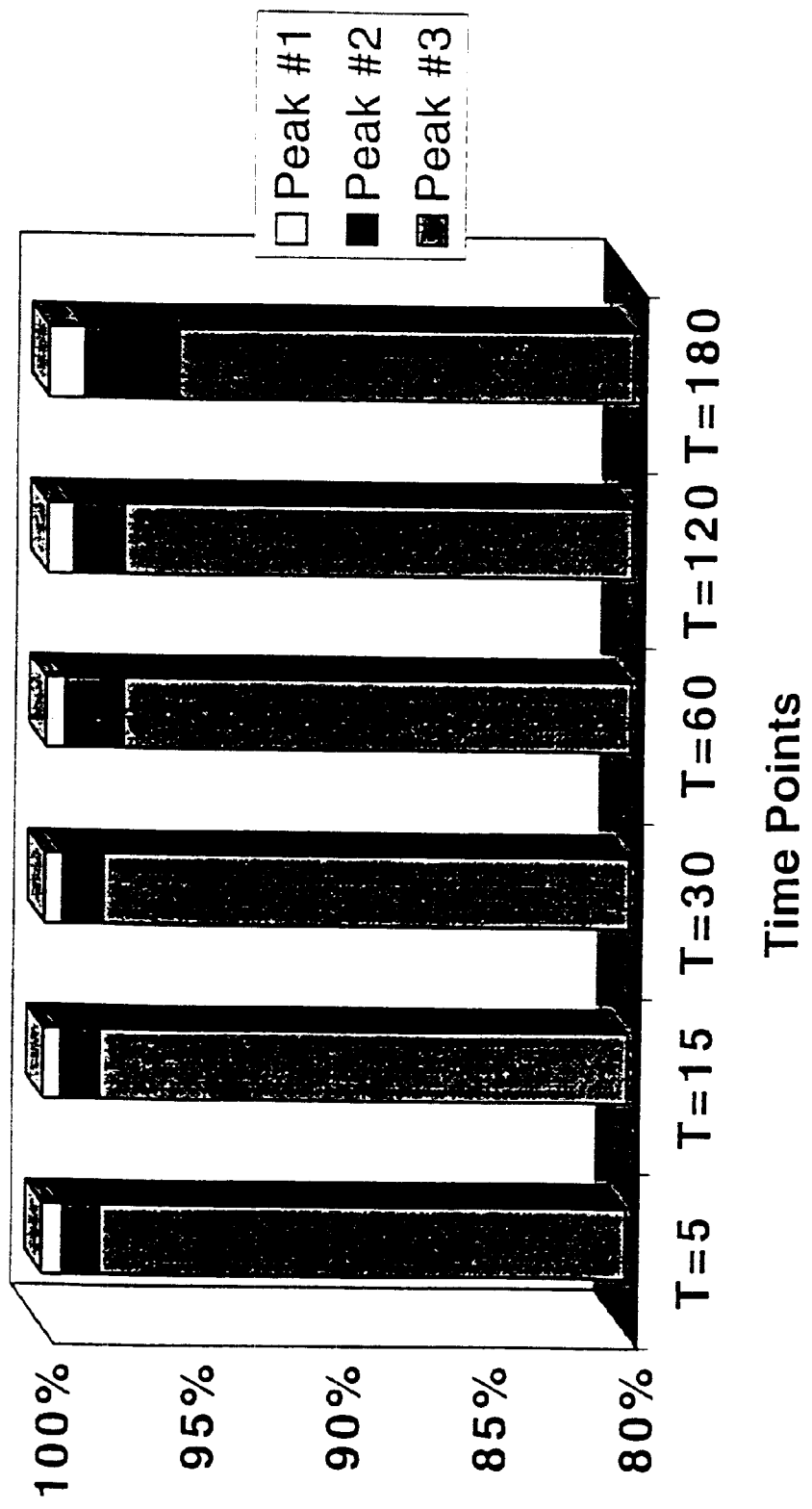

FIG. 40. FPLC analysis of cytoplasmic extracts of *L. pneumophila* incubated with $^3$H-GFZ. *L. pneumophila* were incubated with $^3$H-GFZ in AYE broth at 37° C. Samples were collected at the times indicated. The samples were pelleted, washed, lysed, and filtered through 30 and 10 kDa Centricon filters. The filtrate was applied to a Superose12™ FPLC column. Fractions were collected and CPMs assessed by liquid scintillation spectrometry. Percentage of CPMs in each of the three major FPLC peaks relative to total CPMs for samples harvested at the time points indicated.

Figure 41:
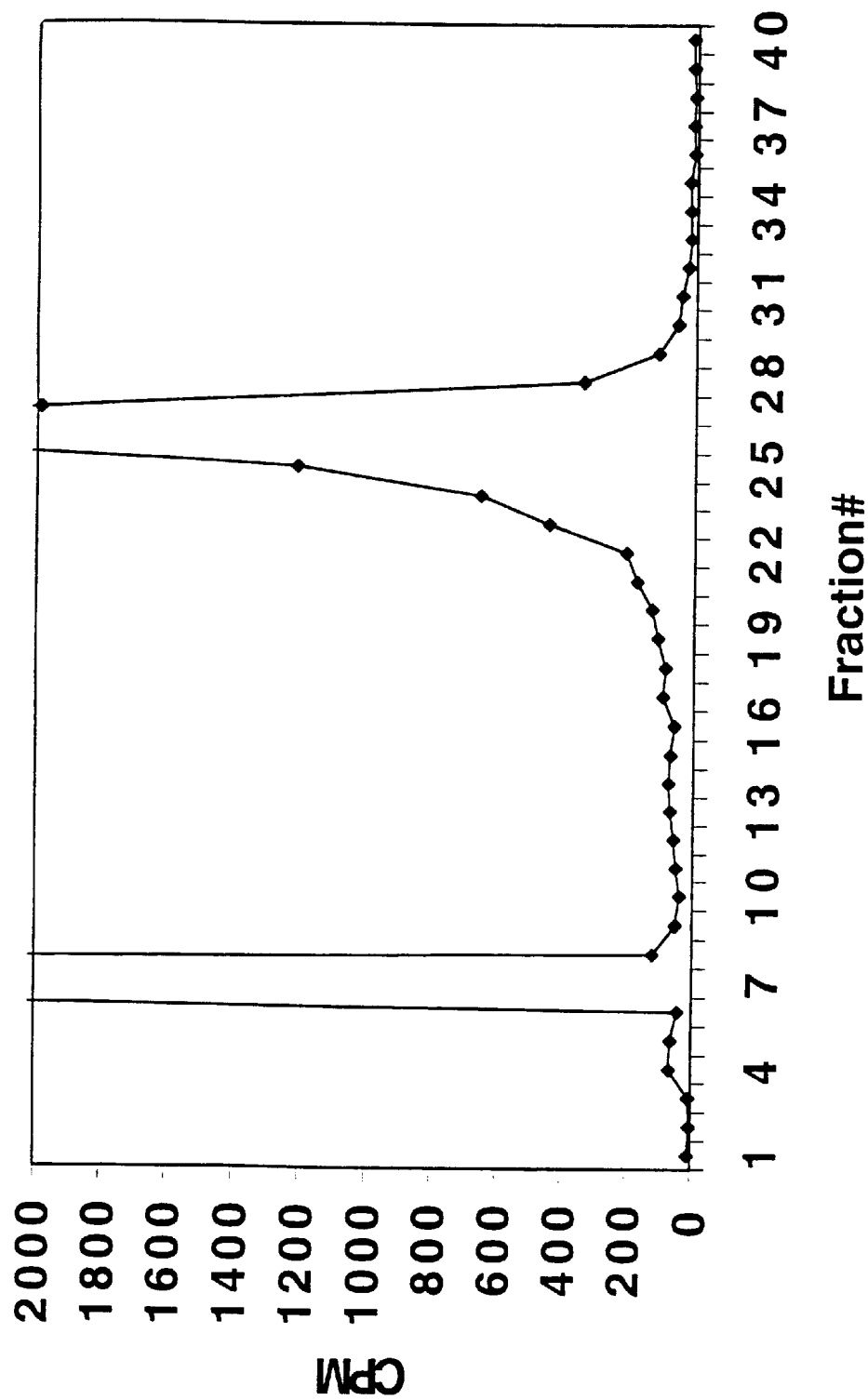

FIG. 41. HPLC of the $^3$H-GFZ standard. $^3$H-GFZ (1 $\mu$Ci) dissolved in 100% EtOH was applied to a reverse phase C18 $\mu$Bondapack™ column. 0.5 ml fractions were collected every thirty seconds and assessed for CPMs by liquid scintillation spectrometry.

Figure 42:
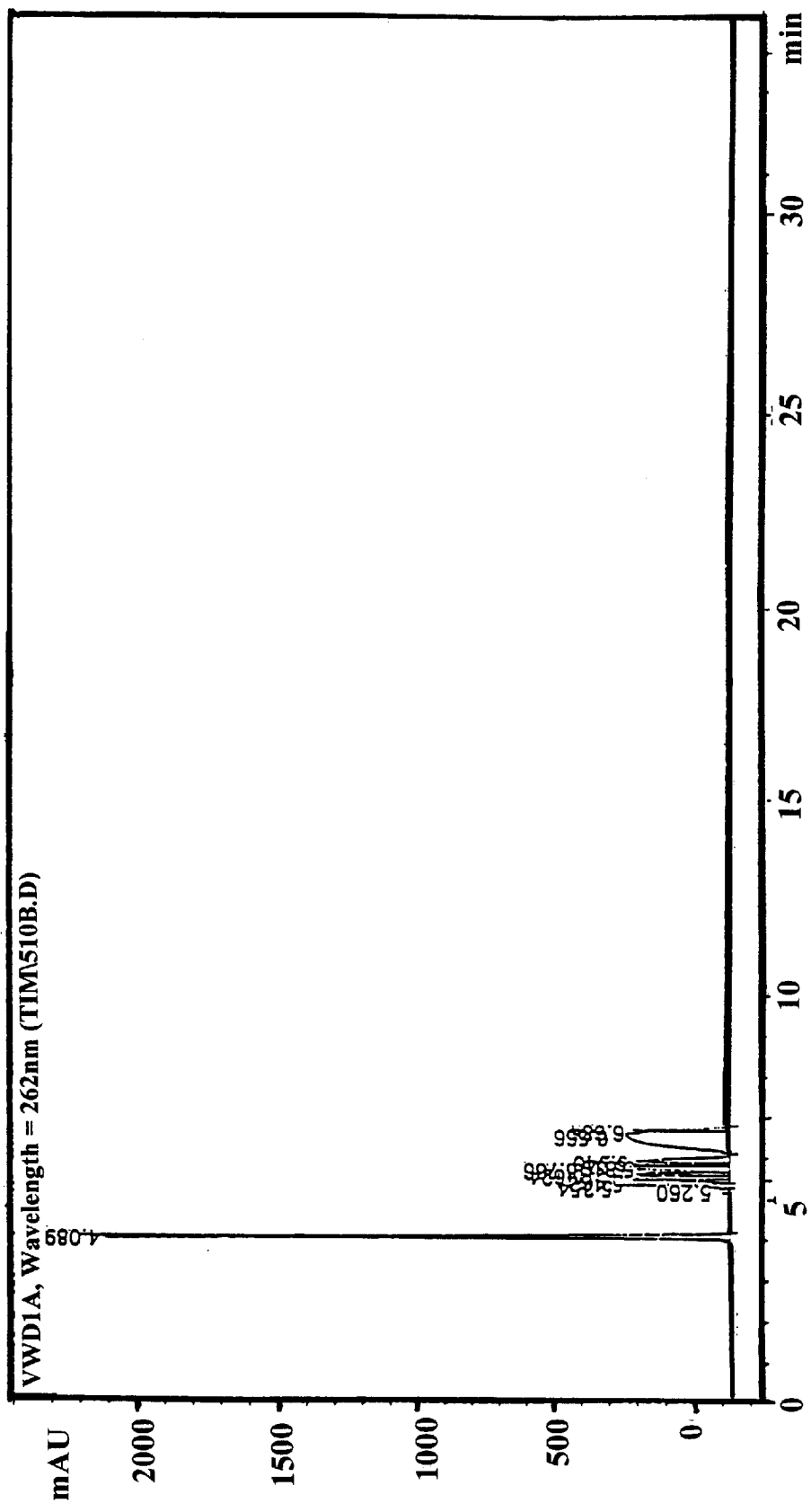
Figure 43A:
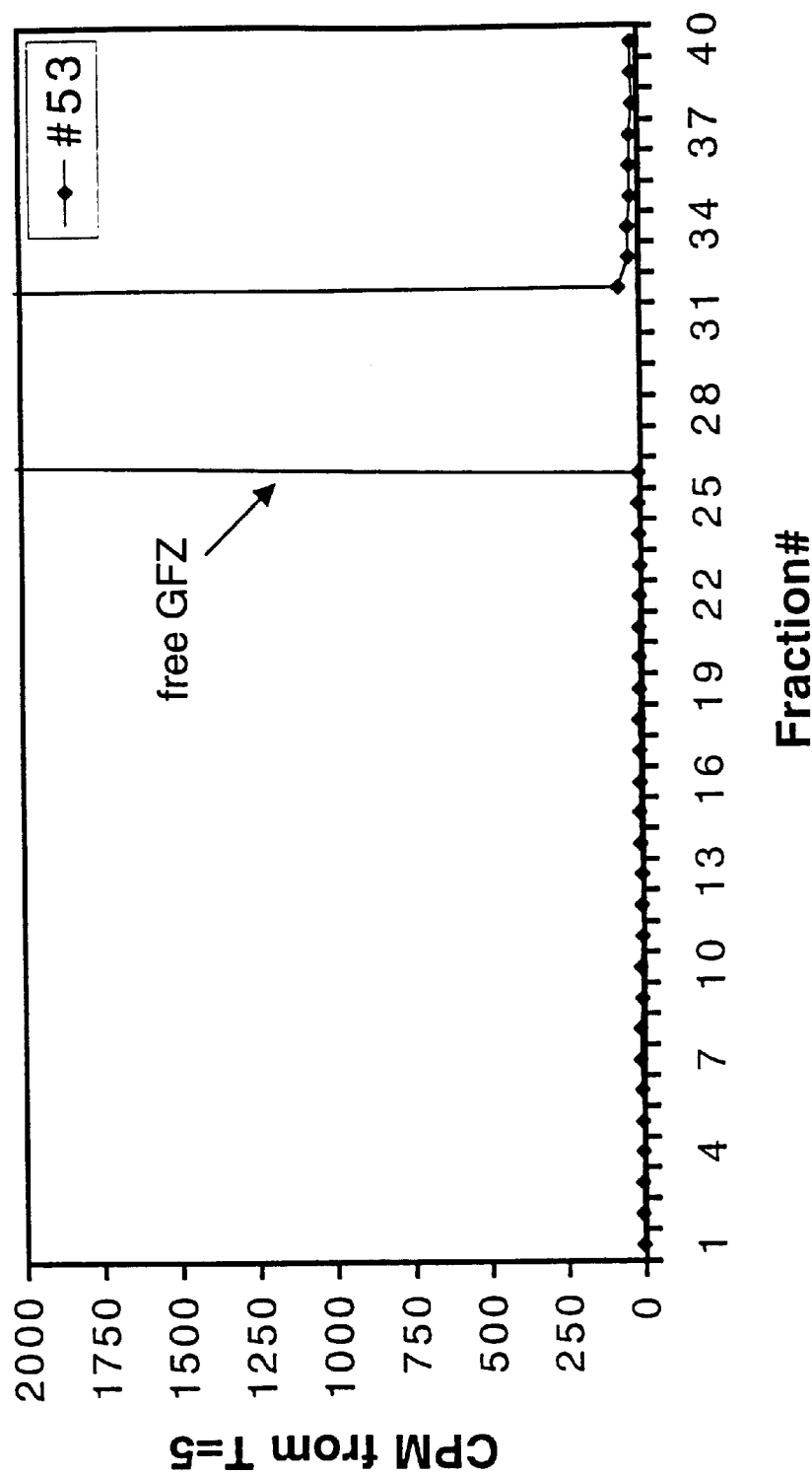
Figure 43B:
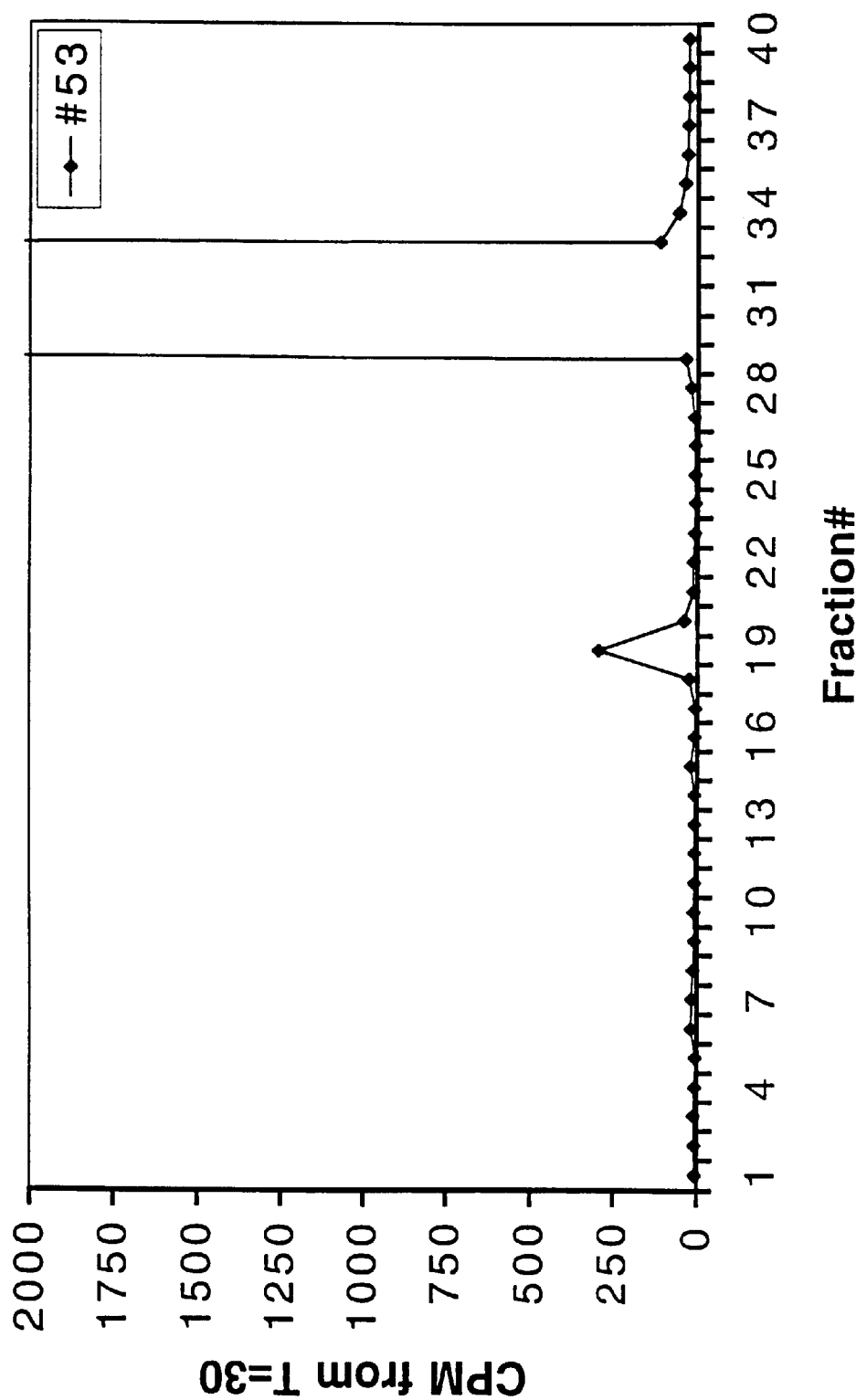
Figure 43C:
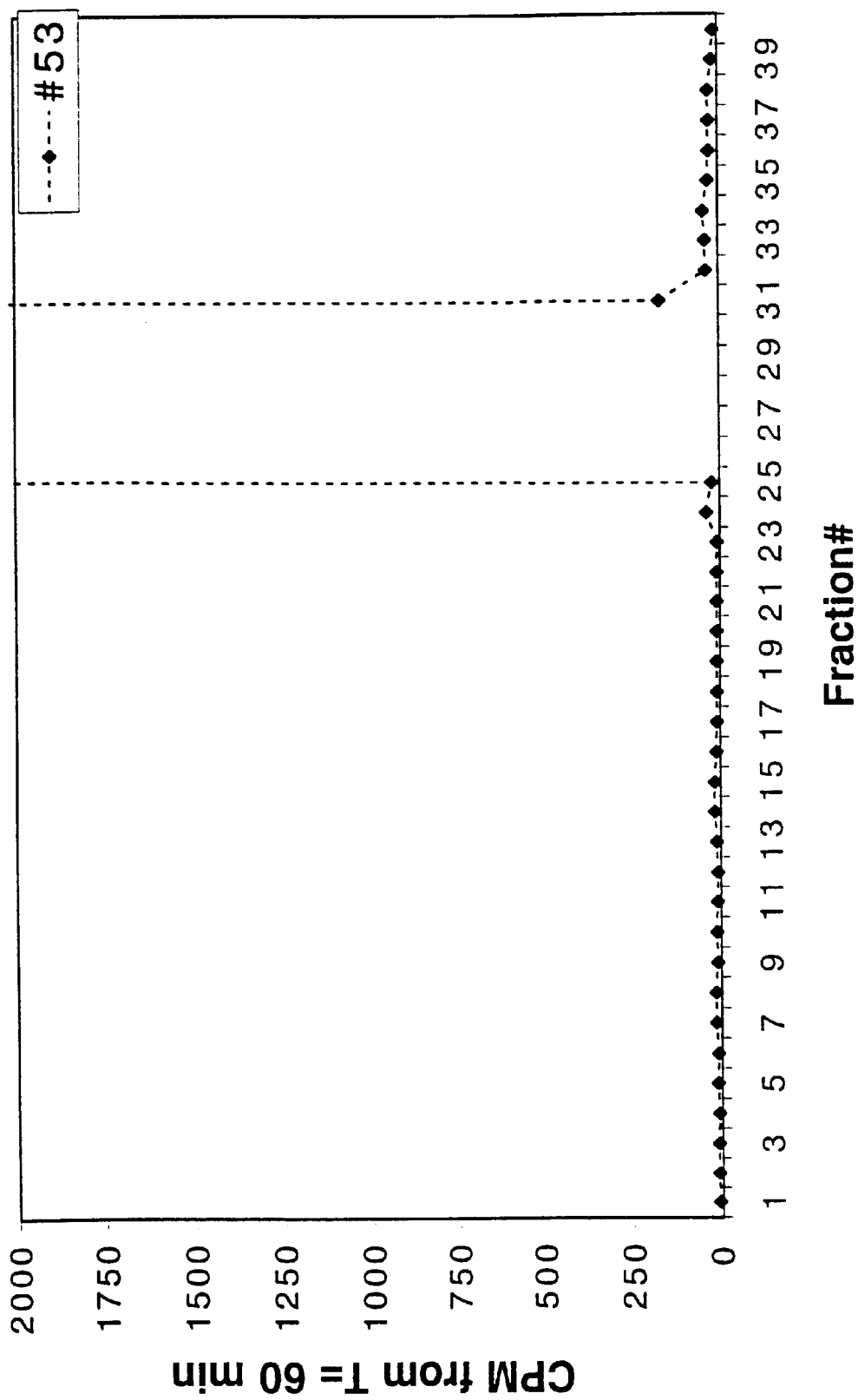
Figure 43D:
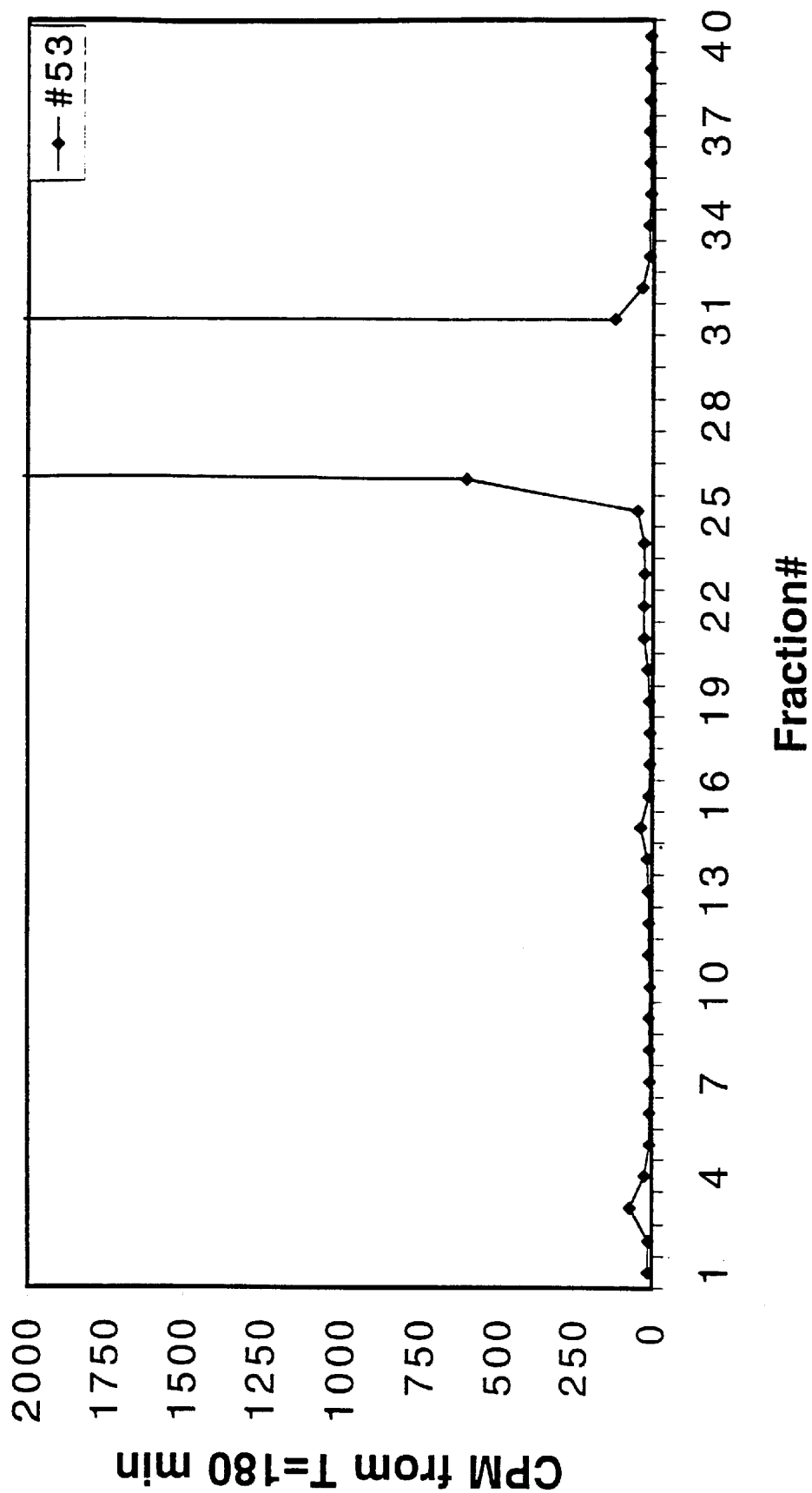
Figure 44A:
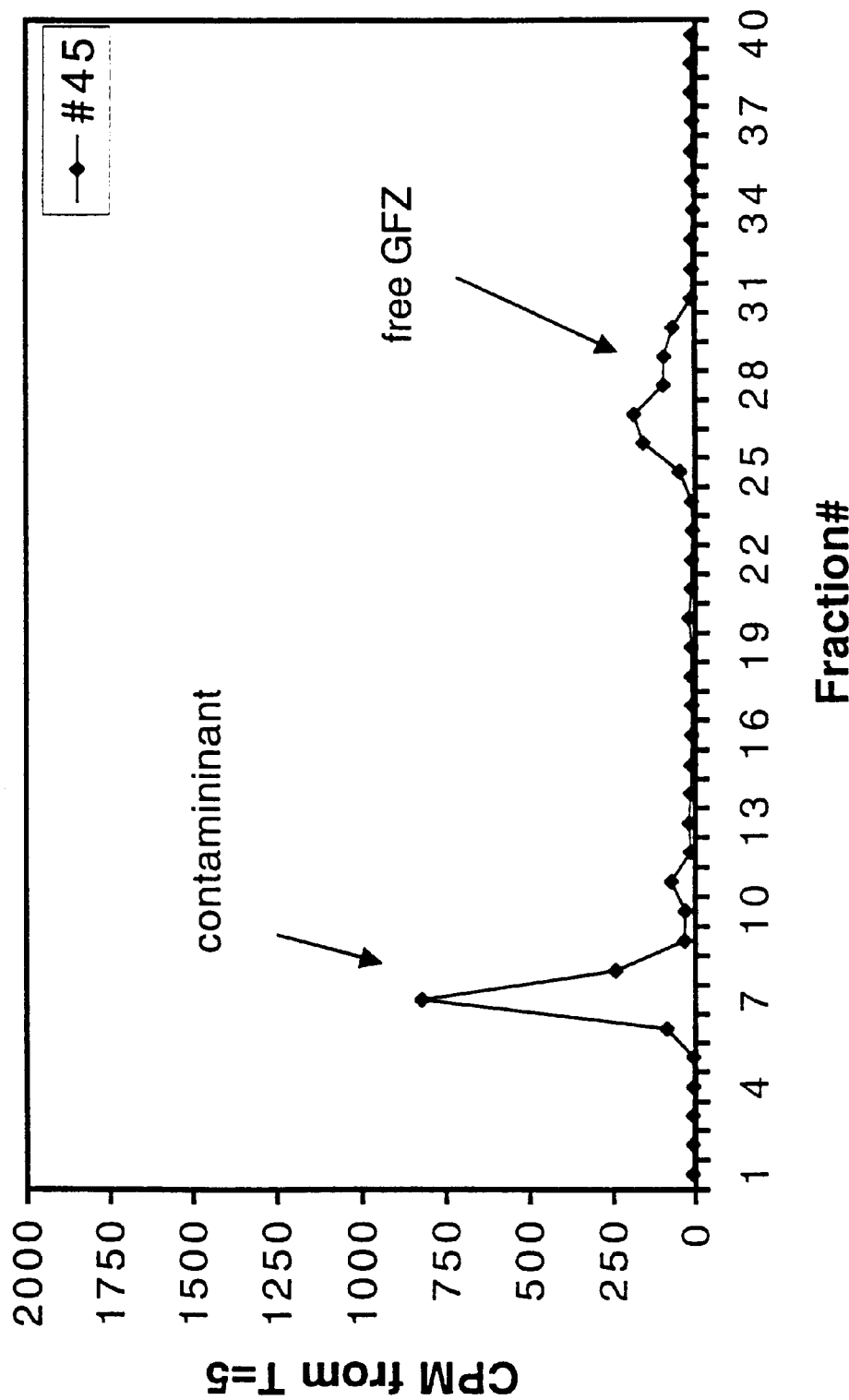
Figure 44B:
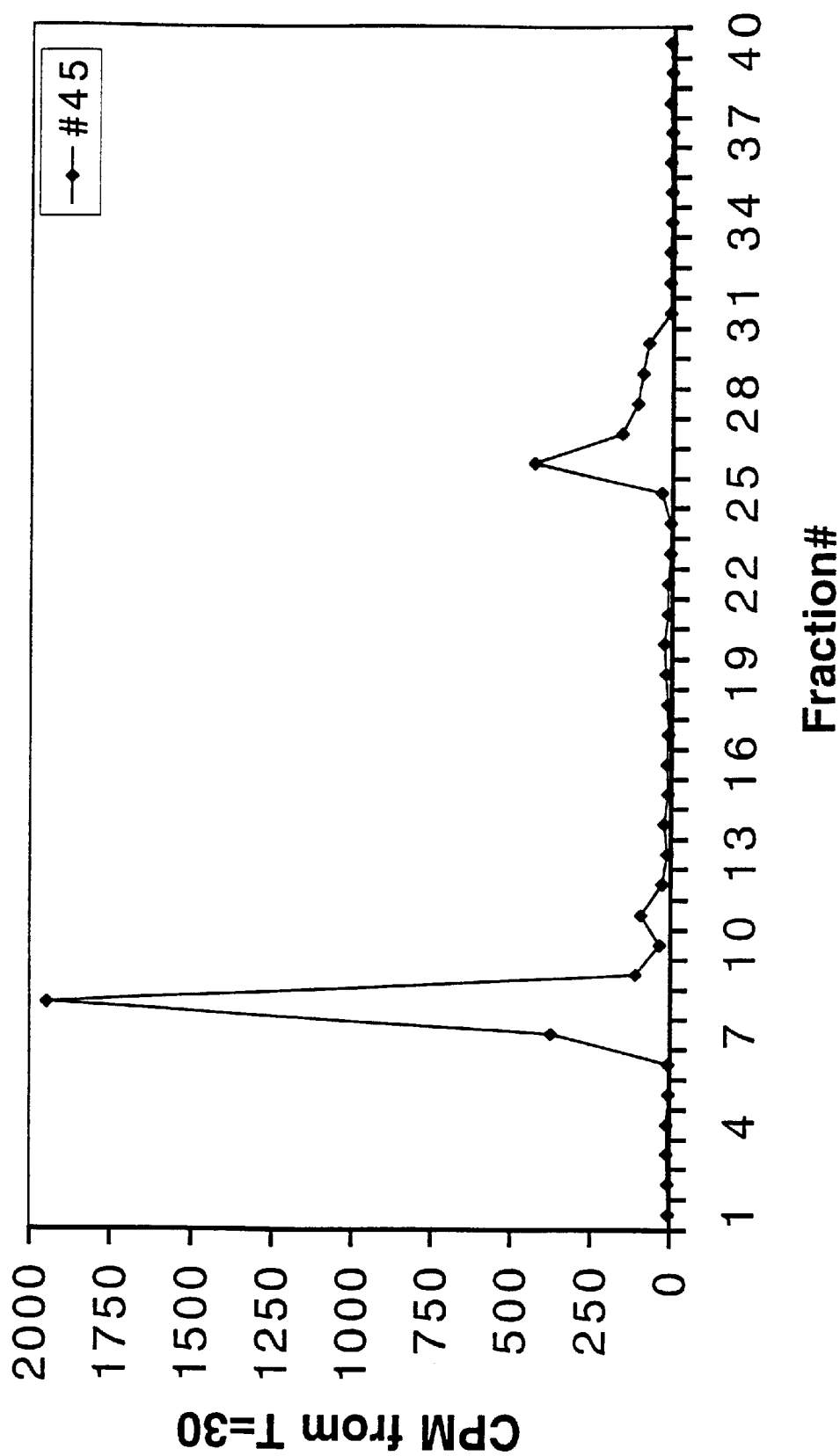
Figure 44C:
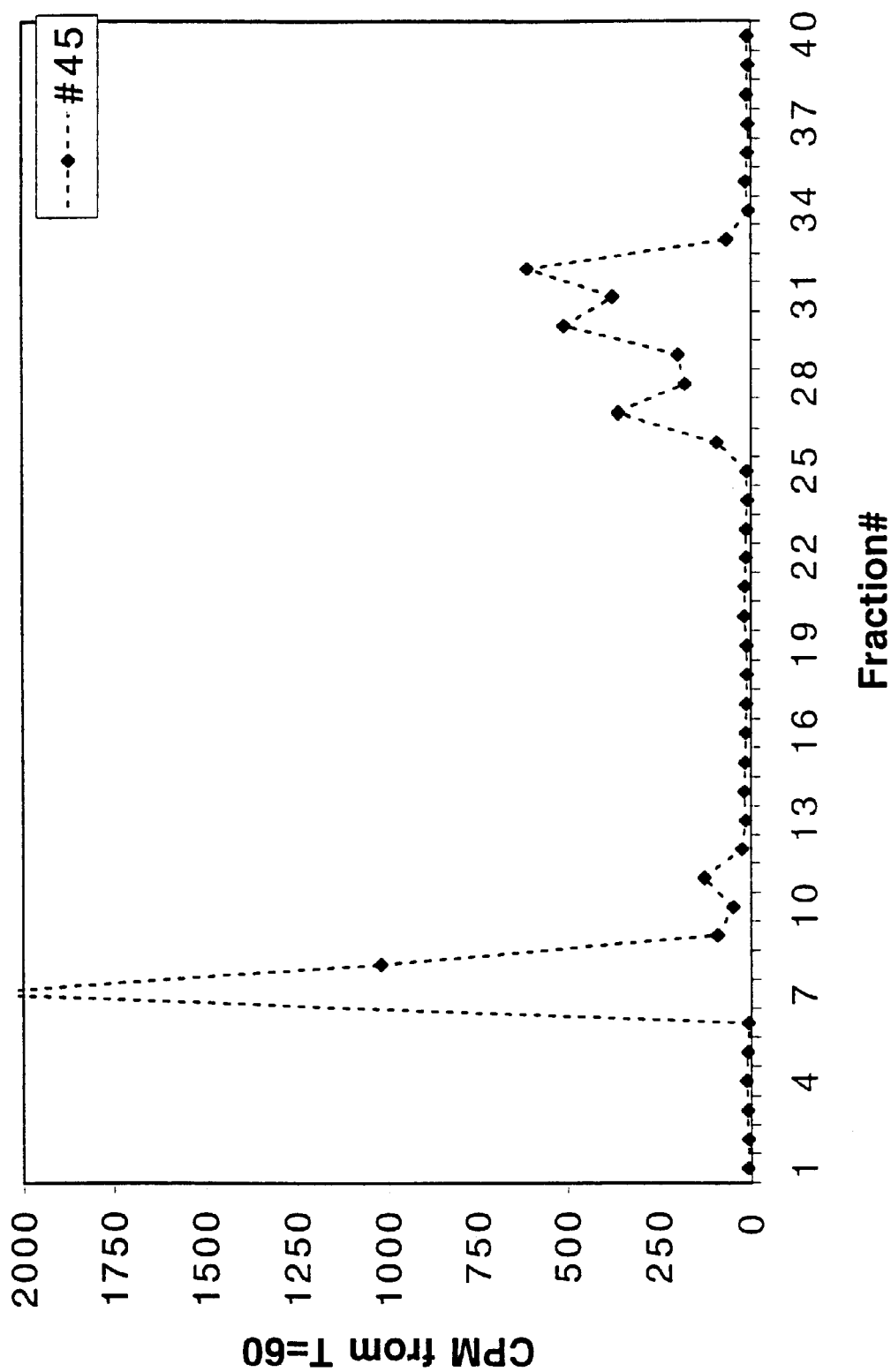
Figure 44D:
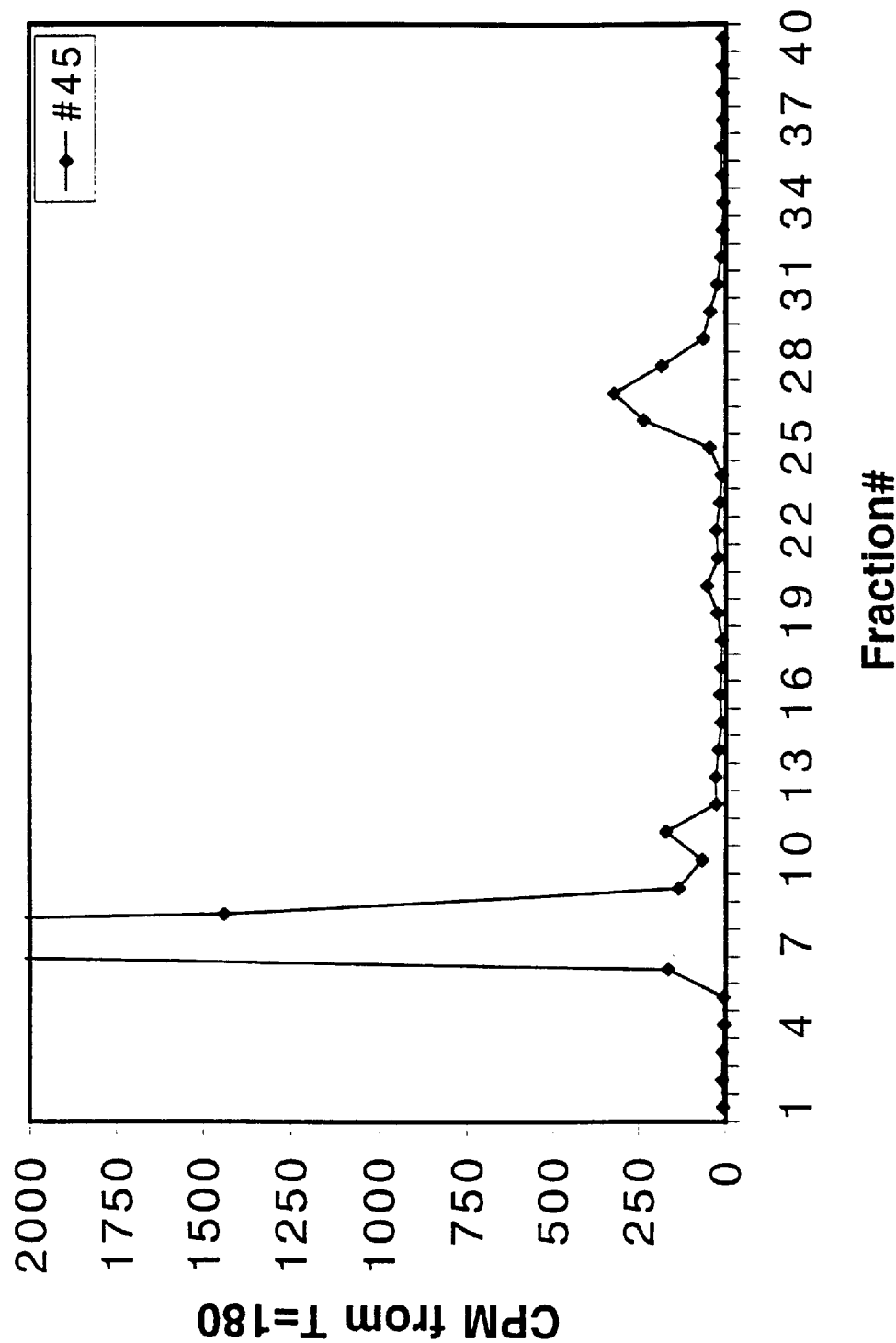
Figure 45A:
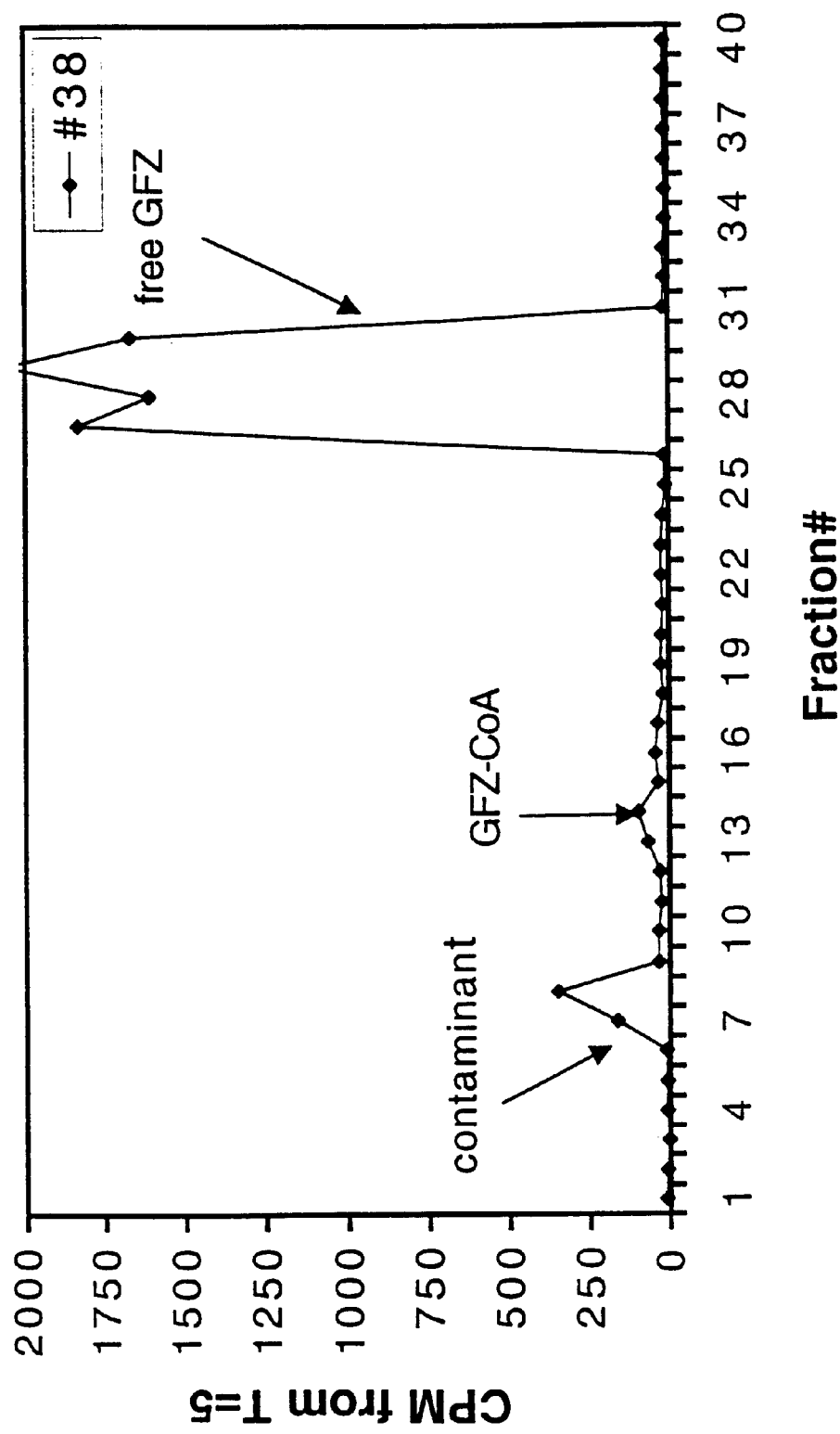
Figure 45B:
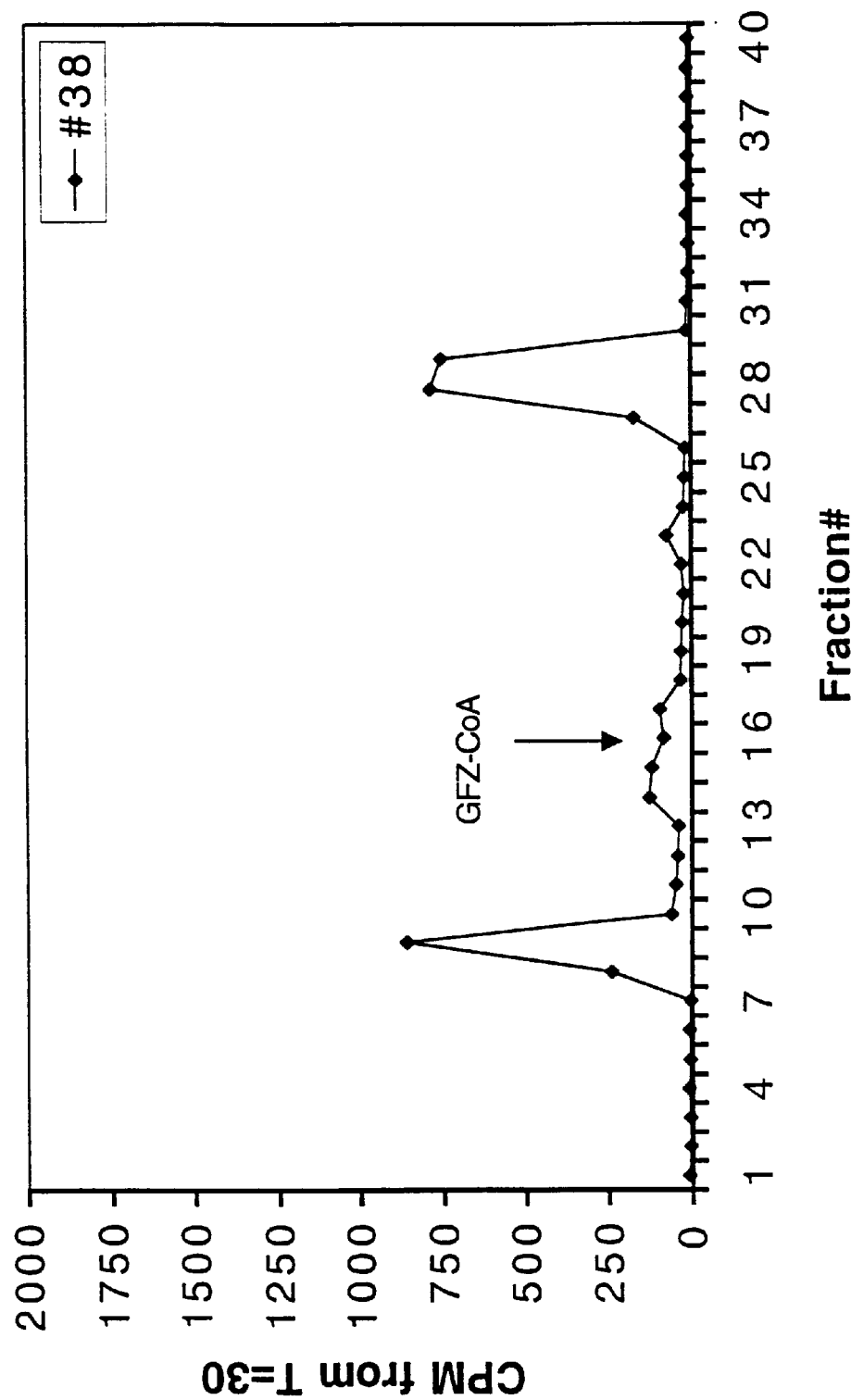
Figure 45D:
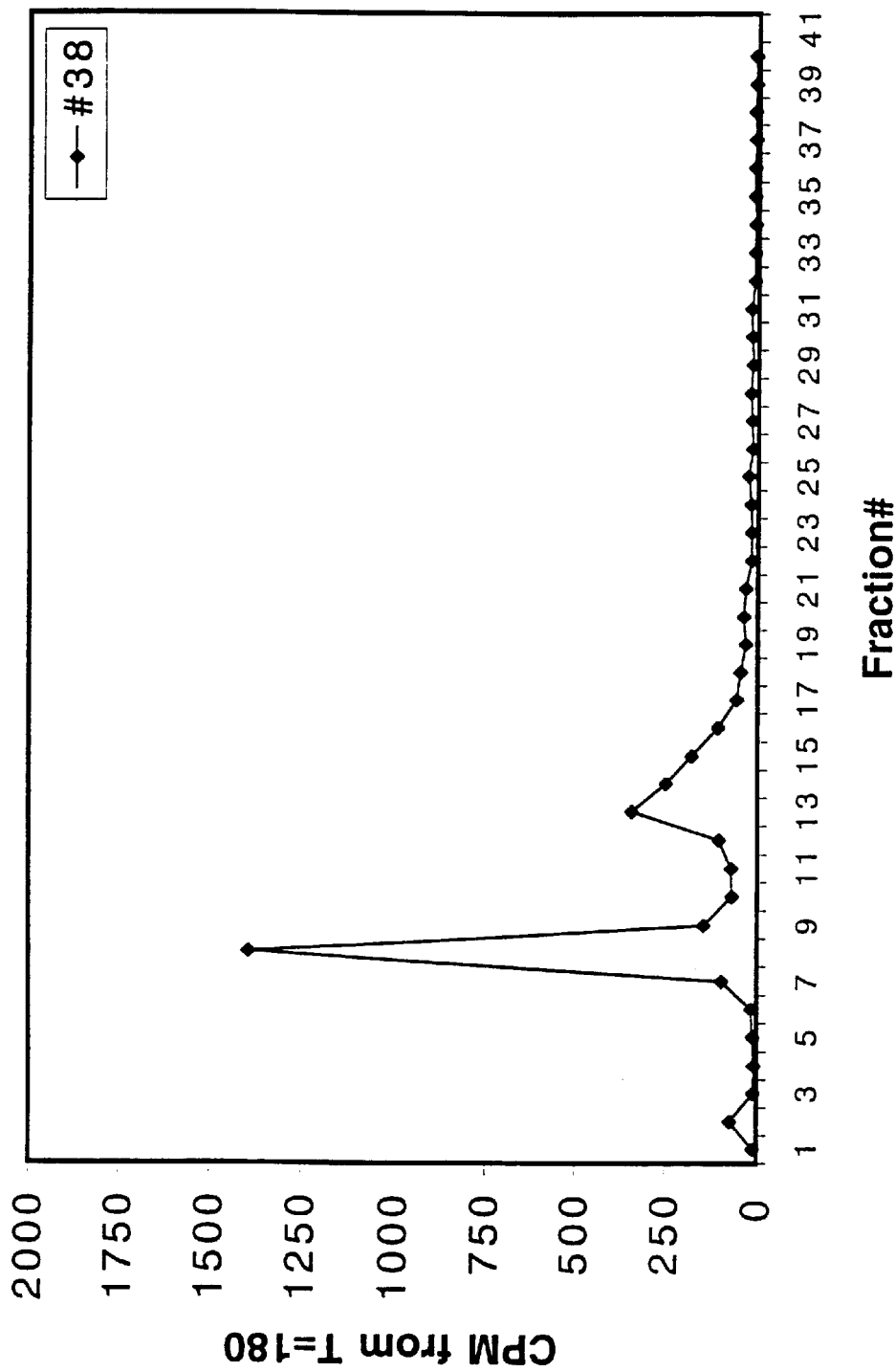

FIG. 42. HPLC of the GFZ-CoA standard. 500 $\mu$l of a mixture of CoA (30%) and GFZ-CoA (70%) dissolved in water at a concentration of 500 $\mu$g/ml was added to a reverse phase C18 $\mu$Bondapack™ column. 0.5 ml fractions were collected every thirty seconds and analyzed at OD=262 nm. Fractions eluting at 5–7 min (fractions #10–14) represent GFZ-CoA; the fraction eluting at 4 min (fraction #8) represents CoA.

FIGS. 43A–D. Summary of the HPLC data from FPLC fraction #53. Filtered lysates of *L. pneumophila* incubated at 37° C. with $^3$H-GFZ for the indicated length of time were applied to an FPLC column and fractions were collected. Fraction #53 from the third peak to elute from this FPLC column was applied to a reverse phase HPLC column. Fractions from the HPLC column were collected and assessed by liquid scintillation counting. Fractions eluting from 12.5–15 minutes (fractions #25–30) contained radioactivity and co-chromatographed with $^3$H-GFZ as determined earlier (FIGS. 8–5). a) T=5 min; b) T=30 min c) T=60 min; d) T=180 min.

Figure 2:
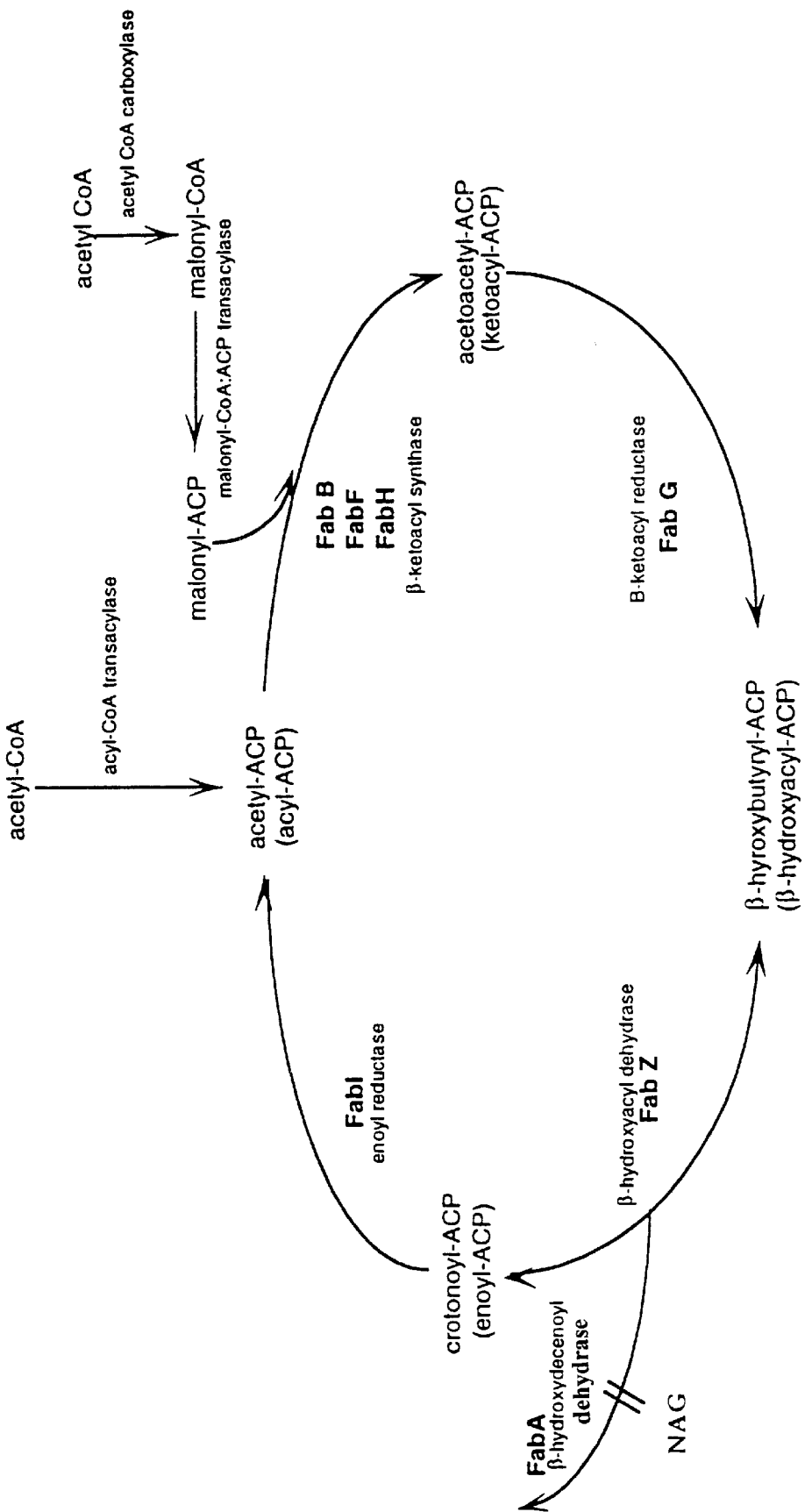
FIG. 2. Fatty acid synthesis in *E. coli*. Initiation of fatty acid synthesis occurs with the condensation of acetyl-CoA with malonyl-ACP, or, conversion of acetyl-CoA to acetyl-ACP prior to condensation with malonyl-ACP. Subsequent elongation occurs though the sequential addition of two carbon units using malonyl-ACP as the donor. Elongation occurs through a four step process in which the first step, condensation, is mediated by β-ketoacylsynthase (FabB, FabF, FabH); the second step, reduction, is mediated by β-ketoacyl reductase (FabG); the third step, dehydration, is mediated through β-hydroxyacyl dehydratase (Fab Z); and the fourth and final step, reduction, is mediated through enoyl reductase (FabI). Unsaturated fatty acids are synthesized by the diversion of β-hydroxydecanol-ACP to FabA which catalyzes the formation of a double bond and then returns the unsaturated fatty acid to the cycle. The double lines indicate points where compounds act to inhibit fatty acid synthesis. The compounds are: DZB, diazoborines; ETH, ethionamide; INH, isoniazid; CER, cerulenin; TLM, thiolactomycin; NAG, 3-decenoyl-N-acetylcysteamine.
Figure 3:
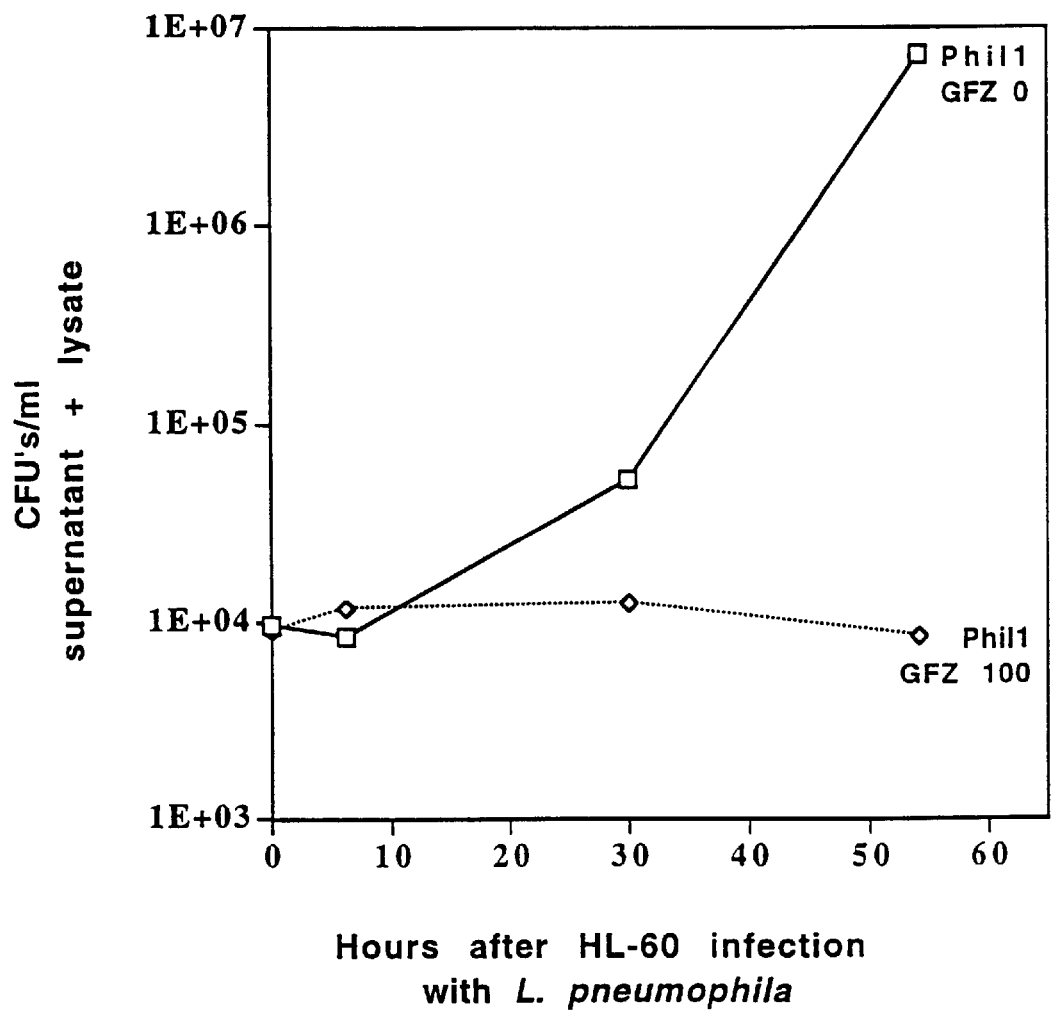
FIG. 3. GFZ inhibits intracellular multiplication of *L. pneumophila* in phorbol myristate acetate-differentiated HL-60 cells. HL-60 cells were differentiated into macrophages by treatment with PMA for 48 hours, plated as a monolayer in the wells of a microtiter plate, and synchronously infected with *L. pneumophila* (final multiplicity of infection of 0.01). After 2 hrs, the cells were washed to remove extracellular bacteria, overlaid with fresh RPMI-2 mM GLN-10% NHS without or with GFZ (100 μg/ml), and incubated at 37° C. At the times indicated, the cells and medium were harvested and assayed for *L. pneumophila*. Illustrated is an experiment typical of three performed. Each point is the average of three separate wells (+/–) the SEM.
Figure 4:
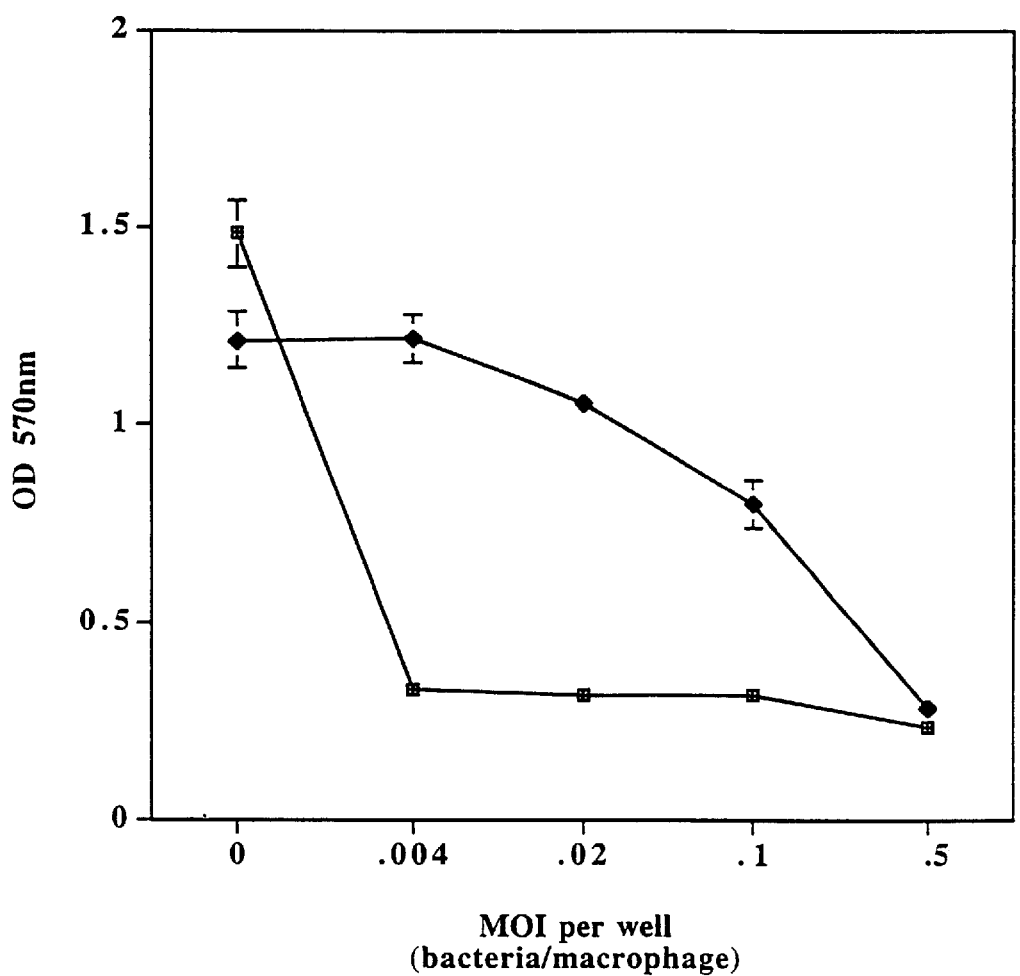
FIG. 4. GFZ protects HL-60 cells from the cytotoxic effects of an *L. pneumophila* infection over a five day incubation period. HL-60 cells were differentiated and infected in microtiter wells as described in Materials and Methods. GFZ was added to a final concentration of 0 or 100 µg/ml 2.5 hours post-infection. After 5 days, the dye MTT was added, and the $A_{570}$ of each well was measured. The $A_{570}$ value is proportional to the number of viable macrophages in the wells. Each point is the average of six separate wells (+/-) the SEM. This experiment is representative of three experiments, all of which yeilded similar results.
Figure 5:
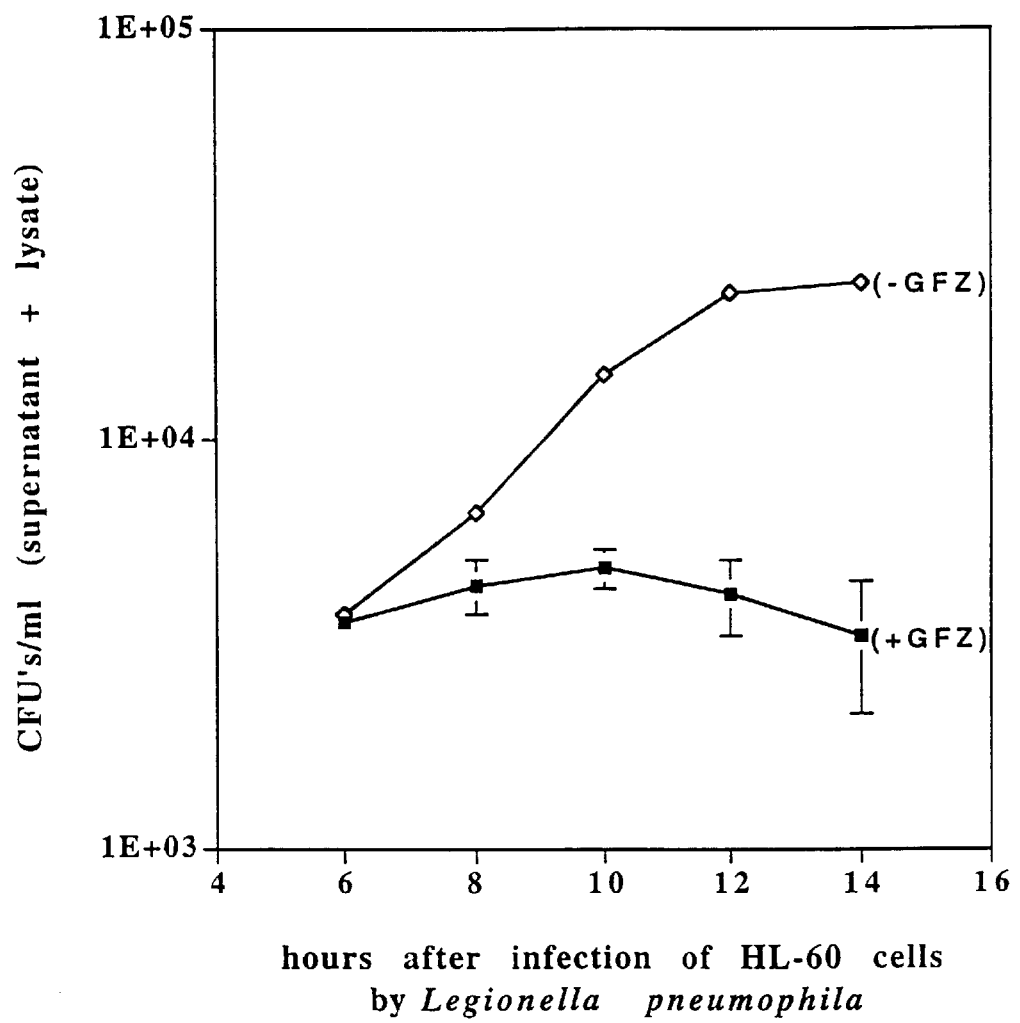
FIG. 5. GFZ inhibits the first round of intracellular multiplication of L. pneumophila in PMA-differentiated HL-60 cells. PMA-differentiated HL-60 cells at a concentration of $4 \times 10^6$ cells/ml were synchronously infected with L. pneumophila at an MOI of 0.01 in suspension. 100 µl aliquots were plated in the wells of a 96 well microtiter plate. The plates were centrifuged to pellet the cells and bacteria at the bottom of the wells. The monocytes were allowed to internalize the bacteria for 2.5 hours at 37° C. prior to incubating with gentamicin 100 µg/ml for 0.5 hours 37° C. The gentamicin-containing medium was then washed away, and replaced with fresh medium without or with GFZ 100 µg/ml. Intracellular multiplication was measured by lysing the monolayers, and titering the combined lysate and supernatant at the times indicated. Each point is the average (+/-) the SEM of three separate cultures. This experiment is representative of three such experiments.
Figure 6:
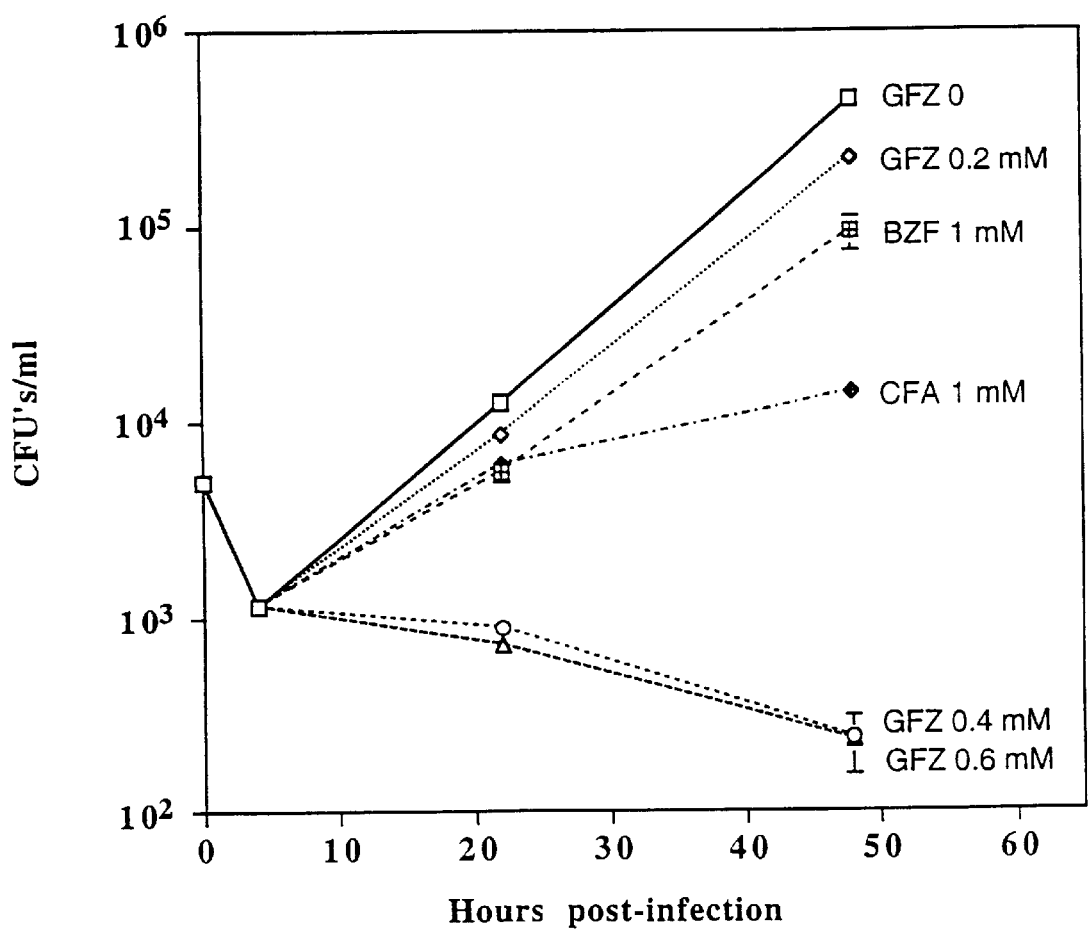
FIG. 6. GFZ inhibits L. pneumophila growth within human monocyte-derived macrophages. Human blood monocytes, maintained in culture for five days, were suspended in fresh medium and infected with L. pneumophila at a MOI of 0.01. 100 µl of the infection mixture was aliquoted to the wells of a 96 well plate, pelleted at 220 g and 880 g to pellet the bacteria and macrophages, and incubated for 2.5 hr at 37° C. to allow the cells to internalize the bacteria. 100 µl of fresh medium containing 2× the final drug concentration was then added to each well, and incubated at 37° C. At the indicated times, the cells and medium were harvested and assayed for L. pneumorhila CFUs. GFZ= gemfibrozil; BZF=bezafibrate; CFA=clofibrate. Each point represents the average of 3 wells (+/-) the SEM. This experiment is representative of three.
Figure 12:
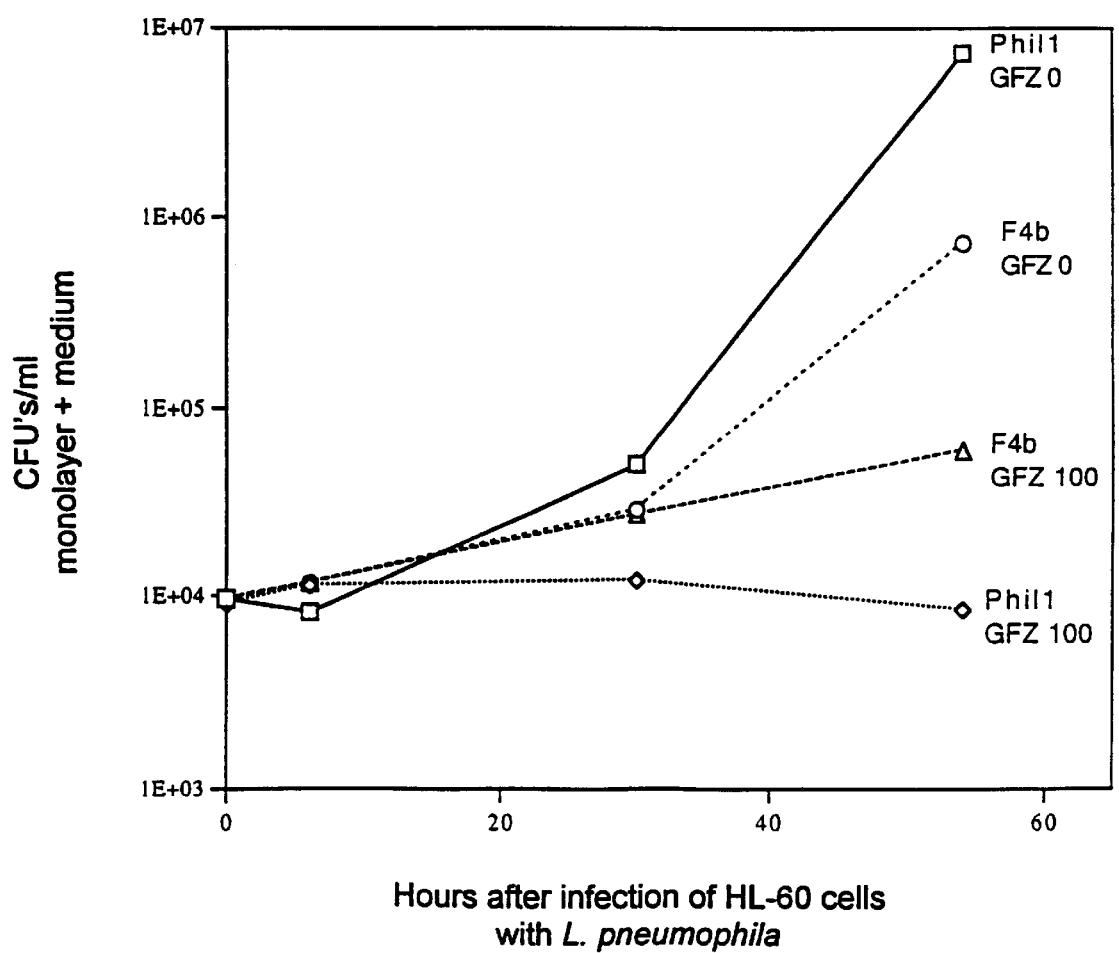
FIG. 12. F4b has increased resistance to GFZ in an HL-60 intracellular infection assay. HL-60 cells were differentiated into macrophages with PMA, plated as a monolayer in the wells of a microtiter plate, and synchronously infected with L. pneumophila F4b or L. pneumophila Philadelphia 1 (final multiplicity of infection of 0.01). After 2 hrs, the cells were washed to remove non-phagocytosed and non-adherent bacteria, overlaid with fresh RPMI-2 mM GLN-10% N corresponding propyl esters were formed by hydrochloric acid propanolysis. The amount of 3-HB in each *L. pneumophila* sample was cal autoradiography of TLC plates. By autoradiography, $^{14}$C-acetate incorporation into the various lipid species appeared equally inhibited at every GFZ concentration tested. Lane 1: GFZ 0 μg/ml; Lane 2 GFZ 10 μg/ml; Lane 3 GFZ 25 μg/ml; Lane 4 GFZ 50 μg/ml; Lane 5 GFZ 100 μg/ml. Liquid scintillation counting of duplicate samples indicated that 50% inhibition, relative to the control, was achieved at a GFZ concentration of 10 μg/ml, or 40 uM. This experiment was performed only once. It is consistent with the TCA precipitation results reported earlier in FIG. 21.
Figure 14:
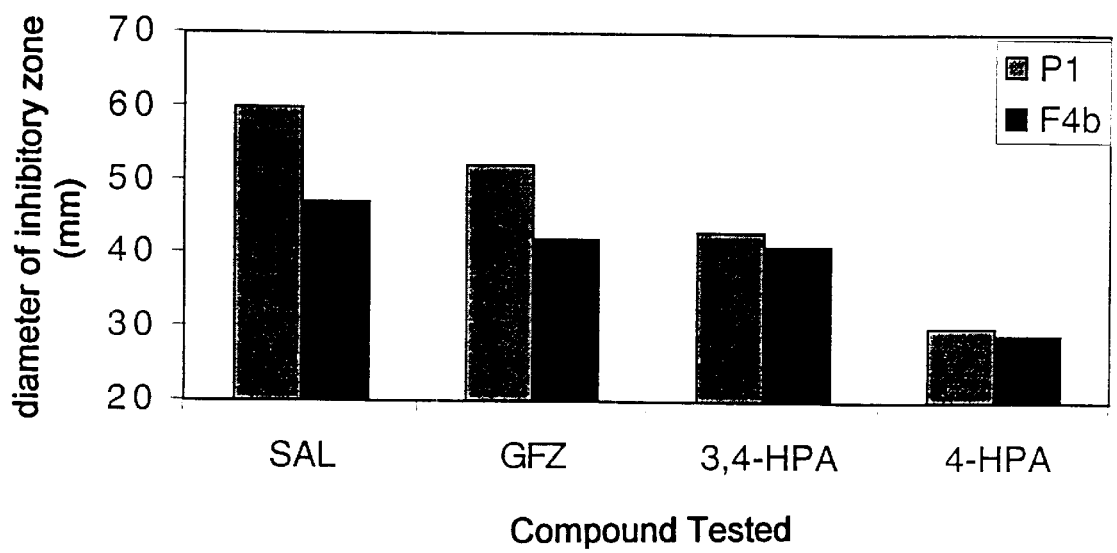
Figure 17:
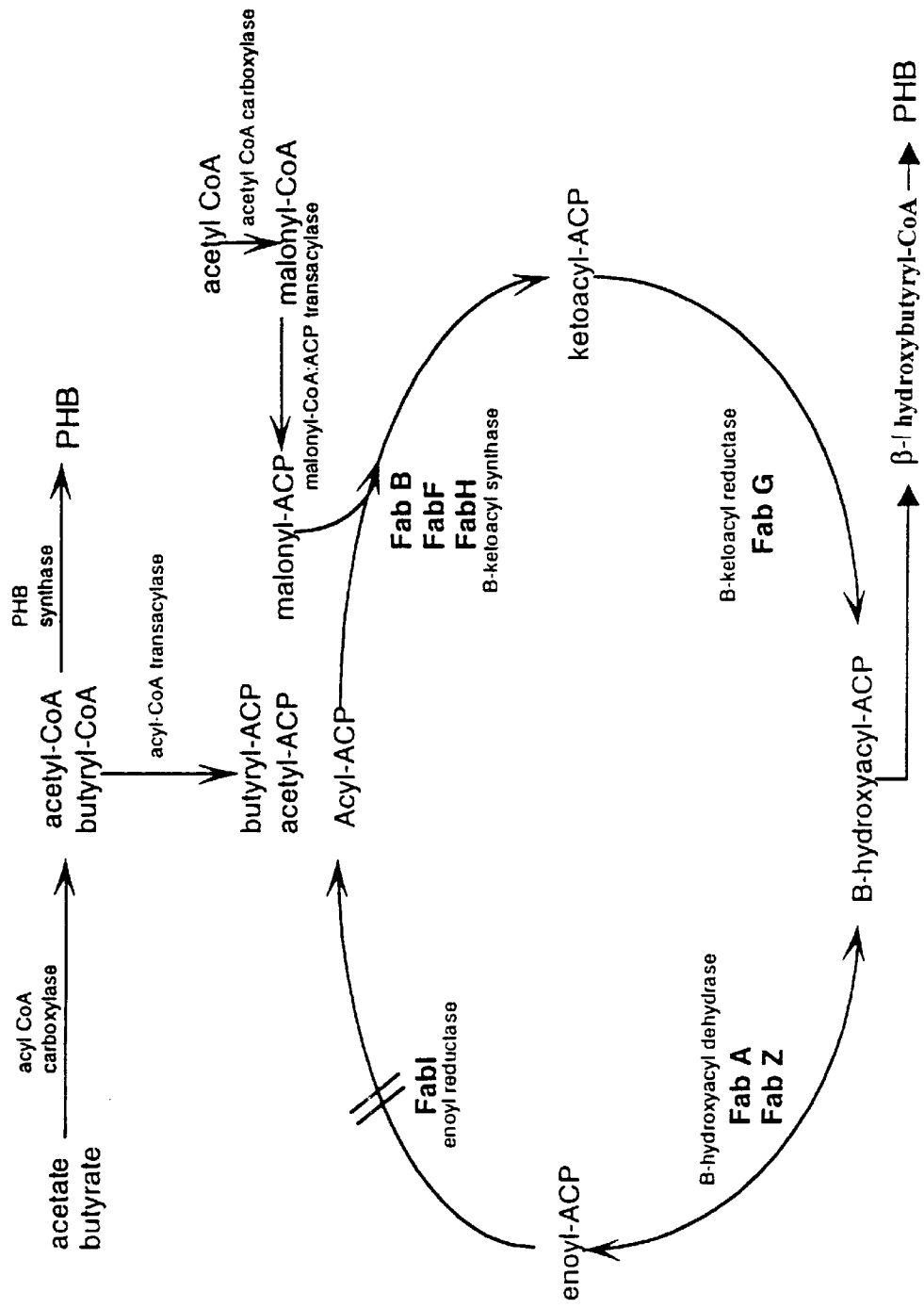
Figure 18:
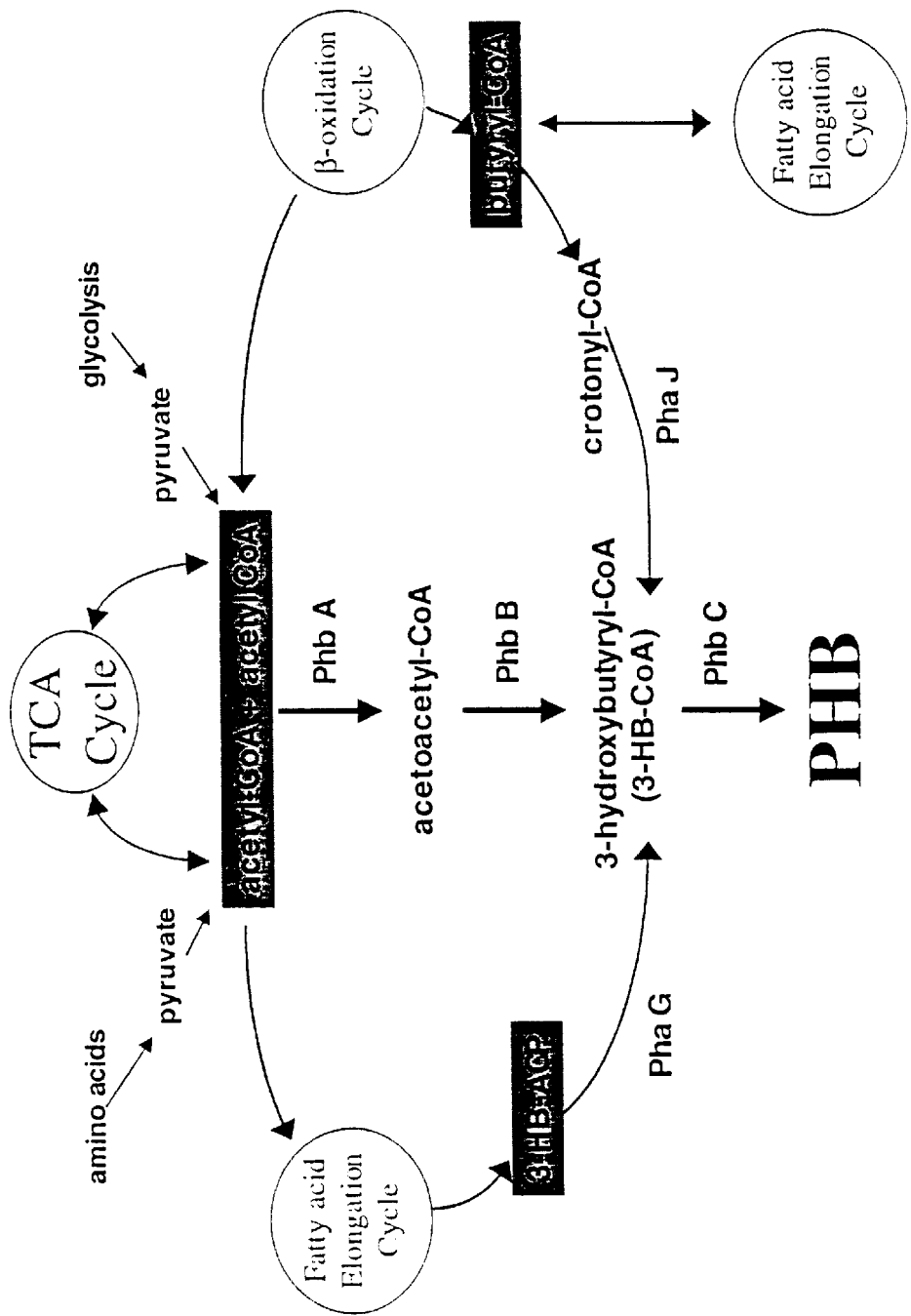

FIGS. 44A–D. Summary of the HPLC data from FPLC fraction #45. Filtered lysates of *L. pneumophila* incubated with $^3$H-GFZ for the indicated length of time were applied to an FPLC column and fractions were collected. Fraction #45 from the second peak to elute from the FPLC column was applied to a reverse phase HPLC column and fractions were collected and assessed by liquid scintillation spectrometry. Fractions collected from 3–4 minutes (fractions #6–8) contained radioactivity and co-chromatographed with the breakdown product in the 3H-GFZ stock as determined earlier (FIGS. 8–5). Fractions collected from 12.5–15 minutes (fractions #25–30) also contained radioactivity and co-chromatographed with GFZ as determined earlier. a) T=5 min; b) T=30 min c) T=60 min; d) T=180 min.

FIGS. 45A–D. Summary of the HPLC data from FPLC fraction #38. Filtered lysates of *L. pneumophila* incubated with $^3$H-GFZ for the indicated length of time were applied to an FPLC column and fractions were collected. Fraction #38 from the first peak to elute was applied to a reverse phase HPLC column and fractions were collected and assessed by liquid scintillation counting. Fractions collected from 3–4 minutes (fractions #6–8) contained radioactivity and co-chromatographed with the contaminant in the $^3$H-GFZ preparation as determined earlier (FIG. 42). Fractions collected from 12.5–15 minutes (fractions #25–30) contained radioactivity and co-chromatographed with GFZ as determined earlier. Fractions collected from 6–8 minutes (fractions #12–16) contained radioactivity and co-chromatographed with GFZ-CoA as determined earlier. a) T=5 min; b) T=30 min c) T=60 min; d) T=180 min.

Figure 46:
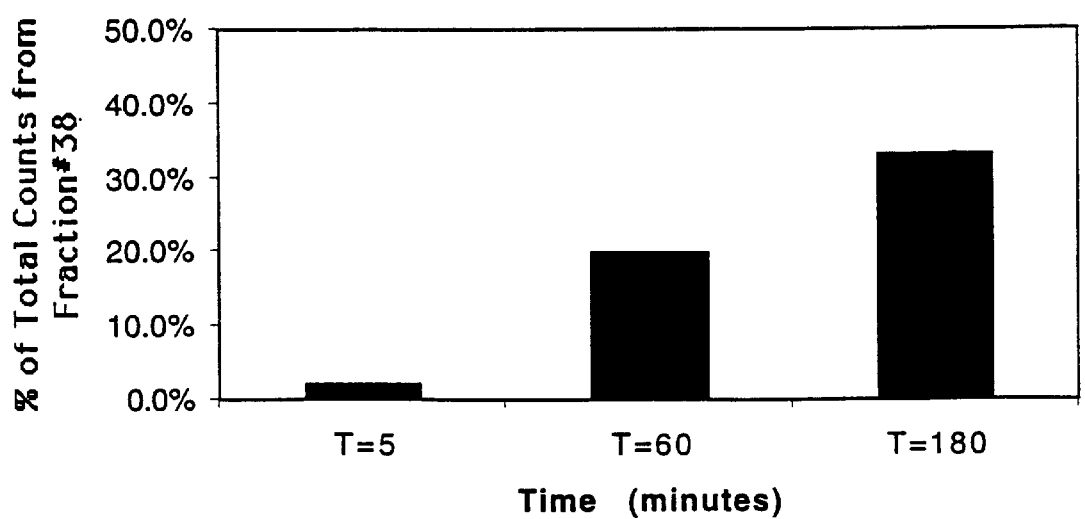

FIG. 46. Percentage of CPMs in the putative $^3$H-GFZ-CoA peak, relative to total CPMs for each sample, increases as the incubation period of *L. pneumophila* with $^3$H-GFZ increases.

DETAILED DESCRIPTION OF THE INVENTION

The present invention provides for a method of inhibiting activity of an enoyl reductase enzyme in a cell which comprises contacting the cell with a compound having the structure:

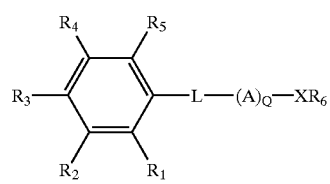

wherein each of $R_1$, $R_2$, $R_3$, $R_4$, $R_5$ and $R_6$ is independently selected from the group consisting of: —H, —F, —Cl, —Br, —I, —OH, —$OR_7$, —CN, —$COR_7$, —$SR_7$, —$N(R_7)_2$, —$NR_7$ —$COR_8$, —$NO_2$, —$(CH_2)_p$ —OR, —COSR$_7$, —COOH, —CONH$_2$, —NH$_2$, a straight chain or branched, substituted or unsubstituted C$_1$–C$_{10}$ alkyl, C$_2$–C$_{10}$ alkenyl, C$_2$–C$_{10}$ alkynyl, C$_3$–C$_{10}$ cycloalkyl, C$_3$–C$_{10}$ cycloalkenyl, thioalkyl, methylene thioalkyl, acyl, phenyl, substituted phenyl, or heteroaryl;

wherein L is alternatively —N—, —S—, —O— or —C—, wherein R$_7$ is independently selected from the group consisting of —H, —F, —Cl, —Br, —I, —OH, —CN, —COH, —SH$_2$, —NH$_2$, —NHCOH, —(CH$_2$)$_p$OH, a straight chain or branched, substituted or unsubstituted C$_1$–C$_{10}$ alkyl, C$_2$–C$_{10}$ alkenyl, C$_2$–C$_{10}$ alkynyl, C$_3$–C$_{10}$ cycloalkyl, C$_3$–C$_{10}$ cycloalkenyl, thioalkyl, methylene thioalkyl, acyl, phenyl, substituted phenyl, or heteroaryl;

wherein A is selected from the group consisting of —N$_2$—, —NH—, —C=C=CH$_2$—, —C≡C—C$_2$HOH—, —C≡C—CH$_2$—, —CH$_2$—CH$_2$—O—, —CH$_2$—CH$_2$—CH$_2$—O—, —S—, —S (=O)$_2$—, C=O—, —C=O—O—, —NH—C=O—, —C=O—NH—;

wherein Q is independently an integer from 1 to 10, or if Q is 1, A may be a (C$_1$–C$_{10}$)-alkyl chain, (C$_1$–C$_{10}$)-alkenyl chain or (C$_1$–C$_{10}$)-alkynyl chain which is branched or unbranched, substituted or unsubstituted and is optionally interrupted 1 to 3 times by —O— or —S— or —N—;

wherein X is —CO$_2$—, —CH=CH$_3$, phenyl, substituted phenyl, or heteroaryl, —O-phenyl(CH$_3$)$_2$—C(CH$_2$)$_2$—CO—NH$_2$, —C(CH$_2$)$_2$—COOH;

or a pharmaceutically acceptable salt or ester thereof, which compound is present in a concentration effective to inhibit activity of the enzyme.

In one embodiment, A is selected from the group consisting of (C$_1$–C$_{10}$)-alkylene chain, (C$_1$–C$_{10}$)-alkyl chain, (C$_1$–C$_{10}$)-alkenyl chain or (C$_1$–C$_{10}$)-alkynyl chain which is branched or unbranched, substituted or unsubstituted and is optionally interrupted 1 to 3 times by —O— or —S— or —N—.

In another embodiment of the present invention

R$_1$=R$_4$=CH$_3$ or —OH,

R$_2$=R$_3$=R$_5$=R$_6$=H or —OH,

A=CH$_2$, and Q=3.

In another embodiment of the present invention,

R$_3$=Cl,

R$_1$=R$_2$=R$_4$=R$_5$=R$_6$=H or —OH, and Q=0.

In another embodiment of the present invention, $$R_3 = -\overset{\overset{O}{\|}}{C}-\underset{}{\text{phenyl}}-CH_3$$

R$_6$=CH(CH$_3$)$_2$,

R$_1$=R$_2$=R$_4$=R$_5$=H or —OH, and Q=0.

In another embodiment of the present invention,

R$_3$=Cl,

R$_6$=C$_2$H$_5$,

R$_1$=R$_2$=R$_4$=R$_5$=H or —OH, and Q=0.

In another embodiment, the enzyme is in a bacterium or the enzyme is in an eukaryotic cell. In one embodiment, the cell is a yeast cell, the cell is a fungus, the cell is a plant cell, or the cell is a protozoan cell.

In one embodiment, the concentration of the compound or the metabolite thereof is from about 5 µg/ml to about 200 µg/ml. In a preferred embodiment, the concentration of the compound is 100 µg/ml. In another preferred embodiment, the compound is administered at a concentration of 150 micrograms/ml/kg body weight.

The present invention also provides for a method of selecting a compound which inhibits the enzymatic activity of enoyl reductase which comprises: (A) contacting enoyl reductase with the compound or a metabolite thereof; (B) measuring the enzymatic activity of the enoyl reductase of step (A) compared with the enzymatic activity of enoyl reductase in the absence of the compound or the metabolite thereof, thereby selecting a compound or metabolite thereof which inhibits the enzymatic activity of enoyl reductase.

In one embodiment, the metabolite is a CoA metabolite. In another embodiment, the metabolite is an ACP metabolite. One of skill in the art would know of other metabolites which would be produced or generated during the fatty acid synthetic pathway.

The present invention provides a method of selecting a compound which inhibits the enzymatic activity of enoyl reductase which comprises: (A) contacting enoyl reductase with the compound or metabolite thereof, wherein the compound or metabolite thereof contacts enoyl reductase at the site at which gemfibrozil contacts enoyl reductase;(B) measuring the enzymatic activity of the enoyl reductase of step (A) compared with the enzymatic activity of enoyl reductase in the absence of the compound or metabolite thereof, thereby selecting a compound which inhibits the enzymatic activity of enoyl reductase.

The present invention also provides for a method for inhibiting growth of a bacterium which consists essentially of contacting the bacterium with a compound having the structure:

wherein each of R$_1$, R$_2$, R$_3$, R$_4$, R$_5$ and R$_6$ is independently selected from the group consisting of: —H, —F, —Cl, —Br, —I, —OH, —OR$_7$, —CN, —COR$_7$, —SR$_7$, —N(R$_7$)$_2$, —NR$_7$—COR$_8$, —NO$_2$, —(CH$_2$)$_p$—OR, —COSR$_7$, —COOH, —CONH$_2$, —NH$_2$, a straight chain or branched, substituted or unsubstituted C$_1$–C$_{10}$ alkyl, C$_2$–C$_{10}$ alkenyl, C$_2$–C$_{10}$ alkynyl, C$_3$–C$_{10}$ cycloalkyl, C$_3$–C$_{10}$ cycloalkenyl, thioalkyl, methylene thioalkyl, acyl, phenyl, substituted phenyl, or heteroaryl;

wherein L is alternatively —N—, —S—, —O— or —C—;

wherein R$_7$ is independently selected from the group consisting of —H, —F, —Cl, —Br, —I, —OH, —CN, —COH, —SH$_2$, —NH$_2$, —NHCOH, —(CH$_2$)$_p$OH, a straight chain or branched, substituted or unsubstituted C–C$_{10}$ alkyl, C$_2$–C$_{10}$ alkenyl, C$_2$–C$_{10}$ alkynyl, C$_3$–C$_{10}$ cycloalkyl, C$_3$–C$_{10}$ cycloalkenyl, thioalkyl, methylene thioalkyl, acyl, phenyl, substituted phenyl, or heteroaryl;

wherein A is selected from the group consisting of —$N_2$—, —NH—, —C=C=$CH_2$—, —C≡C—$C_2$HOH—, —C≡C—$CH_2$—, —$CH_2$—$CH_2$—O—, —$CH_2$—$CH_2$—$CH_2$—O—, —S—, —S(=O)$_2$—, —C=O—, —C=O—O—, —NH—C=O—, —C=O—NH—;

wherein Q is independently an integer from 1 to 10, or if Q is 1, A may be a ($C_1$–$C_{10}$)-alkyl chain, ($C_1$–$C_{10}$)-alkenyl chain or ($C_1$–$C_{10}$)-alkynyl chain which is branched or unbranched, substituted or unsubstituted and is optionally interrupted 1 to 3 times by —O— or —S— or —N—;

wherein X is —$CO_2$—, —CH=$CH_3$, phenyl, substituted phenyl, or heteroaryl, —O-phenyl($CH_3$)$_2$, —C($CH_2$)$_2$—CO—$NH_2$, —C($CH_2$)$_2$—COOH;

or a pharmaceutically acceptable salt or ester thereof, which compound is present in a concentration effective to inhibit growth of the bacterium.

In one embodiment, A is selected from the group consisting of ($C_1$–$C_{10}$)-alkylene chain, ($C_1$–$C_{10}$)-alkyl chain, ($C_1$–$C_{10}$)-alkenyl chain or ($C_1$–$C_{10}$)-alkynyl chain which is branched or unbranched, substituted or unsubstituted and is optionally interrupted 1 to 3 times by —O— or —S— or —N—.

In one embodiment of the present invention, the bacterium is *Legionella pneumophila*. In another embodiment, the bacterium is Nocardia sp. In straight chain or branched, substituted or unsubstituted $C_1$–$C_{10}$ alkyl, $C_2$–$C_{10}$ alkenyl, $C_2$–$C_{10}$ alkynyl, $C_3$–$C_{10}$ cycloalkyl, $C_3$–$C_{10}$ cycloalkenyl, thioalkyl, methylene thioalkyl, acyl, phenyl, substituted phenyl, or heteroaryl;

wherein A is selected from the group consisting of —$N_2$—, —NH—, —C=C=$CH_2$—, —C≡C—$C_2$HOH—, —C≡C—$CH_2$—, —$CH_2$—$CH_2$—O—, —$CH_2$—$CH_2$—$CH_2$—O—, —S—, —S(=O)$_2$—, —C=O—, —C=O—O—, —NH—C=O—, —C=O—NH—;

wherein Q is independently an integer from 1 to 10, or if Q is 1, A may be a ($C_1$–$C_{10}$)-alkyl chain, ($C_1$–$C_{10}$)-alkenyl chain or ($C_1$–$C_{10}$)-alkynyl chain which is branched or unbranched, substituted or unsubstituted and is optionally interrupted 1 to 3 times by —O— or —S— or —N—;

wherein X is —$CO_2$—, —CH=CH, phenyl, substituted phenyl, or heteroaryl, —O-phenyl($CH_3$)$_2$, —C($CH_2$)$_2$—CO—$NH_2$, —C($CH_2$)$_2$—COOH;

or a pharmaceutically acceptable salt or ester thereof, which compound is present in a concentration effective to alter the pathway of fatty acid synthesis in the bacterium.

In one embodiment, the compound has the structure:

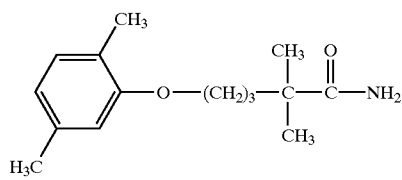

In another embodiment, the compound has the structure:

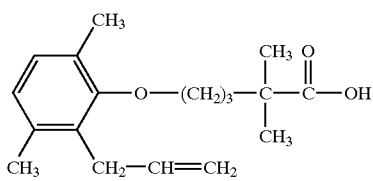

In another embodiment, the compound has the structure:

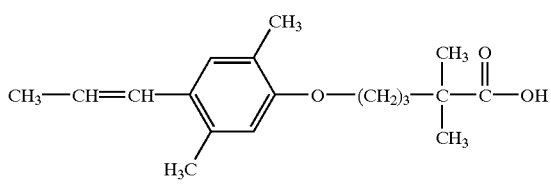

In another embodiment, the compound has the structure:

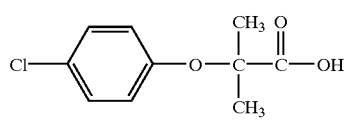

The present invention provides for a method of inhibiting activity of an enoyl reductase enzyme in a cell which comprises contacting the cell with a compound having the structure:

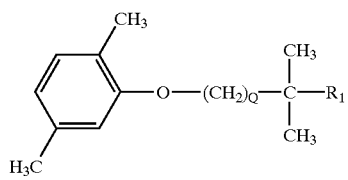

wherein $R_2$ is selected from the group consisting of: —H, —F, —Cl, —Br, —I, —OH, —$OR_7$, —CN, —$COR_7$, —$SR_7$, —N($R_7$)$_2$, —$NR_7$—$COR_9$, —$NO_2$, —$(CH_2)_p$—$OR_7$, —$COSR_7$, —COOH, —$CONH_2$, —$NH_2$, a straight chain or branched, substituted or unsubstituted $C_1$–$C_{10}$ alkyl, $C_2$$C_{10}$ alkenyl, $C_2$–$C_{10}$ alkynyl, $C_3$–$C_{10}$ cycloalkyl, $C_3C_{10}$ cycloalkenyl, thioalkyl, methylene thioalkyl, acyl, phenyl, substituted phenyl, or heteroaryl;

wherein Q is independently an integer from 1 to 10;

wherein $R_7$ is independently selected from the group consisting of —H, —F, —Cl, —Br, —I, —OH, —CN, —COH, —$SH_2$, —$NH_3$, —NHCOH, —$(CH_2)_p$OH, a straight chain or branched, substituted or unsubstituted $C_1$–$C_{10}$ alkyl, $C_2$–$C_{10}$ alkenyl, $C_2$–$C_{10}$ alkynyl, $C_3$–$C_{10}$ cycloalkyl, $C_3$–$C_{10}$ cycloalkenyl, thioalkyl, methylene thioalkyl, acyl, phenyl, substituted phenyl, or heteroaryl;

or a pharmaceutically acceptable salt or ester thereof, which compound is present in a concentration effective to inhibit enoyl reductase enzyme in the cell.

The method also includes use of a pharmaceutically acceptable salt or ester thereof, which compound is present in a concentration effective to inhibit bacterial growth and thus alleviate the symptoms of the bacterial infection in the subject.

The present invention also provides for a pharmaceutical composition comprising a compound or metabolite thereof having any one of the structures shown or described hereinabove and a pharmaceutically acceptable carrier.

The bacterial infection may be associated with a bacterium listed above. The subject may be a human or an animal. The bacterial infection may be associated with Leprosy, Brucella or Salmonella. The concentration of the compound may be from about 5 μg/ml blood of the subject to about 200 μg/ml blood of the subject. In one embodiment, the concentration of the compound may be 100 μg/ml blood of the subject. The administration to the subject may be oral.

As used herein Enoyl Reductase Enzyme includes enzymes having enoyl reductase activity. Such enzymes may be bacterial enoyl reductases or eukaryotic enoyl reductases. Examples of bacterial enoyl reductases include those from the bacterium listed above. The enoyl reductase may be one of the enoyl reductases from *L. pneumophila*. The enoyl reductase may be a gene product of a gene that hybridizes with moderate or high stringency with the envM gene.

The enzyme may be in a bacterium. The bacterium may be *Legionella pneumophila, Mycobacterium tuberculosis, Bacillus subtilis, Bacillus megaterium, Pseudomonas oleovorans, Alcaligenes eutrophus*, Rhodococcus sp., *Citrobacter freundi*, Group A Streptococcus sp., Coag neg *Staphylococcus aureus* or Nocardia sp. The bacterium may be *Legionella pneumophila*. The bacterium may be *Mycobacterium tuberculosis*. The enzyme may be in a cell. The cell may be a mammalian cell.

The present invention provides for a method of selecting a compound which is capable of inhibiting the enzymatic activity of enoyl reductase which includes:(A) contacting enoyl reductase with the compound; (B) measuring the enzymatic activity of the enoyl reductase of step (A) compared with the enzymatic activity of enoyl reductase in the absence of the compound, thereby selecting a compound which is capable of inhibiting the enzymatic activity of enoyl reductase. The compound may contact enoyl reductase at same site at which gemfibrozil contacts enoyl reductase. U.S. Pat. No. 5,422,372 discloses a method of increasing intracellular accumulation of hydrophilic anionic agents using gemfibrizol (gemfibrozil). U.S. Pat. No. 4,859,703 discloses lipid regulating compositions. U.S. Pat. No. 4,891,220 discloses a method and composition for treating hyperlipidemia. The disclosures of these publications in their entireties are hereby incorporated by reference into this application in order to more fully describe the state of the art as known to those skilled therein as of the date of the invention described and claimed herein.

Another embodiment of the present invention is a kit which is capable of detecting the presence of a particular organism based on the sensitivity of the organism to gemfibrozil. The present invention provides for a kit for detecting the presence of one or more organisms in a sample which comprises: (a) an agar or solution medium suitable for growth of the organism; (b) a means for testing growth of each organism in the presence and absence of gemfibrozil such that the growth of the organism or lack thereof can be detected; (c) a means for determining the growth of the organism thus detecting the presence of one or more organisms in a sample. The kit may be in form of an assay, a screening kit or a detection kit.

In one embodiment the compound of the present invention is associated with a pharmaceutical carrier which includes a pharmaceutical composition. The pharmaceutical carrier may be a liquid and the pharmaceutical composition would be in the form of a solution. In another embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

A solid carrier can include one or more substances which may also act as flavoring agents, lubricants, solubilizers, suspending agents, fillers, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including onohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The active ingredient may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The active ingredient can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like. The active ingredient can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

The emergence of multiply antibiotic-resistant bacterial pathogens (i.e. *M. tuberculosis* and *S. aureus*) has prompted the search for new or unrecognized antibiotic targets in bacteria. Most currently used antibiotics act by blocking bacterial protein, DNA or RNA synthesis, and/or cell wall assembly. However, as demonstrated by the ability of isoniazid and ethionamide to inhibit InhA [1,2], an enoyl reductase of *M. tuberculosis* [3], bacterial enzymes involved in fatty acid synthesis are also potential antibiotic targets.

While bacterial and mammalian cells use the same general pathways and mechanisms to synthesize fatty acids, bacterial fatty acid synthases differ from their mammalian counterparts in a number of respects. For example, mammalian fatty acid synthase is a type I synthase, a homodimer composed of a single polypeptide encoding seven distinct enzymatic functions. Type I synthases perform all of the reactions required for the synthesis and elongation of fatty acids in mammals [4]. Bacterial fatty acid synthases are most commonly type II syntheses. Type II synthases are dissociated fatty acid synthase systems composed of individual proteins encoded by distinct genes. Within this system, multiple isozymes of a given protein often exist which catalyze the same basic chemical reaction but differ in substrate specificity and regulation [5].

Bacteria synthesize many fatty acids not synthesized by human cells (i.e. branched chain fatty acids, dihydroxy fatty acids). The presence of these fatty acids is hypothesized to allow bacteria to maintain membrane fluidity and function upon exposure to a variety of environmental insults including variations in temperature and osmolarity. Drugs that block synthesis of these unique bacterial fatty acids, by inhibiting bacteria-specific enzymes, may block bacterial growth without having a detrimental effect on mammalian cells. Accordingly, isoniazid and ethionamide act by inhibiting an enoyl reductase involved in the synthesis of mycolic acids, very long chain fatty acids synthesized by *M. tuberculosis*, but not by human cells.

The findings reported here indicate that gemfibrozil (GFZ), a commonly prescribed and well-tolerated hypolipidemic agent, inhibits an *L. pneumophila* enoyl reductase, and has antibiotic activity against a wider spectrum of bacteria than isoniazid. Our findings suggest that bacterial enoyl reductases may be more useful targets for novel antibiotics than previously recognized.

Differences in Bacterial and Mammalian Fatty Acid Synthesis

Bacterial fatty acid synthases differ from their mammalian counterparts in a number of respects, providing potential targets for antimicrobial therapy. For example, human or mammalian fatty acid synthase (FAS) is a Type I synthase. In general, Type I synthases are multifunctional proteins which perform all or many of the reactions required for the synthesis and elongation of fatty acids in mammals [4]. In contrast, bacterial FAS are most commonly Type II. Type II synthases are dissociated systems composed of individual proteins encoded by distinct genes. Within this system, multiple isozymes of a given protein often exist which catalyze the same basic chemical reaction but differ in substrate specificity and regulation [5].

Not surprisingly, the products synthesized by bacterial Type II synthases are more varied and complex than those synthesized by mammalian Type I syntheses. The end products of Type I mammalian fatty acid synthases are generally palmitate, a sixteen carbon saturated fatty acid ($C_{16:0}$) myristate ($C_{14:0}$), and laurate ($C_{12:0}$). In contrast, bacterial Type II FAS systems synthesize a complex assortment of fatty acids the profiles of which can differ greatly among species of bacteria (FIG. 1). The synthesis of these fatty acids is hypothesized to allow bacteria to maintain constant membrane fluidity and function upon exposure to a variety of environmental pressures including variations in temperature and osmolarity.

The bacterial enzymes involved in the synthesis of these specialized fatty acids generally perform the same basic reactions as those performed by mammalian fatty acid synthases, but have widely different substrate specificities and regulatory characteristics. However, there are some enzymatic functions which are specific to bacteria including the formation of unsaturated fatty acids during elongation, and the formation of cyclopropyl, hydroxylated, and ω-alicyclic fatty acids [8]. Drugs that block the synthesis of unique bacterial fatty acids by inhibiting the utilization of bacteria-specific substrates or bacteria-specific enzymes, may block bacterial growth without having a detrimental effect on mammalian cells. Accordingly, the clinically effective and prescribed drugs isoniazid and ethionamide act by inhibiting an enoyl reductase involved In the synthesis of mycolic acids, very long chain fatty acids which are synthesized by *M. tuberculosis*, but not by human nest cells [1].

Fatty Acid Synthesis in Bacteria

Both bacteria and mammalian cells utilize acetyl-CoA as the building block for fatty acid synthesis. Bacteria acquire acetyl-CoA from the decarboxylation of pyruvate when grown on sugars, and from β-oxidation when grown on fatty acids. In mammalian cells, acetyl-CoA is derived largely from the tricarboxylic acid (TCA) cycle. High concentrations of ATP and NADH in the mitochondria inhibit the TCA enzyme isocitrate dehydrogenase resulting in the accumulation of citrate. Citrate diffuses from the mitochondrion into the cytosol where it is converted to acetyl-CoA and then to malonyl-CoA for fatty acid elongation, or to acetyl-ACP for the initiation of fatty acid synthesis.

In *E. coli*, the initiation or elongation of straight chain fatty acid synthesis can occur through three different condensation reactions; condensation of an acetyl-CoA with malonyl-ACP, condensation of acyl-ACP with malonyl-ACP, and the decarboxylation of malonyl-ACP to acetyl-ACP followed by condensation with malonyl-ACP. All three condensation reactions form acetoacetyl-ACP (FIG. 2) [5]. The condensation step is the only irreversible step in fatty acid synthesis in Type II systems. *E. coli* has three different β-ketoacyl synthases with overlapping substrate specificities. However, β-ketoacyl synthase I [9] catalyzes an essential step in unsaturated fatty acid metabolism, that cannot be catalyzed by the other two syntheses. β-ketoacyl synthase II [10] is involved in the thermal regulation of fatty acid composition, and β-ketoacyl synthase III [11] catalyzes the initial condensation reaction in the pathway. in mammalian cells, straight chain fatty acid synthesis is initiated through the condensation of acetyl-ACP and malonyl-CoA by the β-ketoacyl synthase domain of the fatty acid synthase enzyme.

β-ketoacyl synthase activity also mediates the synthesis of branched chain fatty acids by the condensation of branched chain precursors with malonyl-CoA at the initiation step of fatty acid synthesis. The primer sources for the branched chain fatty acids are generally 2-keto-acids derived from the branched chain amino acids, valine, leucine, and isoleucine [12,13]. Branched chain fatty acids are synthesized by many species of bacteria and by the sebaceous glands of mammalian skin.

The next step in both straight and branched chain fatty acid elongation involves the reduction of the β-ketoacyl-ACP by β-ketoacyl-ACP reductase to a β-hydroxybutyryl-ACP. Dehydration by β-hydroxyacyl dehydrase yields crotonoyl-ACP. This reaction is very inefficient, and the ratio of substrate to product is generally 9:1 [14]. in *E. coli*, there are two dehydrase enzymes which can catalyze this step [15]. One is involved in the elongation of saturated fatty acids, and the other serves as the branch point for the synthesis of unsaturated fatty acids.

The final step in the fatty acid elongation cycle involves the reduction of the enoyl-ACP substrate to generate an acyl-ACP by enoyl reductase. The acyl-ACP is either the end product of fatty acid synthesis, or, serves as the starting material for subsequent cycles of fatty acid elongation. Since the concentration of the enoyl substrate is very low, enoyl reductase is thought to "pull" successive cycles forward. For this reason it is thought to be the rate-limiting enzyme in fatty acid synthesis [14].

Inhibition of phospholipid synthesis due to increased levels of the stationary phase alarmone ppGpp in bacteria, leads to the accumulation of acyl-ACPs and inhibition of fatty acid synthesis [16]. In a reconstituted fatty acid synthesis assay, the addition of palmitoyl-ACP to the reconstituted system resulted in the accumulation of malonyl ACP and 3-hydroxybutyryl-ACP (3-HB-ACP), presumably by inhibiting of enoyl reductase and β-ketoacyl synthase III. However, 3-HB-ACP accumulated first, and at higher concentrations than malonyl-ACP, indicating that enoyl was the relevant target of palmitoyl-ACP's inhibitory effect [17].

The accumulation of long chain acyl-CoAs occurs during bacterial growth in the presence of long chain fatty acids. Exogenous long chain fatty acids are converted to their CoA thioesters by *E. coli*, and are either used as substrates for β-oxidation, or are preferentially incorporated into phospholipids following conversion to their ACP derivatives [18–20]. Long chain acyl-CoAs have been shown to directly inhibit enoyl reductase activity and to bind to the global transcriptional regulator FadR. The interaction of long chain acyl-CoAs (derived from oleate or palmitate) with FadR releases FadR from DNA, stimulates β-oxidation and fatty acid transport into *E. coli*, and inhibits three genes involved in fatty acid synthesis in these bacteria; fabA, β-hydroxydecenoyl dehydrase, the enzyme responsible for unsaturated fatty acid synthesis, fabb, one of three β-ketoacyl synthases, and the enoyl reductase fabI [21–24].

Inhibitors of Fatty Acid Synthesis

Several compounds that inhibit enzymes in fatty acid synthesis have been described. Cerulenin is an inhibitor of fatty acid synthesis in prokaryotes and eukaryotes that acts on β-ketoacyl synthase to inhibit the condensation of an acyl-ACP or an acetyl-CoA with malonyl-ACP [25]. However, since cerulenin inhibits both bacterial and mammalian fatty acid synthesis, it is not clinically useful as an antimicrobial, but is being pursued as a chemotherapeutic agent to treat cancers which over express FAS [26,27]. Thiolactomycin, is a specific inhibitor of Type II bacterial β-ketoacyl synthases [28] and is active against many species of Gram-positive and Gram-negative bacteria [29]. However, resistance is frequently acquired [30,31]. 3-decanoyl-N-acetylcysteamine (NAG) is an inhibitor of β-hydroxydecenoyl thioester hydrase, a bacterial enzyme catalyzing the synthesis of unsaturated fatty acids [32,33]. This compound inhibits unsaturated fatty acid synthesis in bacteria including *E. coli*, but not in mammalian cells.

Several compounds have been reported to interfere with bacterial enoyl reductase activity including isoniazid, ethionamide, triclosan and related compounds, and diazoborines Of all the compounds that inhibit enzymes in bacterial fatty acid synthesis, only two, isoniazid and ethionamide, are useful as drugs and only for the treatment of mycobacterial infections [34].

Isoniazid and ethionamide inhibit the InhA enoyl reductase enzyme of *M. tuberculosis* [1–3,35]. Mutations in InhA, at or near residues involved in NADH binding, confer resistance to these compounds [1,2] as do mutations affecting the intracellular levels of NADH [36]. Isoniazid is a prodrug. Kat G, a catalase-peroxidase enzyme of *M. tuberculosis* [37] catalyzes the formation of an activated isonicotinic acyl radical which interacts with NADH bound at the active site of the InhA enzyme [2]. The carbonyl carbon of the isonicotinic acyl group covalently attaches to the carbon at position four of the nicotinamide ring, replacing the 4S hydrogen of NADH involved in hydride transfer during the reduction of an enoyl substrate. The complex inactivates the enzyme since it displaces the side chain of Phe$^{149}$ allowing it to form an aromatic ring stacking interaction with the pyridine ring of the isonicotinic group. This conformational change increases the affinity of the complex for the enzyme, such that it is not released. Mutations which decrease the affinity of InhA for NADH may protect the enzyme by promoting the binding of acyl-ACP substrates before NADH binds. The binding of an acyl-ACP substrate does not allow the bulkier activated isonicotinic acyl radical access to the active site.

Isoniazid also has been reported to inhibit the *M. tuberculosis* fatty acid synthesis β-ketoacyl synthase enzyme, KasA. Mutations in the amino-acid sequence of the KasA protein, were identified in INH-resistant clinical strains of *M. tuberculosis* that lacked other known mutations conferring resistance to INH.

Diazoborines, another group of enoyl reductase inhibitors, exhibit antibacterial activity against most species of Gram-negative bacteria [38] by a similar but distinct mechanism to that of INH. The boron atom in diazoborine forms a covalent bond with the 2-hydroxyl oxygen of the nicotinamide ribose of NADH, generating a bi-substrate analog. The bicyclic rings of the diazoborines form a face to face interaction with the nicotinamide ring allowing extensive π—π stacking interactions. Crystallographic studies show that this bi-substrate analog binds non-covaiently, but tightly, to *E. coli* FabI enoyl reductase [39], interfering with the access of the reduced pyridine nucleotide (NADH or NADPH) to *E. coli* FabI's catalytic site. The activity of this class of compounds is dependent on the presence of the boron substituent, which is toxic for mammalian systems [38].

Triclosan, a topical antiseptic, not approved for oral administration, appears to inhibit *E. coli* enoyl reductases by a mechanism similar to the diazoborines [40,41]. The phenolic hydroxyl group forms a hydrogen bond (not covalent as for the diazoborines) with the 2-hydroxyl oxygen of the nicotinamide ribose of NADH. The phenol ring of triclosan forms a face to face interaction with the nicotinamide ring allowing extensive π—π stacking interactions. Homologous mutations in the *E. coli* fabi and *M. tuberculosis* inhA genes, confer resistance to diazoborines, triclosan, or isoniazid, consistent with a NADH-dependent mechanism of inhibition.

In conclusion, while the basic mechanisms of fatty acid synthesis between the mammalian Type I synthases and the bacterial Type II synthases are conserved, significant differences exist. These differences should be exploitable for the creation of new classes of antibiotics. The need for antibiotics that inhibit bacterial growth by mechanisms other than those used by current antibiotics is increasing as the number of bacterial species resistant to multiple drugs grows. The findings that isoniazid and ethionamide [1], the diazoborines [42], and triclosan [40] all act by inhibiting enoyl reductases suggest that this key regulatory enzyme in fatty acid biosynthesis is an excellent antimicrobial target.

GFZ INHIBITS THE GROWTH OF *LEGIONELLA PNEUMOPHILA* IN MACROPHAGES AND IN NUTRIENT BROTH

Gemfibrozil (Lopid™) is well known as a hypolipidemic agent that lowers LDL and triglyceride levels in humans. The mechanism(s) by which GFZ exerts this effect is unresolved. GFZ has also been reported to inhibit organic anion transport in mouse J774 macrophages [43]. Although the endogenous substrates for this transporter have not been identified, it is known that anionic compounds, including Lucifer Yellow, fluorescein, penicillin and the fluoroquinolone antibiotics ciprofloxacin and norfloxacin, are efficiently secreted by J774 macrophages by GFZ inhibitable transporters [43–46].

Inhibitors of anion efflux should increase the intracellular concentration of anionic antibiotics, thus increasing the efficacy of a given oral or intravenous dose for intracellular pathogens. Addition of GFZ in combination with norfloxacin, reduced by fourfold the concentration of norfloxacin required to block intracellular growth of *Listeria monocytogenes* in mouse J774 macrophage-like cells [46]. This was consistent with previous findings in which treatment of J774 cells with GFZ increased the intracellular concentration of norfloxacin in the J774 cells fourfold [44].

*L. monocytogenes* grows in the cytoplasm of macrophages, Other intracellular pathogens reside in specialized membrane-bound intracellular compartments. For such pathogens, increasing the concentration of antibiotics in the cytosol may have no effect if the concentration of the antibiotic is not increased in the pathogen-containing compartment. Alternatively, if the antibiotic readily penetrates the pathogen-containing compartment, then increases in the cytoplasmic concentration of the given antibiotics should potentiate the antimicrobial effect of the antibiotic. Since GFZ exerts the latter effect on fluoroquinolone antibiotics it was desirable to evaluate the effect cf GFZ in combination with these antibiotics against intracellular pathogens that grew within membrane-bound compartments in macrophages. We began with *Legionella pneumophila*, an intracellular pathogen responsible for up to percent of all community-acquired pneumonias requiring hospitalization [47].

*L. pneumophila* is an environmental pathogen most commonly found in water sources such as shower heads, water towers and air conditioning condensers. Aerosolization of contaminated water sources allows the bacteria to be inhaled into the lungs where it infects alveolar macrophages. *L. pneumophila* enters macrophages within phagosomes produced as a result of a process known as coiling phagocytosis }[48]. The Legionella-containing phagosomes go through a unique series of modifications such that acidification is avoided, and mitochondria, smooth vesicles, ribosomes and rough endoplasmic reticulum are recruited to their periphery [49–52]. In human macrophages, or in the macrophage-like cells of the HL-60 human myelocytic cell line, bacterial replication generally begins within eight hours of bacterial uptake [52,53]. Twenty four to thirty six hours after infection, the cells round up, undergo either bacterially induced lysis or apoptosis [53–55], and release the expanded population of intracellular bacteria for subsequent rounds of infection.

While testing the ability of GFZ to increase the efficacy of fluoroquinolone antibiotics in a *L. pneumophila* infection model, I discovered that GFZ alone inhibited the intracellular growth of *L. pneumophila* in peripheral-blood monocyte derived human macrophages and in the phorbol myristace acetate (PMA)-differentiated macrophage-like cells of the HL-60 human promyelocytic cell line. Results: Addition of GFZ to a final concentration of 0.4 mM (100 μg/ml) to the medium of PMA-differentiated HL-60 cells infected with *L. pneumophila* resulted in inhibition of *L. pneumophila* intracellular growth (FIG. 3). To determine whether growth inhibition was due to a cytotoxic effect of GFZ on the HL-60 cells, cellular viability assays were performed on uninfected and infected HL-60 cells. The MTT assay was used, which assesses cellular respiration via the reduction of a tetrazolium dye to an insoluble blue formazan in viable cells [53,56,57] to test HL-60 viability. GFZ at 100 μg/ml did not affect the viability of uninfected HL-60 cells, even when the cells were incubated or five days. Furthermore, the presence of GFZ in the medium protected infected HL-60 cells from *L. pneumophila's* cytolytic effects even at an infection multiplicity of 0.1 bacteria/cell (FIG. 4). Therefore, it was possible that GFZ was directly inhibiting the growth of *L. pneumophila.*

To assess whether GFZ had the potential to directly inhibit *L. pneumophila* growth, a minimum inhibitory concentration (MIC) assay was performed. *L. pneumophila* was added to ACES-buffered yeast extract (AYE) liquid medium containing varying concentrations of GFZ. The MIC which inhibited 90% of *L. pneumophila* growth was 10 μg/ml of GFZ. At all concentrations tested (10–200 μg/ml), GFZ was bacteriostatic for *L. pneumophila* Philadelphia 1, as determined by plating 5 pl aliquots of the MIC cultures on charcoal yeast extract (CYE) and visually assessing growth after four days of incubation at 37° C.

*L. pneumophila* does not grow in human plasma or in mammalian tissue culture medium so it was unlikely that GFZ blocked *L. pneumophila* growth by affecting extracellular bacteria. Nonetheless, a single-round growth assay was developed to confirm that GFZ had access to, and was inhibiting the growth of intracellular *L. pneumophila* within HL-60 cells. In this assay gentamicin was added to the medium two hours after *L. pneumophila* infection to kill any remaining extracellular bacteria. After a 30 minute incubation, the gentamicin-containing medium was washed away and replaced with fresh medium containing GFZ at a final concentration of 0.4 mM (100 μg/ml). Inhibition of bacterial growth was seen within 8 hours after infection, well within the 24–36 hour time period required for *L. pneumophila* to lyse these cells [50,54,55] (FIG. 5).

This experiment shows that GFZ inhibits the growth of *L. pneumophila* intracellularly. *L. pneumophila* also grows intracellularly in primary human blood monocyte-derived macrophages [54,58]. In accordance with the results found in the HL-60 cell line, GFZ at a concentration of 0.4 mM (100 μg/ml), inhibited the intracellular growth of *L. pneumophila* in human macrophages (FIG. 6). GFZ at 0.4 mM was optimal since no further reduction in *L. pneumophila* colonies was observed with GFZ 0.6 mM.

Although the previous experiments demonstrated that growth inhibition was not due to a cytotoxic effect in HL-60 cells, it was still possible that GFZ was inhibiting growth through a "fibric acid-mediated" effect on the macrophages. GFZ belongs to a class of fibric acids including clofibrate, fenoflbrate, and bezafibrate, all of which lower serum triglyceride levels though an unresolved mechanism. These analogs are also known to stimulate peroxisome proliferator activated receptors (PPARs) in rats, although this effect does not occur in humans. PPARs are transcriptional activators which affect genes in several metabolic pathways including cholesterol biosynthesis [59–61] and the β-oxidation of fatty acids [62,63].

To test whether GFZ inhibition of intracellular *L. pneumophila* growth occurred through a fibric acid mediated effect on host cell gene expression, other fibric acids were examined (FIG. 6). When bezafibrate was added to human macrophages infected with *L. pneumophila* at a concentration of 1 mM, no inhibition of *L. pneumophila* growth was observed. Clofibrate, another structural analog of GFZ FIG. 7), was able to slow *L. pneumophila* growth although a concentration of 1 mM was required. Fenofibrate precipitated out of solution at a concentration of 0.1 mM, so it was not studied in this system. The ability of these fibric acids to inhibit *L. pneumophila* growth in AYE broth was assessed by MIC assays. While GFZ has an MIC of 10 μg/ml, clofibrate was found to have an MIC of 100 μg/ml, and bezafibrate an MIC of 250 μg/ml. Fenofibrate precipitated out of solution at a concentrations above 100 μg/ml, and did not inhibit *L. pneumophila* growth at this concentration.

This is the first report of GFZ's antibiotic activity. It was highly surprising and serendipitous to find that a compound used safely in man for over twenty years to lower triglycerides, inhibited bacterial growth. This suggested zhat GFZ might be inhibiting a bacterial target which is not expressed in humans or is resistant to GFZ in humans.

The mechanism by which GFZ exerts its hypolipidemic effect is unknown. At least seven different pathways in lipid metabolism have been shown to be affected by GFZ, either in vivo or in cell culture. The seven pathways affected by GFZ are: 1) GFZ stimulates lipoprotein lipase activity, cleaving fatty acids from triglycerides In the VLDL fraction of the plasma; 2) GFZ increases the activity of lipoprotein lipase [61,64]; 3) GFZ stimulates intracellular triglyceride synthesis [65] possibly mediated through an increase in acyl-CoA synthetase expression [66]; 4) GFZ promotes the transcription of several enzymes involved in the β-oxidation of fatty acids through the stimulation of peroxisome proliferator activated receptors (PPARs), although peroxisome proliferation has only been demonstrated in rats [62,63]; 5) GFZ decreases microsomal fatty acid elongation [67,68]; 6) GFZ stimulates the synthesis of Apo A-1, the major protein in HDL [59,69] and 7) GFZ decreases the synthesis of cholesterol [60]. Any or all of these mechanisms could be involved in lowering serum lipids.

Although GFZ inhibits intracellular *L. pneumophila* growth within macrophages, the concentration required to inhibit growth within these cells (100 μg/ml) is ten-fold higher than that required to inhibit growth in AYE broth (10 μg/ml). The finding that a lower concentration of an antibiotic is required to inhibit extracellular versus intracellular growth of a bacterial pathogen is not uncommon. Other antibiotics which inhibit *L. pneumophila* growth, both extracellularly and intracellularly are erythromycin, doxycycline, and rifampin. All three of these antibiotics inhibit extracellular growth of *L. pneumophila* at lower concentrations than intracellular growth (e.g. erythromycin at 0.2 μg/ml versus 1.25 μg/ml, doxycycline at 0.4 μg/ml versus 0.8 μg/ml, and rifampin at 0.002 μg/ml versus 0.1 μg/ml [70–73]. For an antibiotic to inhibit the intracellular growth of a bacterial pathogen, it must enter the host cell, enter the compartment that contains the pathogen, and be retained within that compartment in an active form [74].

Therefore, with respect to *L. pneumophila*, several explanations could account for the difference in MICs. First, in work not described here, the addition of 10% serum to AYE increased GFZ's MIC from 10 μg/ml to 30 μg/ml, suggesting that serum contains factors capable of binding GFZ, thereby reducing its effective concentration. Charcoal is known to have a similar effect such that the MICs of antibiotics for *L. pneumophila* on ACES-buffered charcoal yeast extract (ABCYE) agar [75], range from two to twenty fold higher than the MIC values found on buffered potato starch yeast extract (BSYE) agar. The latter contains potato starch instead of charcoal [76]. Second, GFZ may be transported out of the host cell cytoplasm, or, out of the ribosome-studded compartment in which *L. pneumophila* grows, thus limiting the amount available to inhibit intracellular *L. pneumophila*. Third, the host cell may metabolize GFZ to either a less active compound, or, a compound that has limited access to the *L. pneumophila*-containing compartment. Fourth, *L. pneumophila* may be more resistant to GFZ when growing intracellularly. Barker et al. reported that intracellular growth enhances resistance to antibiotics in *L. pneumophila* [77]. Fifth, metabolites provided by the host cell may reduce GFZ's inhibitory effect.

We draw several conclusions from these experiments. First, a fibric acid mediated effect on host cell transcription is not likely to be the cause of GFZ's ability to inhibit the intracellular growth of *L. pneumophila* since bezafibrate was totally ineffective and clofibrate much less effective than GFZ at inhibiting intracellular growth (FIG. 6). Second, the ability of GFZ to inhibit the growth of *L. pneumophila* in AYE broth at a concentration of 10 μg/ml demonstrates that GFZ has a direct inhibitory effect on *L. pneumophila*. The ability of GFZ to inhibit intracellular growth strongly suggests that GFZ has access to the unique intracellular compartment in which *L. pneumophila* resides. Further work with $^3$H-GFZ is required to confirm this suggestion. Third, metabolites provided by the macrophages do not circumvent the capacity of GFZ to inhibit the intracellular growth of *L. pneumophila.*

While many potential antibiotics are often highly effective against pathogens in laboratory conditions, they often fail in animal infection models and/or clinical trials due to unexpected toxicity, or a lack of effect, in a mammalian host. Since GFZ has been used therapeutically for years, there is a large body of literature confirming its safety, even at much higher levels that those used to treat hyperlipidemia [78,79].

In humans, GFZ is reported to achieve a serum concentration of 12–15 μg/ml within 2 hours following a single oral dose of 450–600 mg [78,79]. These levels were sustained for an additional four hours, but fell to 5 μg/ml by 9 hours after administration [78–81]. Although the MIC (10 μg/ml) for *L. pneumophila* in nutrient broth is within the serum levels achieved for the treatment of hypertriglyceridemia, a concentration of 100 μg/ml was required to inhibit intracellular *L. pneumophila* growth. However, plasma drug levels are proportional to the dose [82], so a serum GFZ concentration of 100 μg/ml could be achieved through higher dosage. A serum concentration of 100 μg/ml in mice would only require 3.24 mg/mouse per day (1.08 mg every eight hours) well below the $LD_{50}$ of 250 mg/20 gm mouse per day for mice [78,79].

In summary, these experiments revealed that GFZ is inhibitory for *L. pneumophila* growth in AYE broth and within macrophages. This finding has relevance for the use of GFZ to treat bacterial infection in humans since GFZ is known to have relatively low toxicity in humans, even with long term use as a therapeutic agent for hypertriglyceridemia. Further studies are needed to assess the potential therapeutic use of GFZ, or related analogs, in the treatment of human bacterial infections.

METHODS AND MATERIALS

Bacterial and Growth Conditions. *L. pneumophilia* Philadelphia 1 serogroup 1 was a generous gift from Dr. Marcus Horowitz [83]. *L. pneumophola* was grown in ACES-buffered yeast extract (AYE) broth [71] that lacked bovine serum albumin at 37° C. with aeration, or, on N-[2-acetomido]-2-aminoethane sulfonic acid (ACES)-buffered charcoal yeast extract (ABCYE) agar plates [75], at 37° C. in the presence or absence of GFZ. GFZ and ACES were purchased from Sigma. All other media components were purchased from Fisher.

HL-60 Intracellular *L. pneumophila* inhibition assays. Tissue culture medium Roswell Park memorial Institute (RPMI) 1640 tisue culture medium was obtained from JRH Biosciences, Lenexa, Kans.; L-glutamine (GLN) from Mediatech, Herndon, Va., and phorbol 12-myristate 13-acetate (PMA) from Sigma. and normal human serum (NHS) (Ultraserum™) from Gemini Bio-Products, Calabasas, Calif. Promyelocytic HL-60 cells were differentiated into macrophage-like cells by incubation with 10 ng/ml PMA in RPMI with 2 mM GLN and 10% NHS in Teflon wells at 37° C. for 24 hours. These cells were washed, resuspended at $4 \times 10^6$ cells/ml in RPMI-2 mM GLN-10% NHS, and mixed with *L. pneumophila* Phil 1 ($4 \times 10^4$ CFU/ml) which had been grown for 2 days on ABCYE plates (final multiplicity of infection of 0.01). 100 μl aliquots of the suspension were plated in each well of a 96 well microtiter plate. The plates were centrifuged to pellet the cells and bacteria and incubated at 37° C. for 2.5 hours to allow phagocytosis of the L. pneumophila. 100 μl of fresh medium with or without 2× the final GFZ concentration, was added to the wells, and the plates were incubated at 37° C. At the times indicated, the cells and medium were harvested and assayed for L. pneumophila CFUs as described [58].

For the one-step assay, following pelleting of HL-60 cells and bacteria, the plates were incubated for 2.5 hrs to allow the HL-60 cells to internalize the bacteria. Gentamicin (100 μg/ml) was added for 0.5 hrs to kill extracellular bacteria. The cells were washed to remove gentamicin, overlaid with 200 μl fresh RPMI-2 mM GLN–10% NHS without or with GFZ (100 μg/ml), and incubated at 37° C. At the times indicated, the cells and medium were harvested and assayed for L. pneumophila CFUs as described [58]. L. pneumophila is unable to grow in tissue culture medium, so any increase in colony forming units reflects intracellular multiplication [54]. Data from the experiments are expressed as the average (+/−) the S.E.M (n=3).

HL-60 Cytotoxicity Assay.

HL-60 cells ($4 \times 10^5$ cells per well) were differentiated in the wells of a 96 well microtiter dish by incubation for two days at 37° C. in an atmosphere of 95% air 5% $CO_2$ with 10 ng/ml PMA in RPMI-2 mM GLN–10% NHS. Adherent cells were washed two times with RPMI-2 mM GLN and then incubated with RPMI-2 mM GLN–10% NHS (+/−) 100 μg/ml GFZ. 5-fold serial dilutions of L. pneumophla in RPMI, were added to the wells at multiplicities of 0.5, 0.1, 0.02, 0.004, and 0.0, starting with $2 \times 10^5$ bacteria added per well. After a 5 day incubation at 37° C., the dye MTT ((3-4,5-dimethylthiazole-2-yl)-2,5-diphenyl tetrazolium bromide) (Sigma), was added to each well at a concentration of 500 μg/ml. In this assay the $A_{570}$ is proportional to the number of viable macrophages in the wells [58]. The microtiter dishes were incubated for 4 hrs at 37° C., the culture medium was aspirated, and the reduced formazan dye was suspended in 100 μl of 0.04 M HCl-1% sodium dodecyl sulfate in isopropanol. The $A_{570}$ values of six separate wells, that had been seeded with $4 \times 10^5$ HL-60 cells infected with L. pneumophila infected at the same multiplicity of infection and incubated with or without GFZ, were averaged to determine macrophage viability.

Human Peripheral Blood Monocyte-derived Macrophage Assays.

Human leukocytes were purified by layering buffy coats on Histopaque-1077 and centrifuging at 400×g for 15 min. The leukocyte layer was washed 3× in RPMI 1640-2 mM GLN, resuspended in RPMI 1640-2 mM GLN–20% heat-inactivated human serum, added to 75 cm² flasks and incubated at 37° C. in an atmosphere of 95% air, 5% $CO_2$ to allow adhesion of monocytes. After two hours the nonadherent cells were removed by washing and fresh RPMI 1640-2 mM GLN–20% heat-inactivated human serum, was added to the adherent monolayers. Following 12 hours incubation, the medium was replaced with PD buffer containing 5 mM EDTA, and the flasks were incubated at 37° C. 5% $CO_2$ for 30 minutes to detach the monocytes. The detached monocytes were pelleted at 400×g for 15 minutes, and resuspended in RPMI 1640-2 mM GLN+30% heat-inactivated human serum, and stored in Teflon wells at 37° C. in humidified incubators in an atmosphere of 95% air and 5% $CO_2$. Human monocyte derived macrophages maintained in culture for five days were resuspended in fresh RPMI 1640-2 mM GLN+10% normal human ultraserum containing L. pneumophila at an MOI of approximately 0.001. 100 μl aliquots containing $4 \times 10^5$ monocyte-derived macrophages and $1 \times 10^2$ L. pneumophila were pelleted in the wells of a 96 well microtiter plate and incubated at 37° C. for 2.5 hours to allow phagocytosis of the L. pneumophila. 100 μl of fresh medium with or without 2× the final concentration of GFZ, clofibrate or fenofibrate, was added to each well. The plates were incubated at 37° C. in humidified incubators in an atmosphere of 95% air and 5% $CO_2$. At the indicated times, the cells and medium were harvested and assayed for L. pneumophila CFU's.

Antimicrobial Susceptibility Testing.

For determination of MICs, triplicate cultures of log phase L. pneumophila suspensions, final concentration $2 \times 10^6$ CFU/ml, were incubated in AYE broth containing two-fold serial dilutions of GFZ, fenofibrate, clofibrate, or bezafibrate for 48 hrs at 37° C. Growth was assessed by the optical density at $A_{600}$. Bacteriostatic effect was determined by incubating L. pneumophila suspensions, final concentration $2 \times 10^6$ CFU/ml, in AYE broth containing two-fold serial dilutions of GFZ (10–200 μg/ml) for 48 hrs at 37° C. 5 μl from each culture was spotted on ABCYE agar and incubated at 37° C. for three days. L. pneumophila grew in all spots indicating that GFZ was bacteriostatic, not bactericidal.

GFZ INHIBITS THE GROWTH OF MYCOBACTERIUM TUBERCULOSIS AND OTHER PATHOGENS

Gemfibrozil, Lopid™, a compound prescribed for hypertriglyceridemia in humans, was discovered to be an inhibitor of L. pneumophila growth in AYE broth ($MIC_{90}$=10 μg/ml) and in macrophages (100 μg/ml). The discovery that gemfibrozil (GFZ) inhibited the growth of L. pneumophila suggested that GFZ might inhibit additional bacterial species. GFZ demonstrated activity against 33% of the bacteria screened, including Mycobacterium tuberculosis, Nocardia sp., Staphylococcus aureus, and Staphylococcus epidermidis. Two yeast species, Sacchromyces cerevisiae and Candida albicans were also found to be susceptible to GFZ.

The susceptibility of M. tuberculosis was of particular interest since M. tuberculosis claims more lives, roughly 3 million people per year, than any other single infectious disease in the world [84]. While the reported number of new cases of tuberculosis in the United States is declining [85], it is nearly impossible to eradicate the disease since it can remain dormant and undetected in immunocompetent hosts for years. On average at least 5% of immunocompetent hosts will develop active disease in their lifetimes [86]. The rate is significantly higher for those who are, or become, immunocompromised [87,88].

Despite the magnitude of the problem, no new primary anti-tuberculosis medicines have been developed since the 1960's [89]. The emergence and rapid spread of multiple drug resistant M. tuberculosis strains has led to renewed interest in the development of compounds to treat and control this deadly organism. Unfortunately, significant mortality due to multiple drug resistant bacteria may no longer be limited to M. tuberculosis.

RESULTS

Screening of Various Species of Bacteria and Yeast for GFZ-mediated Growth Inhibition.

L. pneumophila Philadelphia 1 serogroup 1 was sensitive to growth inhibition by GFZ. To determine whether GFZ was specific for this strain of L. pneumophila we tested its effect on 38 other Legionella sp. strains using a zone of inhibition assay. A disk containing 250 μg of GFZ was added to a CYE agar plate overlaid with the test bacterium. The absence of bacterial growth in the area adjacent to the disk, or a "zone of inhibition," indicated sensitivity to GFZ. All 39 Legionella sp. strains were sensitive by this assay.

Additional nonpathogenic bacterial species were obtained from Dr. David Figurski and tested with the same assay. The finding that four of the eight strains tested demonstrated sensitivity to GFZ led to a collaboration with the Clinical Microbiology Department of Presbyterian Hospital to screen randomly-selected clinical strains of bacterial and fungal pathogens. The screen was performed by adding a sterile disk containing 2 mg of GFZ to a nutrient agar plate overlaid with the test pathogen. Eleven of the thirty one bacterial species tested, or 33%, demonstrated susceptibility to GFZ (FIG. 8). A variation of this assay was utilized for screening the mycobacterial strains in that disks containing 2 mg GFZ were embedded in 5 mls of nutrient agar prior to overlaying with bacteria.

Human pathogens in the susceptible group in addition to L. pneumophila included M. tuberculosis, Nocardia sp., S. epidermidis, and S. aureus. All of the susceptible species are reported to contain branched chain fatty acids }[13], although not all bacteria containing branched chain fatty acids demonstrated susceptibility to GFZ (e.g. L. monocytogenes) [13,46].

S. aureus and S. epidermidis susceptibility to GFZ on standard laboratory medium was fairly low, only a narrow zone of Inhibition was observed (e.g. 2–5 mm). To see if nutrients supplied by the medium might "rescue" S. aureus and S. epidermidis from the effects of GFZ, four strains of S. aureus and one strain of S. epidermidis were each plated on LB, a nutrient-rich medium, and TSB, a relatively nutrient-poor medium. The zones of inhibition were significantly larger on the TSB plates (e.g. 10–20 mm) (FIG. 9).

Nocardia sp. susceptibility was notable in that GFZ produced large zones of inhibition, e.g. 40–60 mm, by the disk assay. It was also noted that the GFZ zone of inhibition assay appeared to be an effective method of rapidly differentiating Nocardia sp. from atypical mycobacteria, all of which were resistant to GFZ on standard laboratory media.

Saccharomyces cerevisiae and Candida albicans were also found to be susceptible to GFZ when grown on SAB medium buffered to a pH of 7. No zone of inhibition was observed with unbuffered medium, as GFZ is insoluble at an acid pH.

MIC Determination for M. tuberculosis

The susceptibility of M. tuberculosis to GFZ was of special interest given the prevalence, morbidity, and mortality associated with infections by this organism. Therefore, we tested the GFZ susceptibility of 27 M. tuberculosis strains, 22 of which were resistant to one or more antitubercular drugs, by plating M. tuberculosis strains on nutrient medium containing 0, 50, 100, or 200 μg/ml of GFZ. Growth of all M. tuberculosis strains was completely inhibited by 100–200 μg/ml GFZ, regardless of their resistance to other antibiotics (FIG. 10). Comparable results were obtained when M. tuberculosis was added to 7H9 broth containing GFZ at concentrations of 50 or 300 μg/ml (FIG. 11).

EMS Mutagenesis

To search for genes involved in GFZ susceptibility/ resistance, and thereby identify its mechanism of inhibition, GFZ resistant mutants of L. pneumophila were sought. Over $10^{12}$ CFUs of wild type or EMS-mutagenizec *L. pneumophila* were plated on CYE plates containing 50 μg/ml of GFZ. No spontaneous mutants were obtained. Only one EMS-mutagenized *L. pneumophiia* variant, F4b, was identified. F4b had an $MIC_{90}$ of 50 μg/ml in an AYE MIC assay, compared to 10 μg/ml GFZ for the wild type *L. pneumophila* parent strain. F4b also demonstrated increased resistance to GFZ in an intracellular infection assay in HL-60 cells (FIG. 12).

GFZ Analog Assays

Previous results from the intracellular and broth assays testing the effect of fibric acids on *L. pneumophila*, indicated that structural analogs of GFZ, such as clofibric acid, had a modest inhibitory effect on *L. pneumophila* growth. Therefore, several GFZ analogs were obtained (FIG. 13) and tested by a zone of inhibition assay against *L. pneumophila* and the partially GFZ-resistant variant F4b (FIG. 14). Two of the analogs, 4-HPA and 3,4-HPA, were equally inhibitory for both wild type *L. pneumophila* and the partially GFZ-resistant variant F4b. Of note was the finding that both wild type *L pneumophila* and the F4b variant were more sensitive to 2-hydroxybenzoic acid (salicylic acid) than GFZ. Aside from GFZ, F4b demonstrated increased resistance to 2-hydroxybenzoic acid, also known as salicylate.

The random bacterial screen demonstrated that GFZ was active against a number of bacteria, notably *M. tuberculosis*, Nocardia sp. *S. aureus* and *S. epidermidis* all of which can cause infections which may be difficult to treat. *M. tuberculosis*, an acid-fast bacillus, latently infects up to one third of the world's population and is the leading cause of death in humans from a single infectious agent [84]. *M. tuberculosis* primarily infects the lungs, although extrapulmonary infection, with dissemination throughout the body also occurs. Nocardia sp. are gram-positive, weakly acid-fast, higher bacteria, also known as actinomycetes, that form branches similar to fungii, but induce a neutrophilic inflammatory response similar to other bacteria, and demonstrate susceptibility to antibiotics. Nocardia sp. primarily infects the lungs, resulting in a pneumonia but can spread to the skin and brain where it forms abscesses. Six to twelve months of antibiotic treatment may be required to cure Nocardia infections.

*S. aureus*, a gram-positive clustering coccus, often colonizes the nose, and is responsible for numerous serious infections including endocarditis, osteomyelitis, toxic shock syndrome, and pneumonia. Strains of this organism have been identified that are resistant to all known antibiotics. *S. epidermidis* is the primary agent associated with infections of prosthetic devices including heart valves, hip and joint replacements, and indwelling catheter lines. *S. epidermidis* is also associated with urinary tract infections in sexually active women.

*L. pneumophila*, a gram-negative bacilli, is the third or fourth most common cause of community-acquired pneumonia, and is a frequent cause of nosocomial pneumonia. Infection with *L. pneumophila* is associated with significant morbidity, mortality, and hospital costs.

*C. albicans*, a pathogenic fungi, is associated with oral, esophageal, intestinal, and vaginal infections in immunosuppressed patients, and commonly with vaginal infections in an immunocompetent population.

The observation that all susceptible bacteria (and yeast) contain branched fatty acids in their membranes indicates that GFZ may be inhibitory for bacteria capable of synthesizing a complex array of membrane fatty acids. Additional support for the involvement of fatty acids in GFZ inhibition is provided by the observation that addition of cleate to the medium of GFZ-inhibited *S. cerevisiae*, rescues these yeast from the inhibitory effects of GFZ. Addition of cleate to the medium also rescues *S. cerevisiae* from the antibiotic cerulenin, an inhibitor of fatty acid synthesis in yeast, bacteria, and mammalian cells [90,91].

Similarly, growth inhibition in *E. coli* mediated by drugs or by ts mutations affecting fatty acid synthesis, can be bypassed in many cases by the addition of fatty acids to the bacteriologic medium such. as oleic acid ($C_{18:1}$), a mono-unsaturated sixteen carbon fatty acid, and palmitic acid ($C_{16:0}$), a saturated sixteen carbon fatty acid [32,92]. The observation that *S. aureus* showed increased susceptibility to GFZ on TSB medium as compared to the nutrient rich LB medium, suggests that LB supplies metabolite(s), possibly fatty acids, that are able to bypass the effect of GFZ.

It is important to note that the *M. tuberculosis* assays were performed in the presence of oleic acid. Standard mycobacterial medium utilizes oleic acid (or Triton) as a detergent to prevent "cording" of the bacteria. It is possible that if oleic acid is left out of the medium, *M. tuberculosis* will exhibit greater susceptibility to GFZ. However, testing the ability of GFZ to inhibit the growth of *M. tuberculosis* within infected human macrophages may be a more relevant approach.

Therefore, if the bacterial strains screened for GFZ-susceptibility (FIG. 9) were re-tested on medium lacking fatty acids, additional susceptible strains might be identified. The GFZ-sensitivity of bacteria tested on nutrient agar free of fatty acids may better correlate with the susceptibility of these bacteria to GFZ in vivo.

Other factors besides the presence of fatty acids may contribute to the presence or size of a zone of inhibition adjacent to a GFZ disk. The ability to observe a zone of inhibition for *S. cerevisiae* and *C. albicans* was dependent on buffering the medium to a pH of 7. GFZ solubility in aqueous solution decreases as pH decreases. Therefore, to ensure diffusion of the drug through the medium, and to prevent acidification of the medium during growth, it was necessary to buffer the pH. The effects of pH on GFZ sensitivity was not examined with any other medium or pathogen.

The zone of Inhibition surrounding a GFZ disk represents the area in which the concentration of GFZ is high enough to inhibit bacterial growth. If GFZ is not very soluble in a given medium, or is tightly bound by proteins in the medium (e.g. albumin), the rate of diffusion from the disk may be slowed, resulting in a short and steep concentration gradient. The rate of diffusion is also affected by the thickness of the agar plate since the drug diffuses in three dimensional in agar, i.e., the thicker the plate, the smaller the zone. Nonetheless, for screening purposes, zones of inhibition afford a rapid and easy method by which to assess the presence, but not the extent, of GFZ sensitivity.

The observation that *M. tuberculosis* strains that are resistant to multiple conventionally used antibiotics were as sensitive to GFZ as *M. tuberculosis* strains that are sensitive to these antibiotics suggests that GFZ may be a lead compound for identifying antibiotics that can inhibit the growth of multiply drug resistant *M. tuberculosis*. The relative impermeability of the cell well accounts for the majority of the drug resistance in *M. tuberculosis* strains. However, many potential drug resistance determinants, including β-lactamases, aminoglycoside acetyl transferases, and many potential drug efflux systems, are encoded in its genome [93]. Whether any of the chromosomally encoded potential drug resistance determinants confers increased resistance to GFZ is unknown.

Resistance to drugs can occur by several mechanisms. Drug resistance may result from the overuse of a drug, thereby selecting for organisms that grow despite the presence of the drug. The sporadic use of drugs, which often happens in unobserved TB therapy, selects for increasingly resistant bacterial populations. Subinhibitory concentrations of a drug also enhance the outgrowth of drug-resistant mutant strains, and encourage the spread of plasmids encoding drug resistance mechanisms from one species to another. Unfortunately, the development of resistance to one drug, often confers resistance to other drugs within the same class.

Our inability to identify spontaneous or EMS-generated GFZ resistant mutants suggests either that the *L. pneumophila* target cannot be readily altered to confer resistance to this drug, or, that GFZ can affect more than one enzyme or pathway in *L. pneumophila*. The ability to inhibit multiple targets in an organism is a desirable property for an antibiotic.

The observation that GFZ inhibited only 33% of the bacteria screened suggests that GFZ has a narrow spectrum of ant-microbial activity. While narrow spectrum antibiotics are less likely to generate the revenues desired by large pharmaceutical companies, they have the potential advantage of targeting the primary agent of disease without inhibiting the body's normal flora. Antibiotics with these characteristics should limiting the generation and spread of drug resistant bacteria. The finding that GFZ inhibited twenty three drug resistant strains of *M. tuberculosis*, Nocardia sp. and *S. aureus*, encouraged us to continue research in this area, especially with regard to the mechanism(s) of GFZ-mediated bacterial inhibition.

MATERIALS AND METHODS

Antimicrobial Susceptibility Testing

For determination of bacterial susceptibility, bacterial suspensions were overlaid on suitable nutrient agar plates, a sterile paper disk containing 2 mg of GFZ was added, and the plates were incubated at 37° C. until a lawn of bacterial growth was observed. Bacteria were classified as susceptible if there was a zone of growth inhibition of more than 2 mm surrounding the disk. Non-pathogenic bacterial strains were graciously provided by D. Figurski, College of Physicians and Surgeons, Columbia University, NYC, N.Y. Pathogenic bacterial strains (except for *L. pneumophila*) used for GFZ susceptibility testing were clinical isolates obtained from Dr. P. Della Latta, Director Clinical Microbiology, Presbyterian Hospital, and generously screened following NCCLS standardized procedures by the Clinical Microbiology Dept. of Columbia-Presbyterian Hospital. A sterile disk containing 2 mg of gemfibrozil (Sigma) was added to the overlay. Sensitivity was determined by the presence of a zone of growth inhibition surrounding the disk.

*M. tuberculosis* Susceptibility Assay.

100 μl of a standard dilution of each of 5 drug-sensitive and 22 drug-resistant *M. tuberculosis* strains were tested for GFZ-susceptibility on 5 ml quadrants of solid Middlebrook 7H10 medium (Baltimore Biological Labs) supplemented with oleic acid, dextrose, catalase, and albumin (OADC) obtained from ifco, Detroit, Mich., containing 0, 50, 100, or 200 μg/ml of GFZ. Standard dilutions were prepared by resuspending each strain to a McFarland standard of one, approximately $10^8$ organisms, and diluted 100-fold. Strains were obtained from the Clinical Microbiology Dept. of Columbia-Presbyterian Hospital. Plates were scored following incubation for three weeks at 37° C. For broth assays, approximately $10^7$ bacteria (100 μl of a Mc Farland standard of 1) was added to BBL Prepared Culture Media (Beckton Dickenson) containing 5 mls of Middlebrook 7H9 broth with glycerol. The cultures were incubated for 21 days at 37° C. after which turbidity was visually assessed for growth.

EMS Mutagenesis.

Log phase *L. pneumophila* in AYE broth were incubated with 15 μl EMS for 15 minutes at 37° C., pelleted, washed twice, resuspended in 1 ml AYE, titered for CFUs, diluted 1:10 in AYE and grown overnight at 37° C. EMS exposure resulted in approximately 40% and 70% viability in two independent experiments. Following overnight growth, the EMS-mutagenized *L. pneumophila* were grown on CYE plates at 37° C. for two days, harvested, and suspended at Approximately $10^{10}$ CFU's/ml in AYE broth. 100 μl aliquots were plated on CYE agar containing 50 μg/ml GFZ. Putative —SFZ-resistant colonies were passed once on CYE agar without GFZ, and then on CYE agar containing GFZ 50 μg/ml. Only one GFZ-resistant colony was obtained after the second passage on CYE agar containing GFZ 50 μg/ml. Well over $10^{12}$ colonies were screened for resistance to GFZ.

Effect of GFZ in the Growth of the *L. pneumophila* F4b Variant in HL-60 Cells.

Tissue culture medium RPMI 1640 was obtained from JRH Biosciences, Lenexa, Kans.; L-glutamine (LGN) was obtained from Mediatech, Herndon, Va., and phorbol 12-myristate 13-acetate (PMA) was obtained from Sigma. Normal human serum (Ultraserum™) was obtained from Gemini Bio-Products, Calabasas, Calif. Promyelocytic HL-60 cells were differentiated into macrophage-like cells by incubation with 10 ng/ml PMA in RPMI with 2 mM GLN and 10% NHS in Teflon wells at 37° C. for 24 hours. These cells were washed, resuspended at $4\times10^6$ cells/ml in RPMI-2 mM GLN-10% NHS, and mixed with *L. pneumophila* F4b ($4\times10^4$ CFU/ml) which had been grown for 2 days on ABCYE plates (final multiplicity of infection of 0.01). 100 μl aliquots of the suspension were plated in each well of a 96 well microtiter plate. The plates were centrifuged to pellet the cells and bacteria and incubated at 37° C. for 2.5 hours to allow phagocytosis. 100 μl of fresh medium (+/−) 2× the final GFZ concentration, was added to the wells, and the plates were incubated at 37° C. At the times indicated, the cells and medium were harvested and assayed for *L. pneumophila* CFUs as described [58]. Data from the experiments are expressed as the average (+/−) the S.E.M (n=2).

GFZ INDUCES THE ACCUMULATION OF POLYHYDROXYBUTYRATE IN *LEGIONELLA PNUEMOPHILA*

Gemfibrozil (Lopid™), a drug used to treat hyperlipidemia due to high serum triglycerides, inhibits the growth of pan-sensitive and multiple-drug resistant *Mycobacterium tuberculosis*, of *Legionella pneumophila*, the causative agent of Legionnaire's disease, and of several other bacterial pathogens and yeast. The finding that GFZ (100–200 μg/ml) inhibited four pan-sensitive and twenty two drug resistant strains of *M. tuberculosis* within a two-fold concentration range, suggested that GFZ might have a novel mechanism of action.

The inability to generate GFZ-resistant *L. pneumophila* mutants by EMS mutagenesis (supra), made it difficult to search for resistance mechanisms and putative targets. Therefore, the morphology of *L. pneumophila* following incubation with GFZ was examined by transmission electron microscopy (TEM) to determine whether GFZ had a visible effect on cell structure that might provide a clue to its mechanism of action.

RESULTS

Analysis of *L. pneumophila* Incubated on CYE Agar in the Presence or Absence of GFZ by Transmission Electron Microscopy.

By TEM, *L. pneumophila* grown on CYE agar in the absence of GFZ, contained occasional, small, electron-lucent cytoplasmic inclusions similar to those reported by others (FIGS. 15A–D) [94,95]. However, when *L. pneumophila* were grown on CYE agar containing 30 μg/ml of GFZ, two populations were observed. The bacteria either appeared distended by numerous, large, electron-lucent, cytoplasmic inclusions, or had a marked absence of electron-lucent inclusions (FIG. 15B). The small electron-lucent inclusions found in *L. pneumophila* grown in the absence of GFZ are reported to contain polyhydroxybutyrate (PHB), polymers of 3-hydroxybutyric acid (3-HB) [96,105].

Although 10 μg/ml of GFZ inhibits growth of $10^6$ *L. pneumophila* CFUs/ml in AYE broth, and of individual colonies on CYE agar, higher concentrations of GFZ are required to inhibit growth of a high density *L. pneumophila* innoculum ($10^9$–$10^{10}$ CFUs) on CYE agar. When a large number of *L. pneumophila* is added to CYE plates containing 30 μg/ml of GFZ, the bacteria grew to form a sparse lawn. This lawn provided sufficient *L. pneumophila* for analysis. The ability of a large innoculum to grow on CYE medium containing GFZ at 3× the broth MIC is consistent with reports that an innoculum size affects the apparent MIC of an antibiotic for a given bacteria [76,97]. Additionally, the presence of charcoal in CYE plates increases the MIC of many antibiotics. Substitution of potato starch for charcoal generally results in lower MIC values although this technique was not used here [76].

Nile Blue A Staining of *L. pneumophila* Grown in the Presence or Absence of GFZ.

Nile Blue A (NBA), a fluorescent dye which stains PHB granules in bacteria [98], was used as a preliminary screen to assess whether the large electron-lucent granules seen by electron microscopy, contained PHB. Nile Blue A staining allowed the simultaneous visualization of larger populations of bacteria. *L. pneumophila* grown on CYE agar in the presence or absence of GFZ 30 μg/ml, was harvested and stained with NBA. *L. pneumophila* grown in the presence of GFZ contained many large, distending, brightly fluorescent NBA-stained inclusions (FIGS. 15A–D), similar to the inclusions seen by EM. *L. pneumophila* grown in the absence of GFZ contained fewer, and smaller, NBA-stained inclusions than *L. pneumophila* grown in the presence of GFZ (FIGS. 15A–D). Thus, consistent with the EM findings, GFZ treated *L. pneumophila* contained populations of bacteria in which the cytosolic space was filled with NBA-stained material and populations of bacteria containing few if any NBA-stained inclusions.

Gas Chromatography-mass Spectrometry (GC-MS) of *L. pneumophila* Grown in the Presence or Absence of GFZ.

Although Nile Blue A is reported to be a specific stain for PHB, as opposed to glycogen, polyphosphates, and other bacterial inclusions, it had not been shown to be specific for polyhydroxybutyrate versus other polyhydroxyalkanoates.

While *L. pneumophila* is reported to contain PHB granules, some bacteria are known to respond to alterations in growth conditions by varying the composition of their granules, (i.e. polymerization of short chain carboxylic acid monomers other than 3-HB) [99,100]. Therefore, GC-MS was used to assess the composition of the inclusions. *L. pneumophila* grown in the presence or absence of GFZ was subjected to hydrochloric acid propanolysis [101] to trans-esterify 3-hydroxyalkanoate monomers with propanol to form the corresponding propyl esters. Propyl esters were extracted into dichloroethane and analyzed by GC-MS. A fifty-fold increase in the amount of 3-HB-propyl ester was observed in *L. pneumophila* grown for three days on CYE agar in the presence of GFZ, relative to *L. pneumophila* grown on CYE agar in the absence of GFZ (FIG. 16). The difference between the presence and absence of GFZ for PHB was analyzed by a student's t-test and found to be significant with t=−6.05, corresponding to a p<0.05 for three independent experiments.

Figure 19:
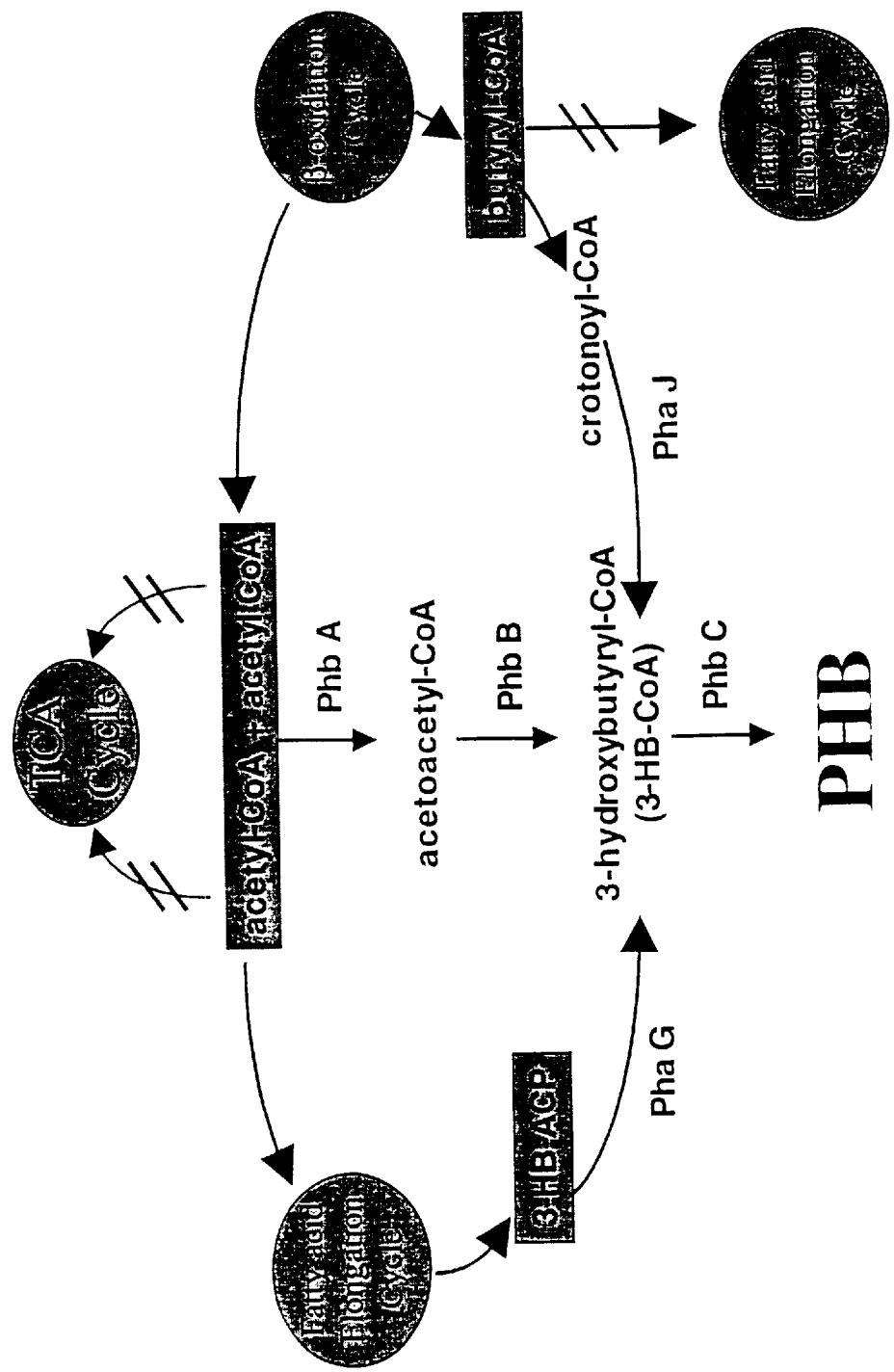

TEM and Nile Blue A staining of *L. pneumophila* grown in the presence of a subinhibitory concentration of GFZ indicated that GFZ induced the accumulation of PHB-containing granules in a majority of the bacteria. However, populations of bacteria lacking significant accumulation of PHB were also detected. In experiments not reported, log phase *L. pneumophila* contained a lower percentage of PHB than stationary phase bacteria. Since the viability of the population of GFZ-treated *L. pneumophila* lacking large PHB was not assessed, it is unclear whether these bacteria were growing and "resistant" to the concentration of GFZ used, or were dead and therefore unable to form inclusions.

*L. pneumophila* is not unique in its ability to form granules containing PHB. Several bacterial species are reported to accumulate granules containing polyhydroxyalkanoates (PHA), including *Alcaligenes eutrophus, Bacillus megatarium, Pseudomonas oleovorans, Pseudomonas aeruginosa*, and some Rhodococcus, Corynebacterium, and Nocardia strains [102,103]. Since GFZ did not inhibit the growth of *Pseudomonas aeruginosa*, the ability to form PHA granules is not correlated with GFZ susceptibility.

PHAs are natural polyesters composed of, up to 1,000 b-hydroxyacyl monomer units, 3 to 14 carbons in length. The function of these stored PHAs may be to act as an oxidizable substrate during oxygen limitation, as a carbon and energy source, or as a protective mechanism against the degradation of cellular components such as RNA and protein during nutrient deprivation [102,103]. Since *L. pneumophila* are able to utilize exogenous 3-HB as a carbon source [96], it is likely that their PHB stores contribute to their ability to maintain ATP content and survive in tap water for many months [104,105].

PHAs usually accumulate in bacteria in response to phosphorous, oxygen, nitrogen, or iron limitation in the presence of a carbon source [105,106]. However, to the best of our knowledge, these conditions were not present in our experiments. We noted however, that PHB synthesis and fatty acid synthesis utilize similar precursors and intermediates. Therefore, we hypothesized that the accumulation of PHB was due to a GFZ-mediated inhibition of fatty acid synthesis (FIG. 17), resulting in the accumulation of fatty acid precursors and intermediates before the block, and their subsequent shunting into PHB synthesis (FIG. 18).

Bacteria that synthesize branched chain fatty acids, such as *L. pneumophila*, can utilize both acetyl CoA and butyryl CoA as fatty acid precursors [13] [107] [108]. Condensation of two acetyl-CoA molecules is often the first step in PHB synthesis. Butyryl-CoA has been shown to be incorporated into PHB without degradation to acetyl CoA. Presumably this occurs following oxidation of butyryl-CoA to crotonyl-CoA, and hydration to (R)-3-HB-CoA by enzymes involved in β-oxidation [109]. Additionally, an enzyme PhaG in *P. putida* can mediate the conversion of 3-HB-ACP, an intermediate in fatty acid synthesis, into 3-HB-CoA, the monomer unit for PHB synthesis. Experiments described in supra are consistent with the hypothesis that GFZ causes the accumulation of fatty acid intermediates in *L. pneumophila* and that these intermediates are likely to be responsible for the GFZ-induced accumulation of PHB reported in this study.

METHODS AND MATERIALS

TEM of *L. pneumophila.*

*L. pneumophila* was grown for two days on CYE plates, harvested, and resuspended to a concentration of $10^{10}$–$10^{11}$ CFU's/ml in AYE. $10^{9}$–$10^{10}$ bacteria were added to CYE agar medium without or with GFZ (30 μg/ml). The plates were incubated for three days at 37° C. The bacteria were harvested, pelleted and fixed by resuspension in 2.5% glutaraldehyde for 45 minutes at 25° C., rinsed in 0.1 M $NaPO_4$ buffer (pH 7.5) and stored in this buffer overnight, rinsed 2× in 0.1M cacodylate buffer (pH 7.35), postfixed in 1% osmium tetroxide, rinsed in cacodylate buffer pH 7.35, rinsed in 0.1 M NaAc buffer (pH 6.0), stained in 1% uranyl acetate in 0.1 M NaAc buffer (pH 6.0) for 2.5 hours at 4° C., dehydrated through graded alcohols, embedded in epoxy resin, sectioned into 600 Å sections with a Sorvall MT6000 ultramicrotome, and mounted on 200 mesh copper grids. The sections were stained with uranyl acetate for 15 minutes followed by lead citrate for 10 minutes and examined by TEM using a JEOL1200EX electron microscope.

Nile Blue A Staining of *L. pneumophila.*

*L. pneumophila* were grown for two days on CYE plates, harvested, and resuspended at a concentration of $10^{10}$–$10^{11}$ CFU's/ml in AYE. $10^{9}$–$10^{10}$ bacteria were added to CYE agar medium without or with GFZ (30 μg/ml). The plates were incubated for three days at 37° C. The bacteria were harvested, resuspended in water, smeared on a glass slide and heat fixed. The slides were incubated in a 1% aqueous solution of Nile Blue A for 10 minutes at 55° C., washed with tap water, destained for 1 minute in 8% aqueous acetic acid, and air dried. The smears were remoistened with water, covered with a No. 1 glass cover slip, and examined by fluorescence microscopy at 460 nm.

Gas Chromatography-mass Spectrometry.

Identification and quantitation of 3-hydroxybutyrate (3-HB) was performed by gas chromatography-mass spectrometry (GC-MS). 3-HB propyl esters were formed for analysis by hydrochloric acid propanolysis of lyophilized bacteria using benzoic acid as an internal standard [101]. Hydrochloric acid, propanol, benzoic acid, and dichloroethane (DCE) were all obtained from Sigma. In brief, *L. pneumophila* were grown on CYE agar in the absence or presence of a subinhibitory concentration of GFZ (30 μg/ml) for three days, harvested, and lyophilized. 2 mls DCE, 2 mls acidified propanol, and 200 μl of internal standard solution (0.8 mg/ml of benzoic acid in 1-propanol) were added to 40 mg of lyophilized bacteria and the mixture was incubated for 2 hrs at 100° C. After cooling to room temperature, the sample was washed with 4 mls water. The DCE-propanol phase was reserved and stored at 4° C. A standard curve was constructed by converting known quantities of 3-HB (Sigma) and benzoic acid to their propyl esters, using hydrochloric acid propanolysis, as before. Prior to analysis, propyl esters in dichloroethane were dried under a stream of nitrogen and resuspended in an equivalent volume of ethyl acetate. A 2 μl aliquot of the DCE propanol extract of each sample was analyzed after splitless injection into a Hewlett Packard 5987A GC/MS equipped with a DB-1 fused-silica capillary column (30 m×0.2 mm) using helium as the carrier gas. The temperatures of the injector and the source were 220° C. and 200° C., respectively. The column temperature program started at 40° C. for 1 min, and increased at a rate of 8° C./min to 200° C. Samples were ionized by electron impact (70 eV). The abundance of ions at m/e 105 was used to quantitate benzoic acid, while the abundance of ions at m/e 87 was used to quantitate 3-HB.

GFZ INHIBITS LIPID SYNTHESIS IN *LEGIONELLA PNEUMOPHILA*

Previous work demonstrated that growth of several bacterial species and yeast strains was inhibited by GFZ. The observation that *M. tuberculosis* strains encoding resistance to many different antibiotics were sensitive to GFZ, suggested that GFZ inhibited *M. tuberculosis*, and likely other bacteria, by a novel mechanism. The observation that GFZ stimulated PHB accumulation, led to the hypothesis that GFZ inhibited an enzyme in bacterial fatty acid synthesis resulting in the accumulation of precursors or intermediates which were shunted into PHB synthesis (FIG. 19). Experiments are described herein demonstrating the ability of GFZ to inhibit $^{14}$C-acetate incorporation into bacterial fatty acids. These findings confirm that GFZ targets bacterial fatty acid synthesis.

Figure 20:
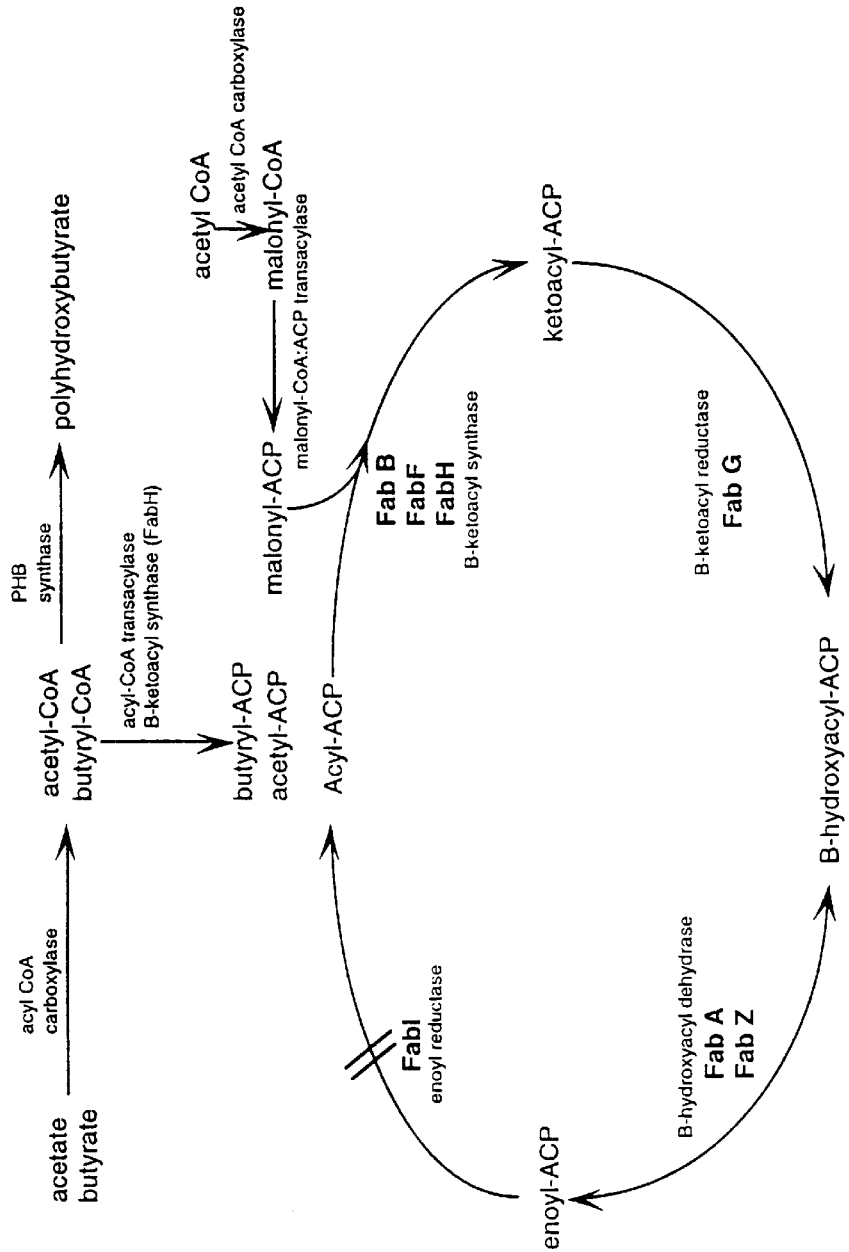

Fatty acids are synthesized by the successive addition of malonyl-ACP to a primer-ACP or a fatty acyl-ACP (FIG. 20). Malonyl-ACP is synthesized from acetyl-CoA which is itself a product of β-oxidation of fatty acids, or, of decarboxylation of pyruvate during growth on sugar. Many bacteria can also utilize exogenous acetate as a growth substrate. Acetate from the medium diffuses into the cytoplasm where it is converted to acetyl-CoA. Acetyl Co-A is subsequently used for oxidation via the tricarboxylic acid (TCA) cycle, for replenishment of intermediates of the TCA cycle, for leucine biosynthesis, and for lipid biosynthesis [112]. While *L. pneumophila* is capable of oxidizing acetate [96, 113], $^{14}$C-acetate added to *L. pneumophila* cultures is primarily incorporated into the lipid fraction [113]. Therefore, $^{14}$C-acetate is useful as a tracer of fatty acid synthesis in this bacterium.

Fatty acid synthesis in most bacteria and plants is carried out by discrete, separable enzymes, which are collectively described as a Type II fatty acid synthetase (Type II FAS) system [5]. In contrast, fatty acid synthesis in mammalian cells is carried out by a homodimer of a single polypeptide encoding seven distinct enzymatic functions, characteristic of a Type I fatty acid synthetase (Type I FAS) [4]. Differences between the human and bacterial fatty acid synthetic enzymes may account for the ability of GFZ to inhibit fatty acid synthesis in certain bacteria, without affecting the viability of mammalian cells.

RESULTS $^{14}$C-acetate Incorporation into Whole *L. pneumophila*.

Figure 21:
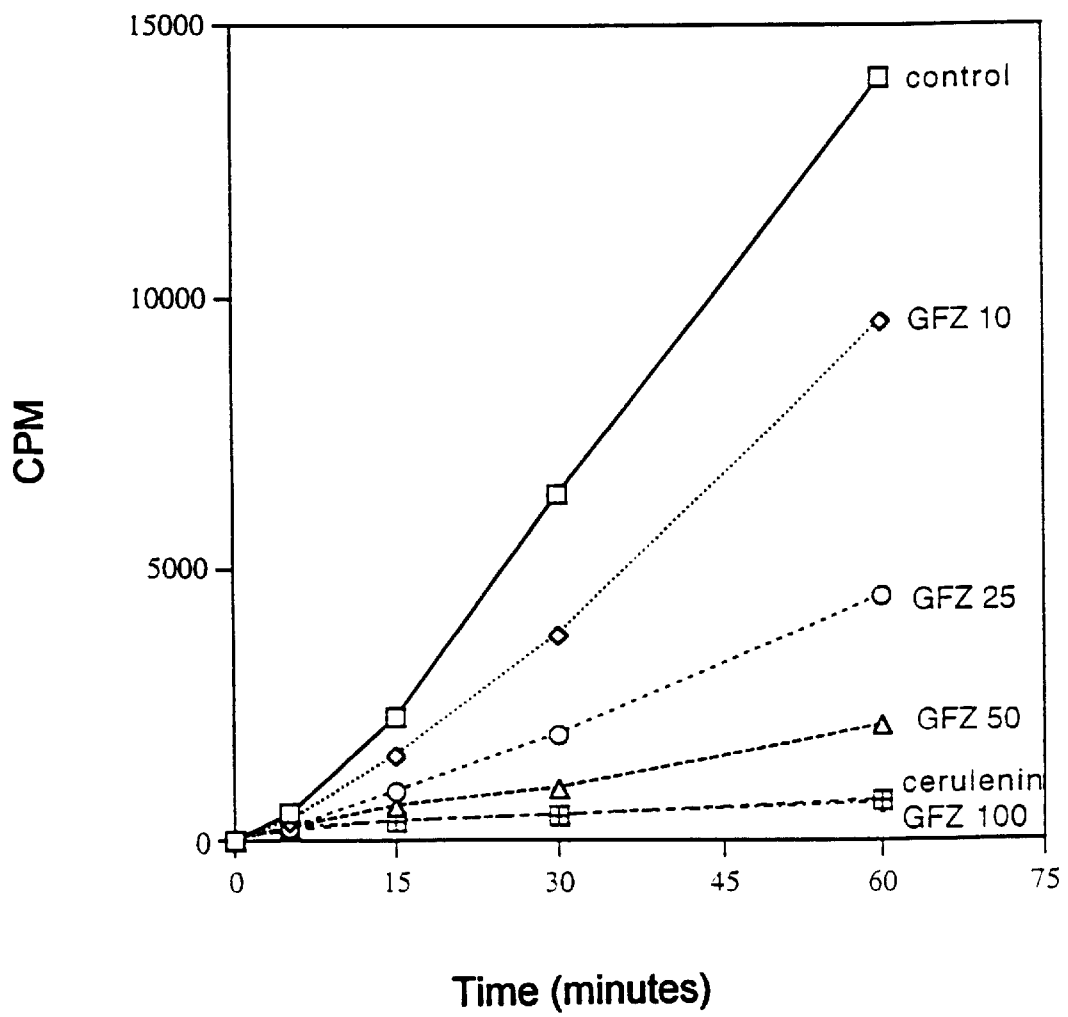
Figure 22:
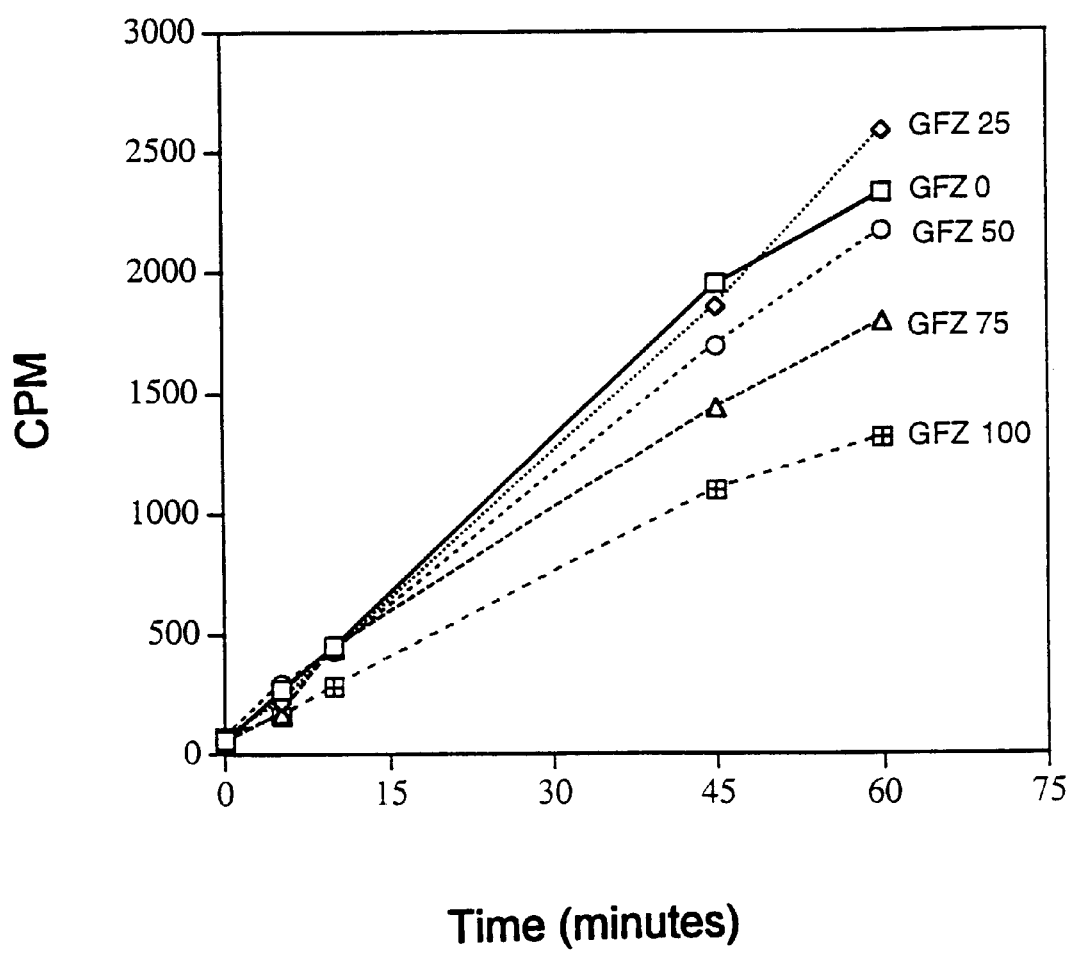

To test whether GFZ inhibited fatty acid synthesis, $^{14}$C-acetate was added to the medium of log phase *L. pneumophila* in AYE broth in the presence of increasing concentrations of GFZ (FIG. 21). Cerulenin, a known inhibitor of bacterial and mammalian fatty acid synthesis, was used as a control. Concentrations of GFZ as low as 10 μg/ml (40 μM) inhibited of $^{14}$C-acetate incorporation into wild type *L. pneumophila* within 15 minutes after the addition to the medium. Fifty percent inhibition relative to the control was achieved with a GFZ concentration of 25 mg/ml (100 mM) within 15 minutes of the drugs addition to the medium. However, inhibition of $^{14}$C-acetate incorporation into F4b, the *L. pneumophila* derived mutant with moderate resistance to GFZ (MIC$_{99}$=50 μg compared to 10 μg/ml for wild type *L. pneumophila*) required 100 μg/ml (400 μM) GFZ to inhibit $^{14}$C-acetate incorporation by 50% (FIG. 22).

Figure 23:
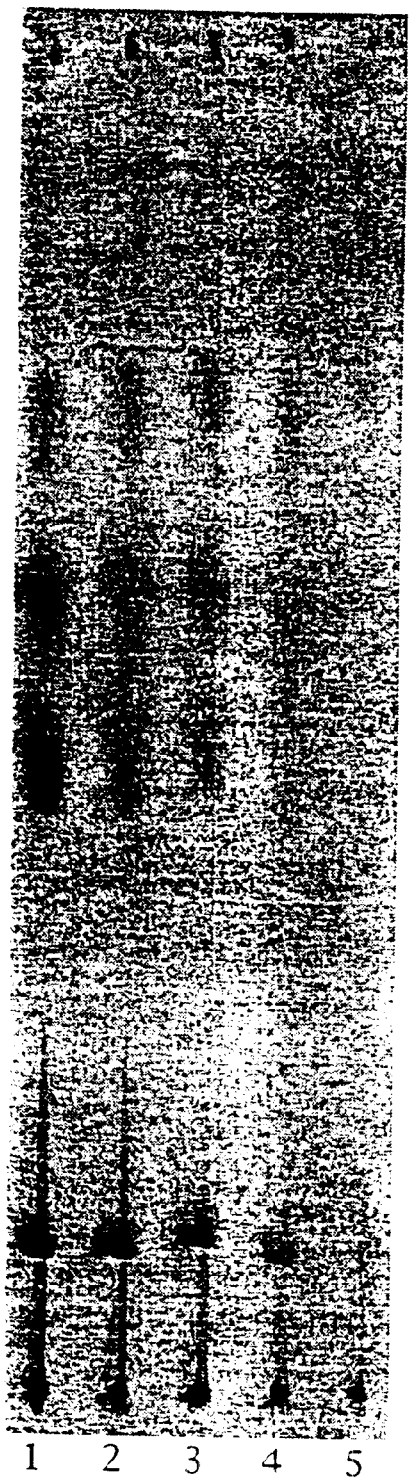

To confirm that incorporation of $^{14}$C-acetate into TCA precipitable material in whole bacteria accurately reflected $^{14}$C-acetate utilization for fatty acid synthesis, I analyzed $^{14}$C acetate incorporation into chloroform/methanol extractable material from *L. pneumophila* grown in the presence or absence of GFZ. *L. pneumophila* was incubated for one hour in medium containing $^{14}$C-acetate and increasing concentrations of GFZ. The bacteria were then pelleted, extracted with chloroform/methanol, and the extracts were analyzed by thin later chromatography (TLC). Assessment of the amounts of $^{14}$C radiolabel recovered in the chloroform/methanol extracts and autoradiography of the TLC plates (FIG. 23), confirmed that GFZ inhibited $^{14}$C-acetate incorporation into fatty acids in a dose dependent manner. TLC analysis showed that the decrease in $^{14}$C-acetate incorporation was equally distributed among the various fatty acid containing moieties. We draw two conclusions from thus experiment. First, GFZ inhibits fatty acid synthesis in *L. pneumophila*. Second, it does so by blocking an early step in fatty acid synthesis, since $^{14}$C-acetate incorporation into all fatty acid containing lipids was inhibited equally.

$^{14}$C-acetate Incorporation into *L. pneuaophila* Lysates.

Figure 24:
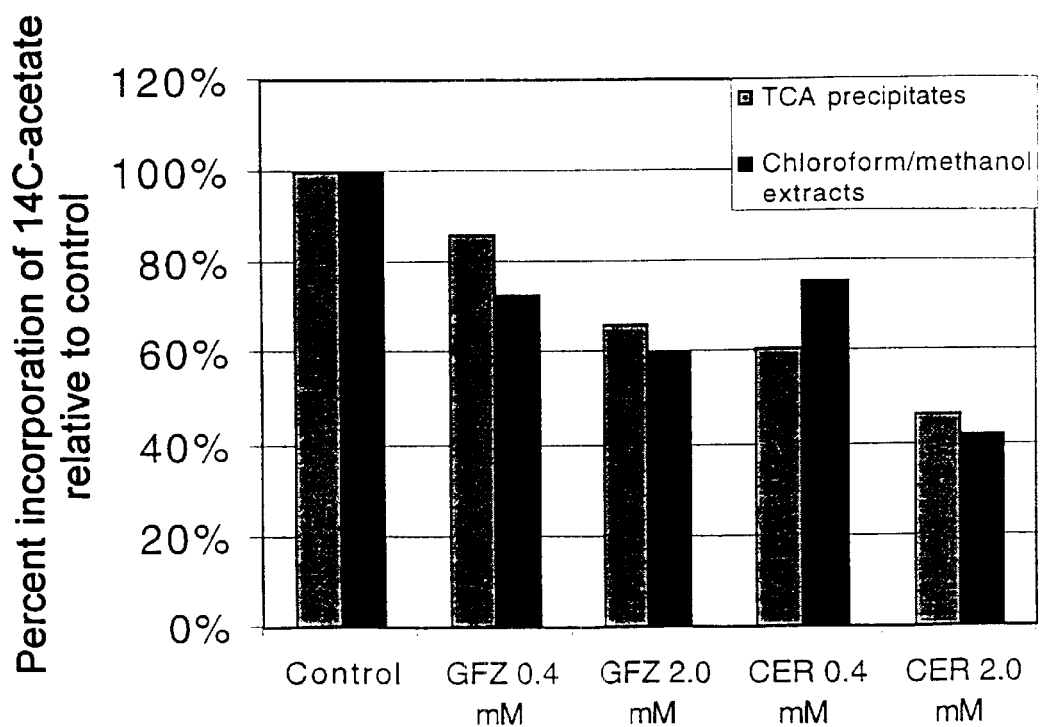
FIG. 24. Comparison of TCA precipitation and chloroform/methanol extraction as a measure of GFZ inhibition of $^{14}$C-acetate incorporation in L. pneumpchila lysates. GFZ or cerulenin at 0.4 mM or 2.0 mM concentrations was added to L. pneumophila lysates in the presence of $^{14}$C-acetate (5 μCi/ml), total volume 500 μl, and incubated at 37° C. for one hour. 200 μl ing the FabT column with 40 mM imidazole; 7=400 mM imidazole eluate of the FabT column; 8=*E. coli* FabI lysate; 9=flow through after washing the FabI column with 40 mM imidazole; 10=400 mM imidazole eluate of the FabI column.

To determine whether GFZ inhibited $^{14}$C-acetate incorporation into lipids in cell lysates lysates were prepared from log phase *L. pneumophila* and incubated for one hour at 37° C. in 50 mM TrisHCl buffer (pH 7.6) containing ATP, Mg$^{++}$, CoA, $^{14}$C-acetate, and GFZ. As observed with intact bacteria, GFZ inhibited $^{14}$C-acetate incorporation into TCA-precipitable material in these lysates. Further analysis of chloroform/methanol extracts of these lysates confirmed that the $^{14}$C-acetate was largely incorporated into lipids (FIG. 24).

While GFZ inhibited $^{14}$C-acetate incorporation into fatty acids in the lysate, it was not as effective an inhibitor in these lysates as it was in whole cells. 0.4 mM GFZ only inhibited $^{14}$C-acetate incorporation into TCA precipitable material in a lysate by 15%, while 0.4 mM GFZ inhibited $^{14}$C-acetate incorporation into TCA precipitable material in whole cells by greater than 90% (FIG. 21). Similarly, cerulenin was a less effective inhibitor of $^{14}$C-acetate incorporation into lysates than whole cells (compare FIGS. 21 and 24).

Figure 25:
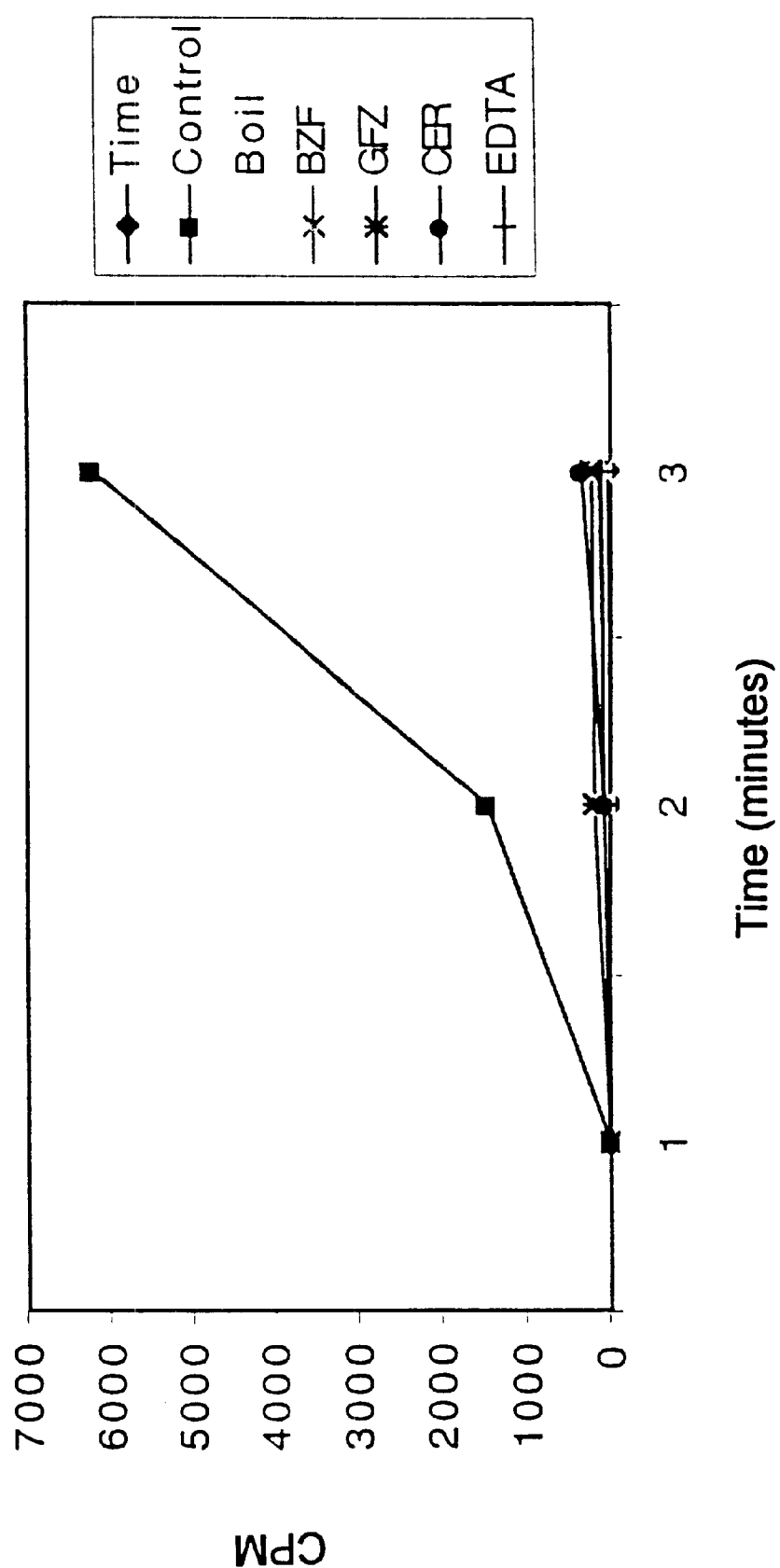

Control experiments showed that lysates that had been boiled prior to $^{14}$C-acetate addition, or, had been preincubated with 10 mM EDTA, did not incorporate $^{14}$C-acetate into TCA precipitable material (FIG. 25). EDTA inhibits fatty acid synthesis by chelating Mg$^{++}$ which is a required cofactor for ATP-dependent enzymes. In the presence of EDTA, CoA synthase is unable to form acetyl-CoA so malonyl-ACP is not formed and elongation does not occur.

The effect of a second fibric acid, bezafibrate (BZF) on $^{14}$C-acetate incorporation in *L. pneumophila* lysates was compared with that of GFZ and cerulenin. Surprisingly, BZF was a better inhibitor than GFZ in a lysate (FIG. 25).

Effect of GFZ Analogs on $^{14}$C-acetate Incorporation.

Figure 26:
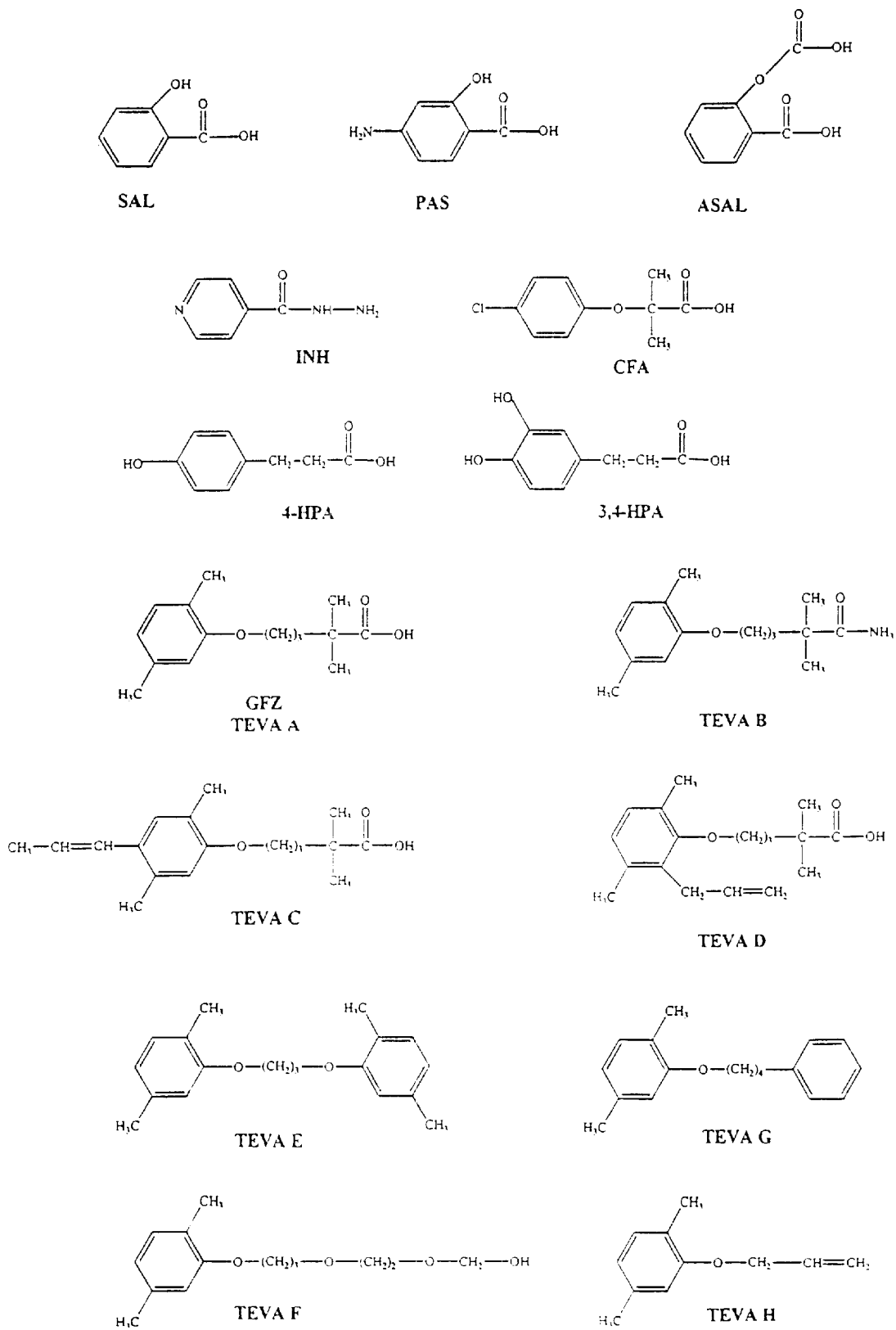
Figure 27A:
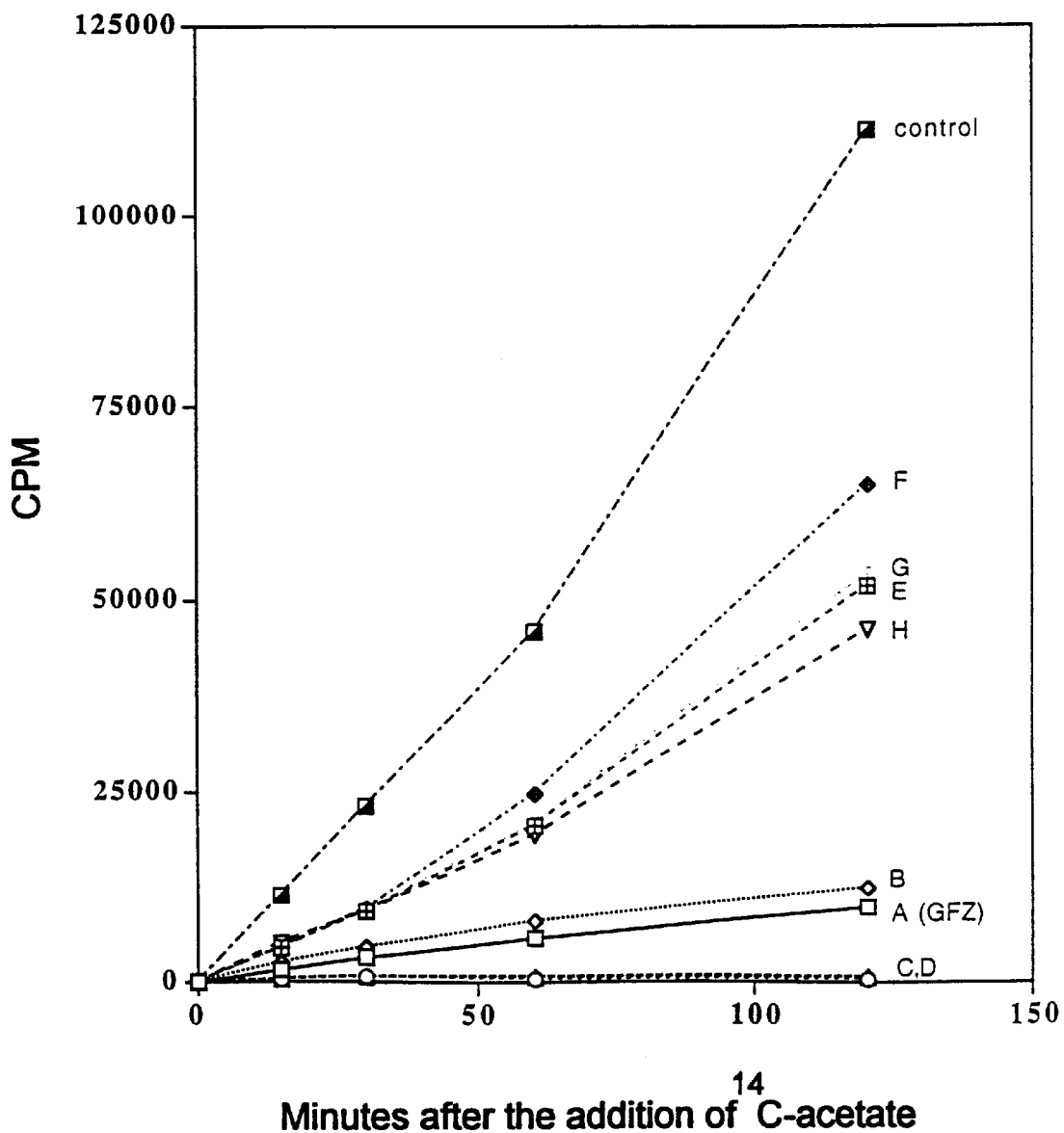
Figure 27B:
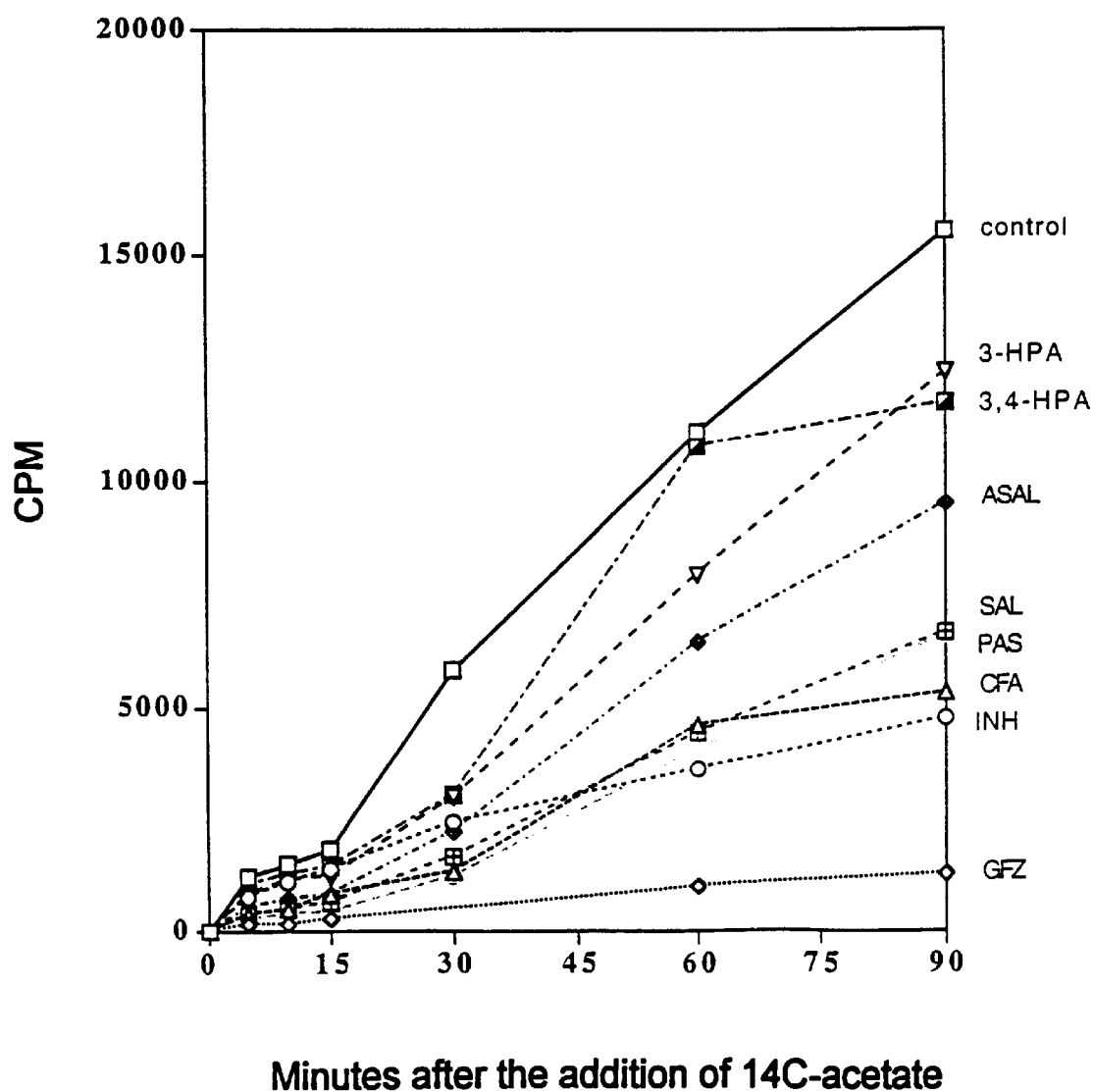
Figure 28A:
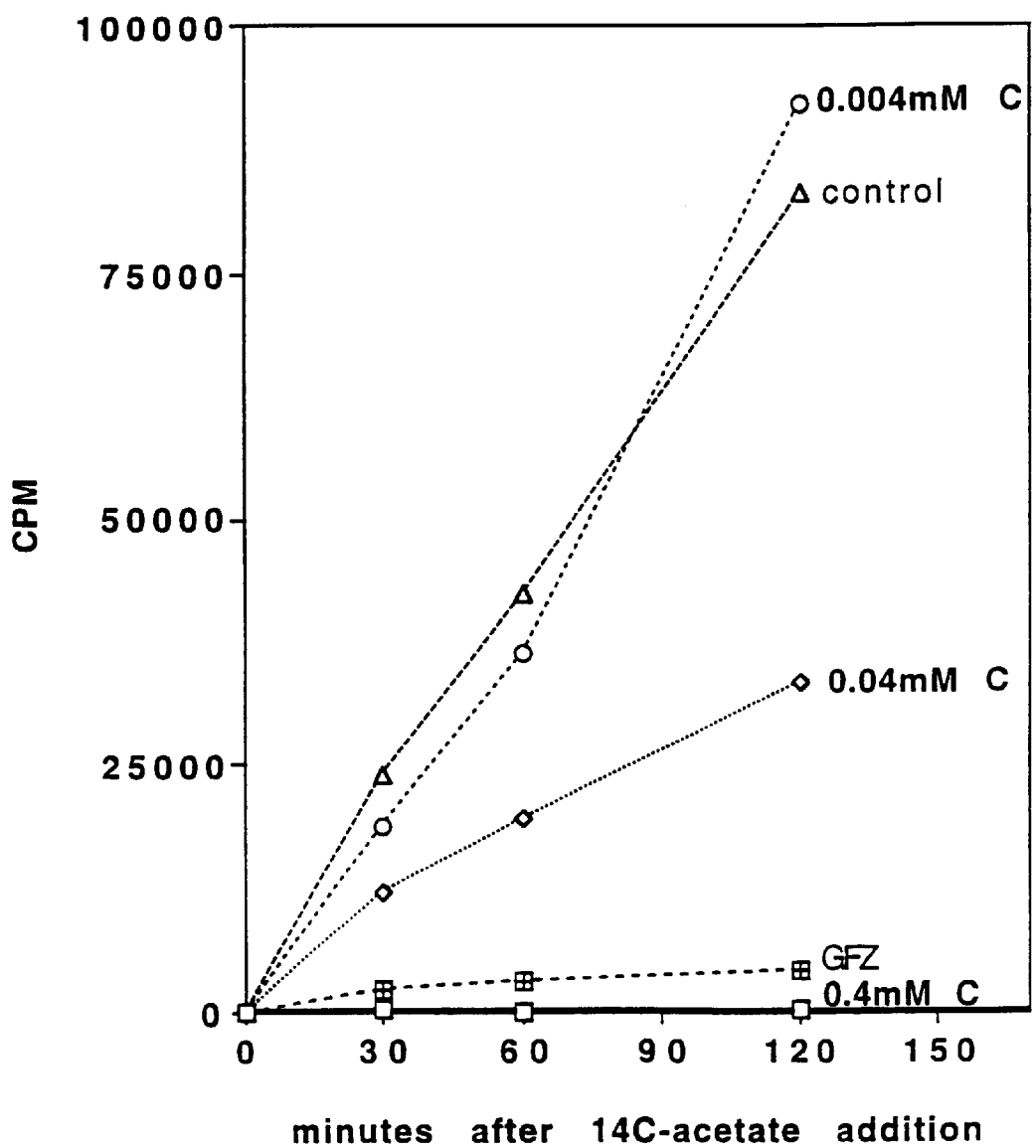
Figure 28B:
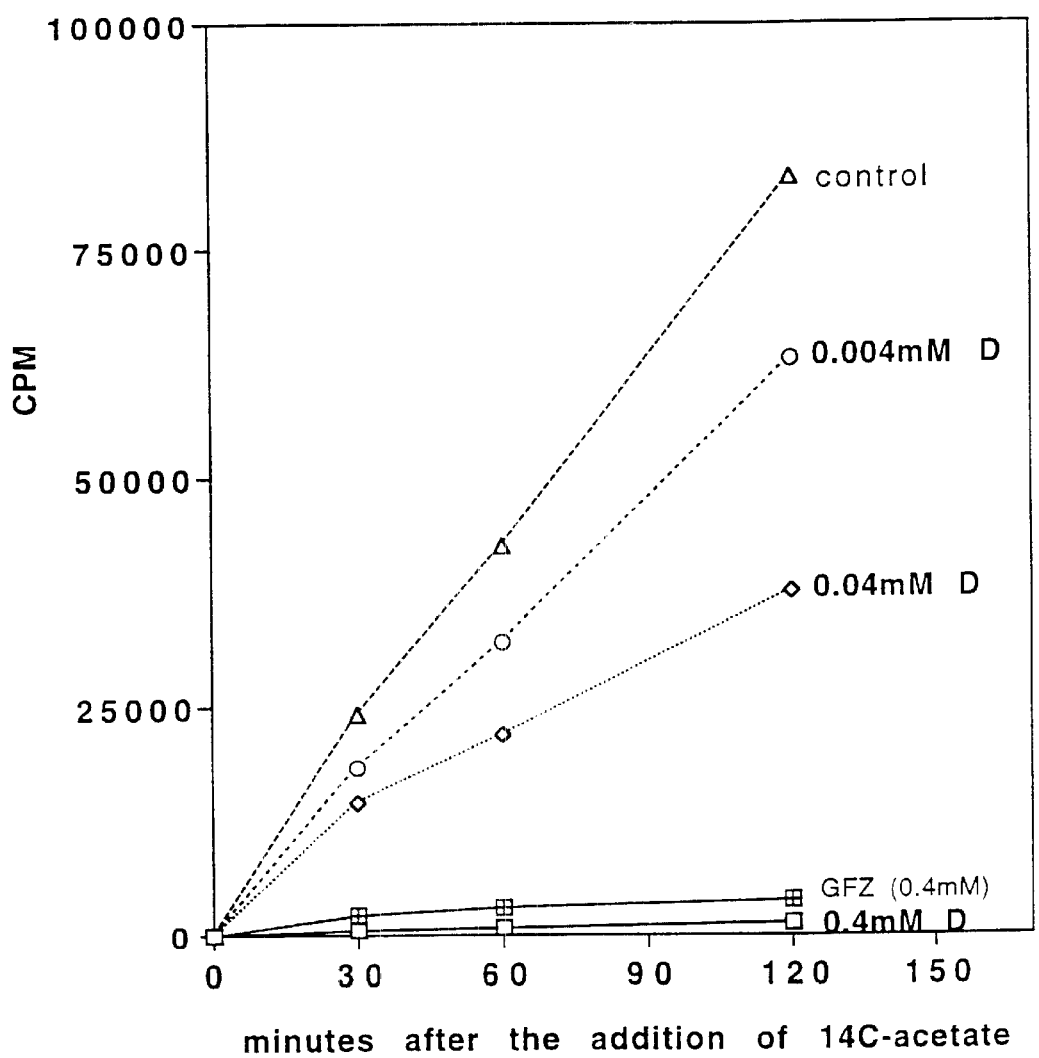
Figure 29:
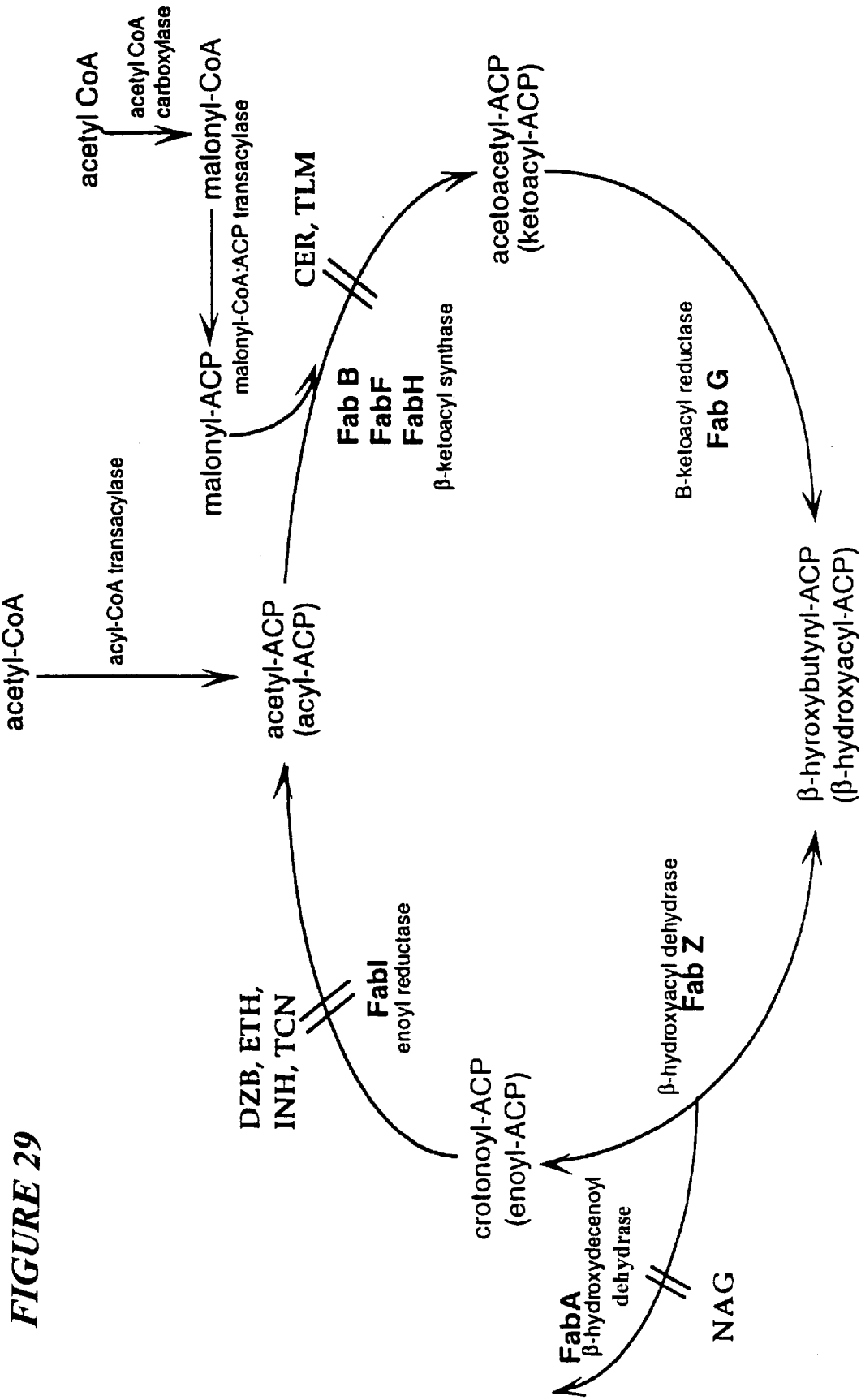
Figure 31:
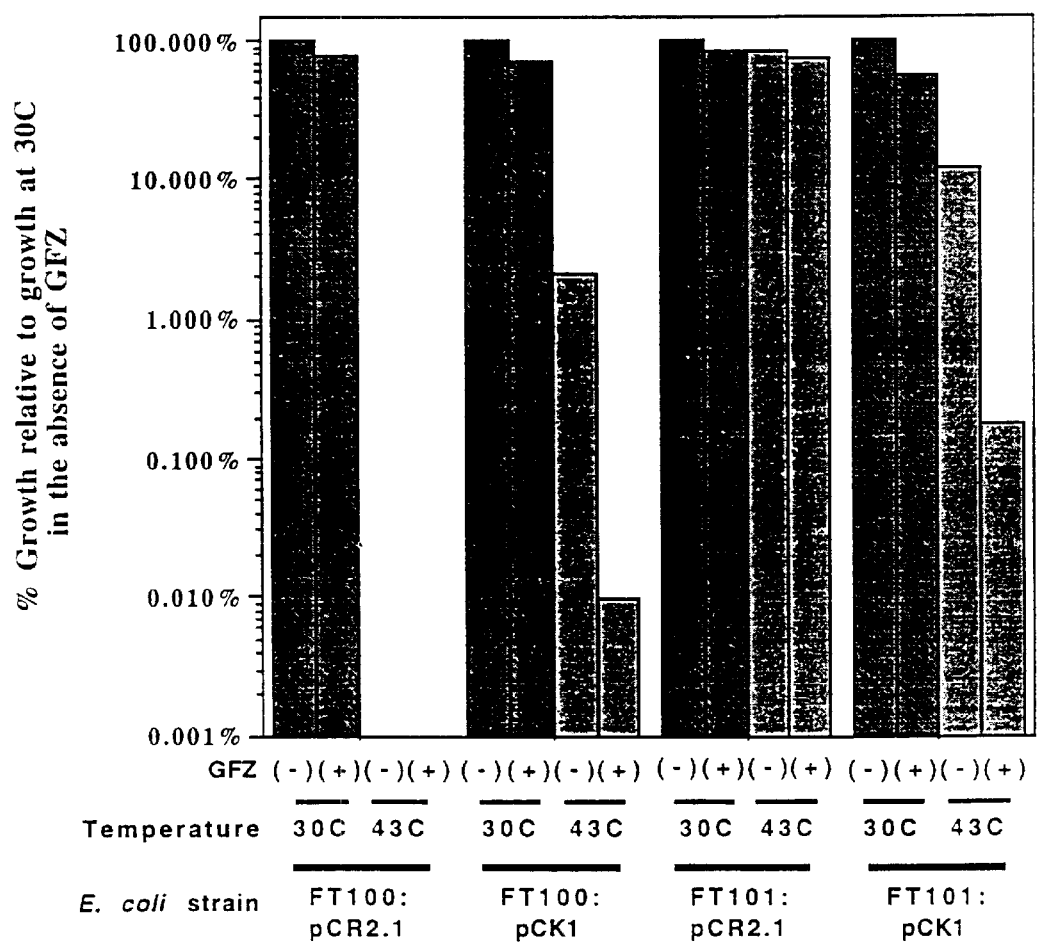
Figure 32:
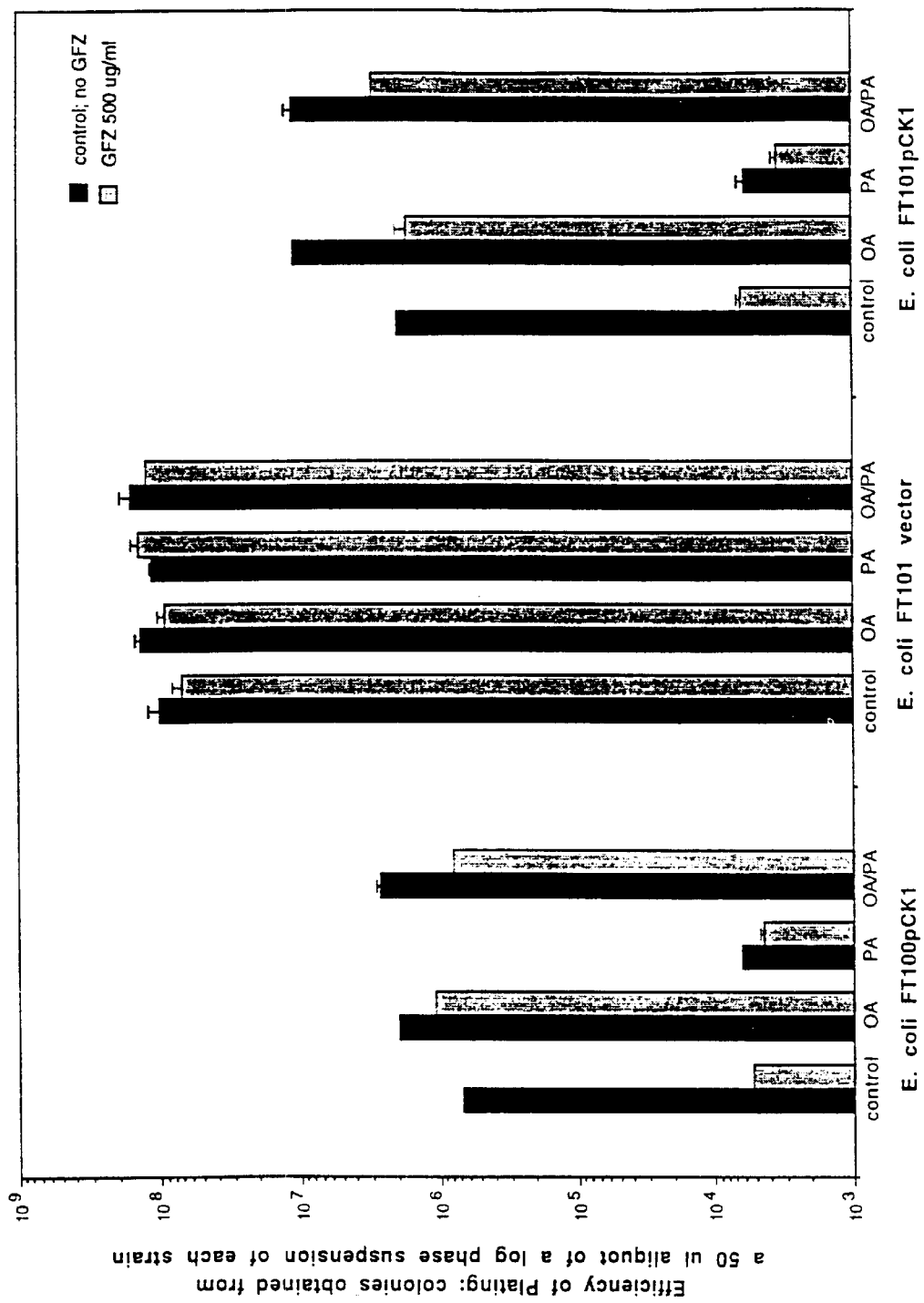
Figure 34:
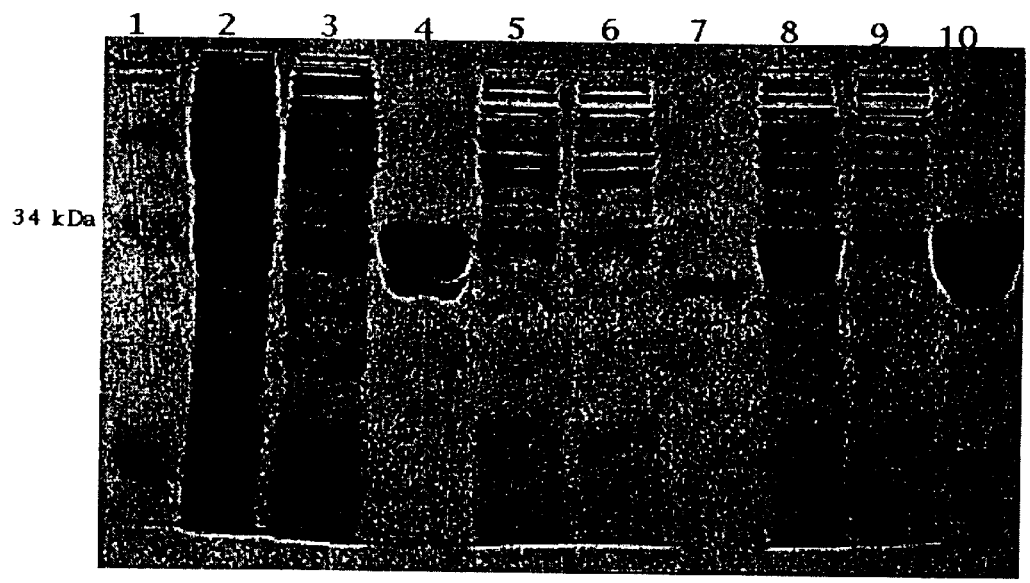
Figure 35:
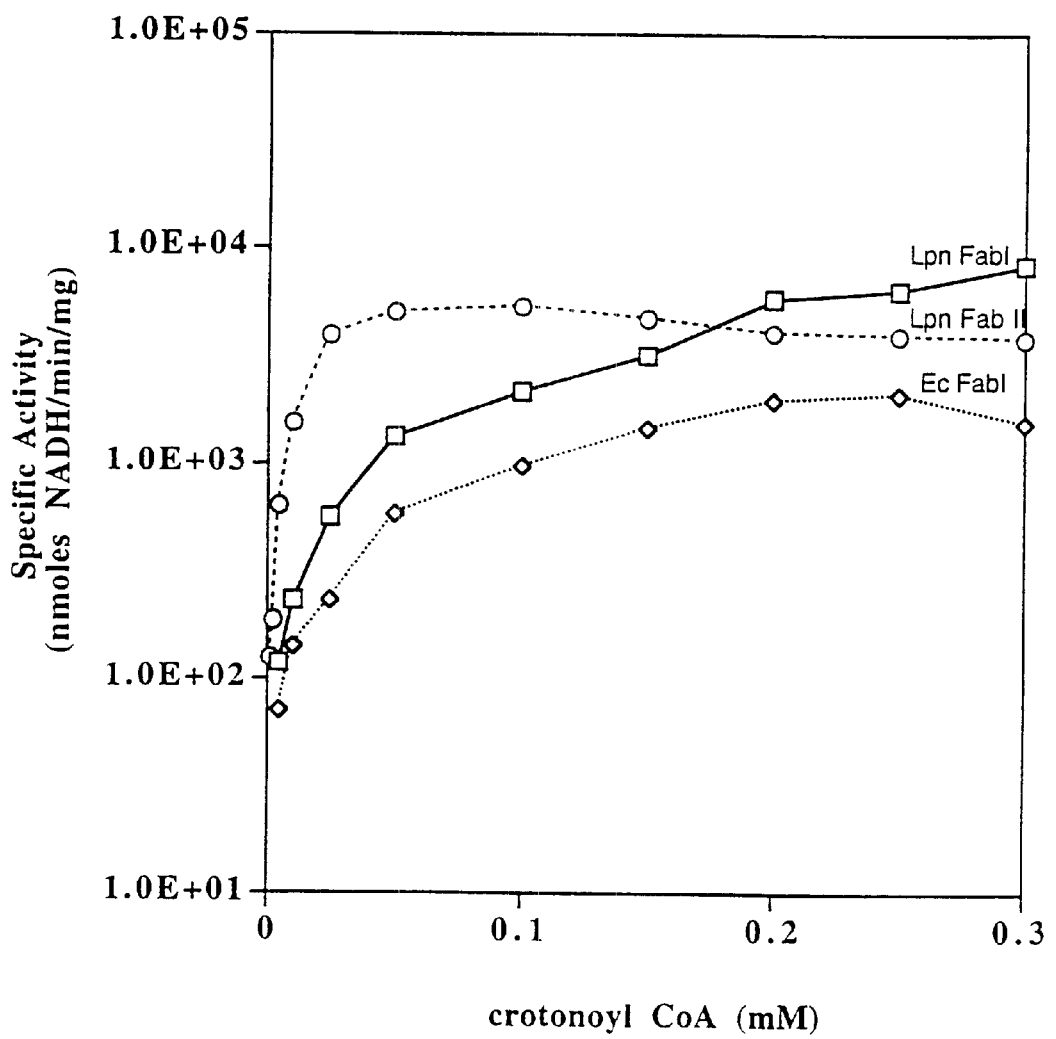
FIG. 35. Comparison of the specific activities of *L. pneumophila* FabT and FabX, and of *E. coli* FabI, for crotonoyl-CoA. His-tagged FabX, FabT, or FabI, was incubated with increasing concentrations of crotonoyl-CoA (CCA) in the presence of excess NADH. The rate of NADH hydrolysis was assessed for each enzyme for each concentration of CCA by measuring the decrease in absorbance over time at $A_{340}$ nm. Specific activities were calculated. The specific activities for FabX and FabT are the average for two experiments (+/−) the SEM. The specific activity for was only measured once.
Figure 37A:
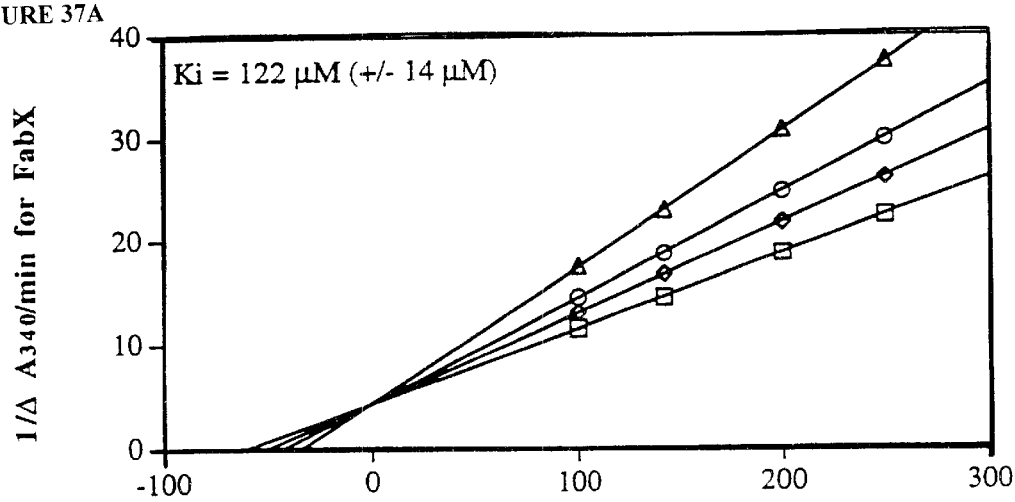
FIGS. 37A–C. GFZ-CoA is a competitive inhibitor of enoyl reductase activity for *L. pneumophila* Fab X and FabT, and *M. tuberculosis* InhA using dodecenoyl-CoA (DCA) as a substrate. Panel a=FabX; panel b=FabT; panel c=InhA. Reaction mixtures containing 100 mM $NaPO_4$ pH 7.4, 100 $\mu$M NADH, and enoyl reductase, were combined with varying concentrations of DCA and GFZ. The ability of GFZ-CoA to inhibit the enoyl reductase activity was assessed by measuring the change in absorbance over time at $A_{340}$ nm as NADH was oxidized to $NAD^+$. Concentrations of GFZ-CoA $\mu$M) utilized are indicated in bold type next to the corresponding plot. Inhibition was competitive with regard to the DCA substrate.
Figure 37B:
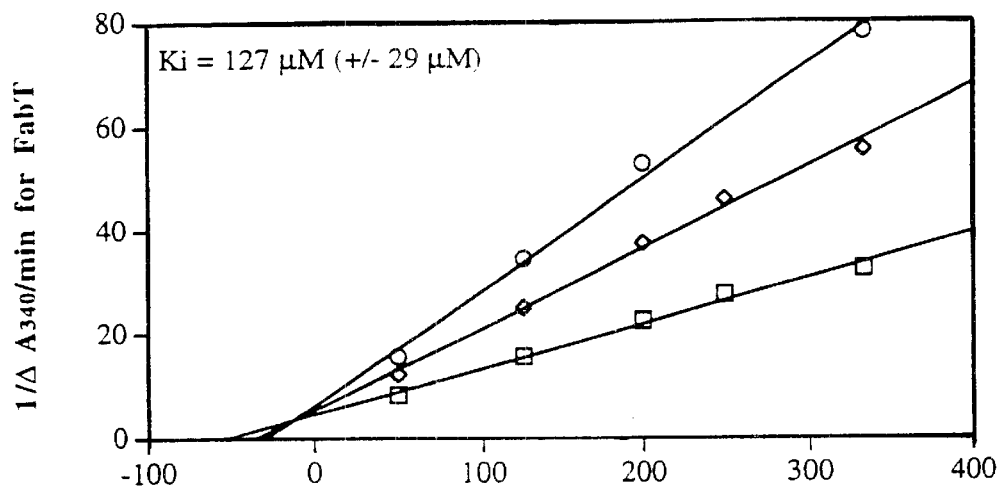
Figure 37C:
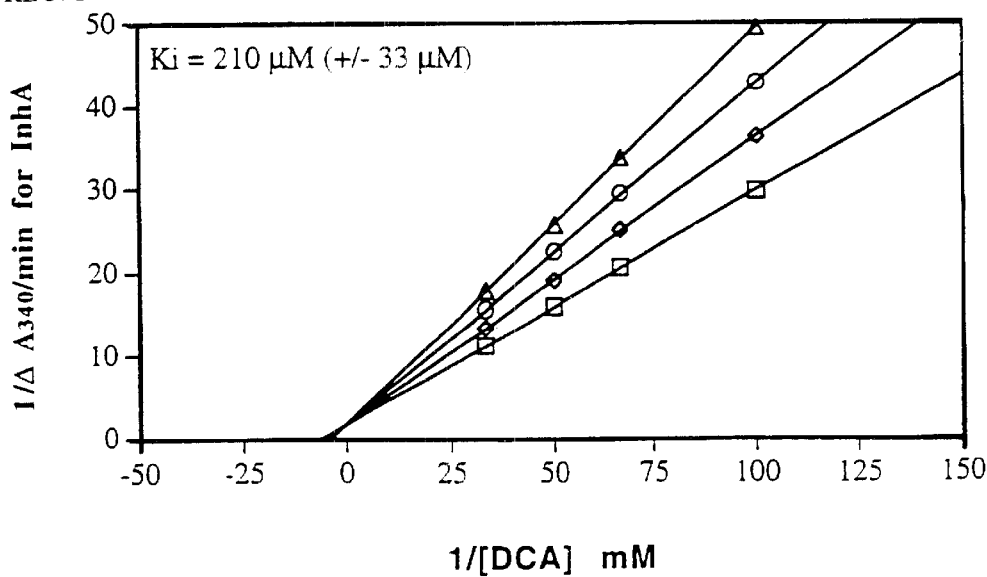
Figure 38:
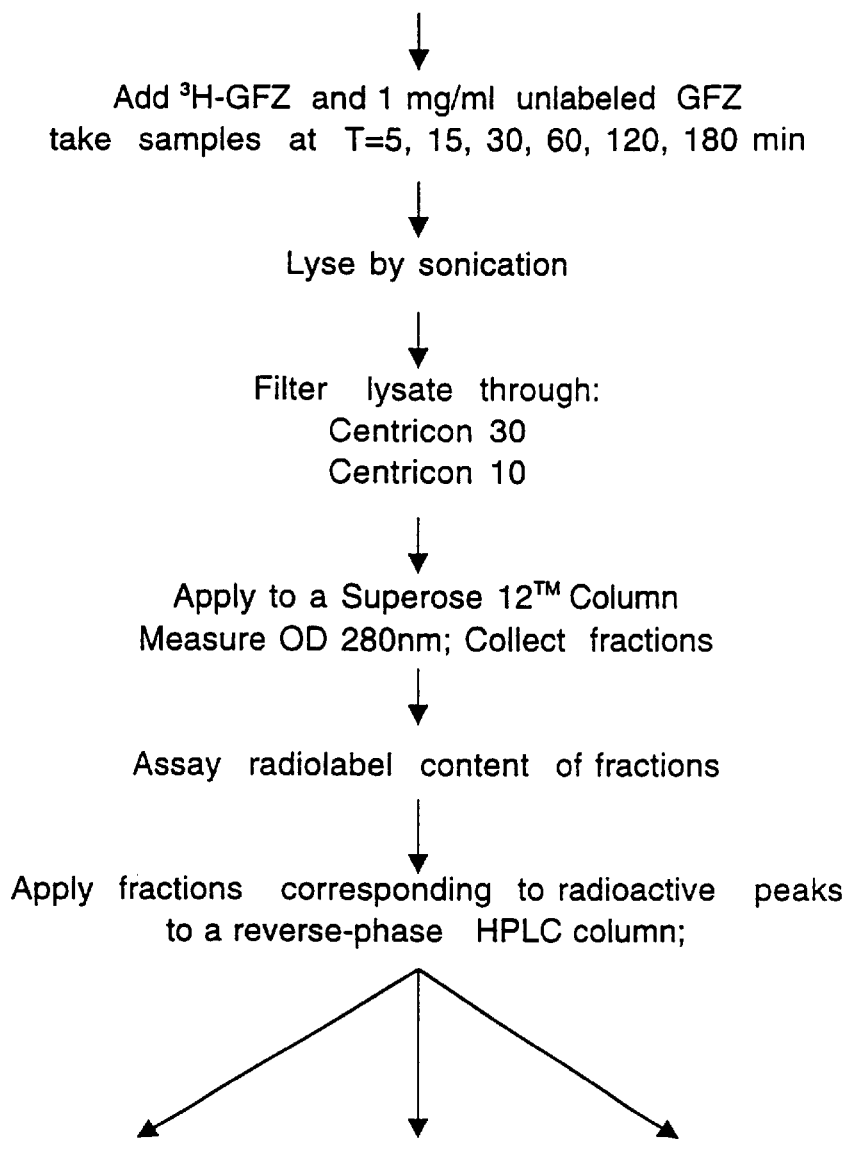
FIG. 38. Flow chart of the methods utilized for the $^3$H-GFZ metabolic labeling studies.
Figure 39:
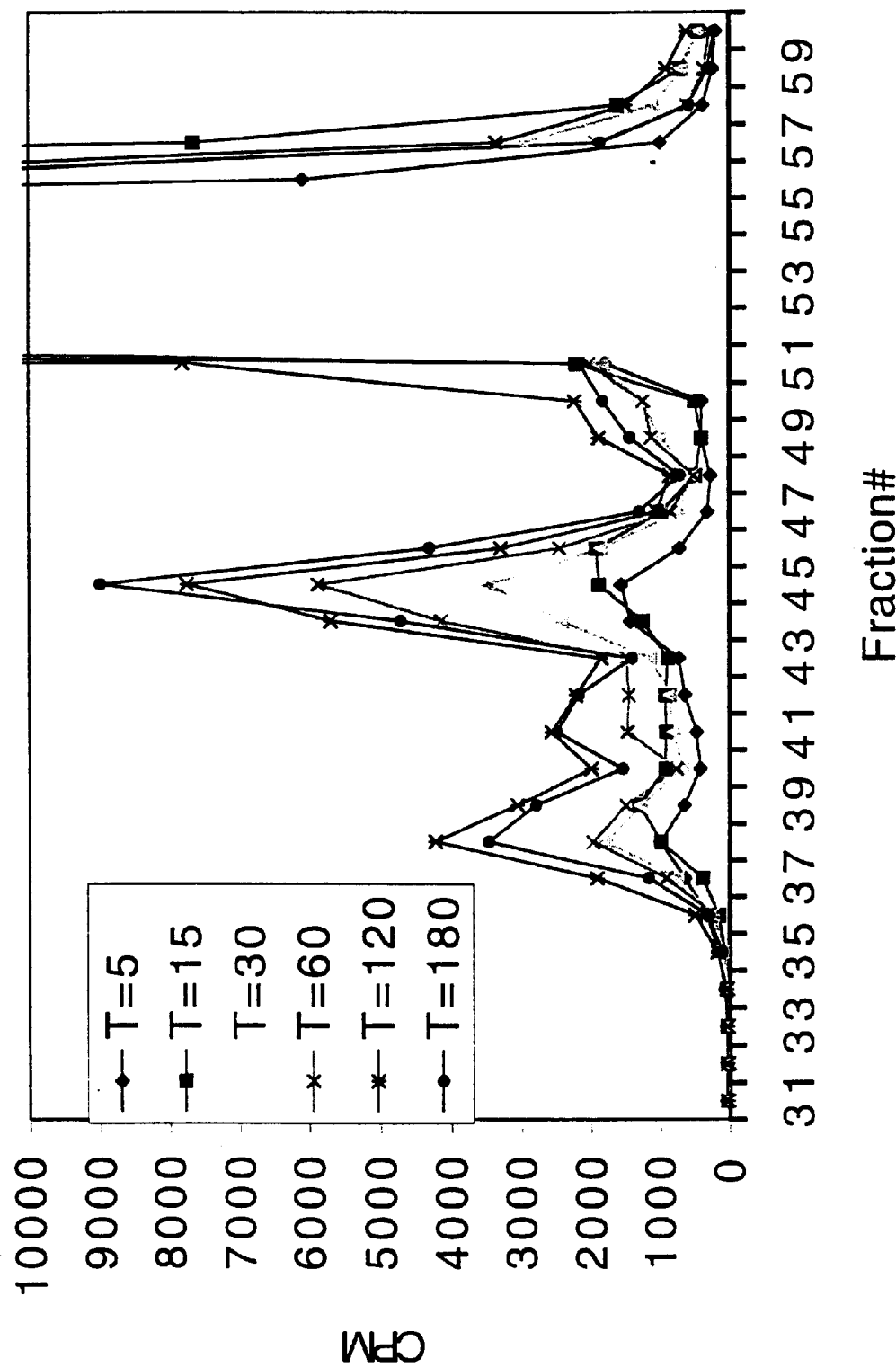
FIG. 39. 280 nm absorbance tracing for the T=120 minute >10 kDA FPLC sample. 500 ml of the <10 kDa filtrate was loaded onto a Superose™ FPLC column and run at 0.5 ml/min with a paper speed of 0.5 mm/min. Each square is 2 $mm^2$.

Structural analogs of GFZ were also tested for inhibition of fatty acid synthesis in whole cells (FIG. 26). *L. pneumophila* cultures were incubated in medium containing $^{14}$C-acetate and each of seven GFZ analogs (FIGS. 27 A–B) (a generous gift from TEVA pharmaceuticals) at a 0.4 mM concentration. Analogs C and D were found to be better inhibitors at 0.4 mM than GFZ at this concentration. Analog B was as effective as GFZ. Dose response experiments were performed for analogs C and D (FIGS. 28A–B). Analogs C and D at a concentration of 0.4 mM, inhibited $^{14}$C-acetate incorporation into *L. pneumophila* by 50%. In contrast, a concentration of 0.1 mM (25 μg/ml) GFZ was required to effect a 50% inhibition of $^{14}$C-acetate incorporation (FIG. 21). Additional commercially available compounds with structural similarity to GFZ (FIG. 26) were examined at concentrations of 0.5 mM. Of those tested, salicyclic acid, clofibric acid, and p-aminosalicyclic acid demonstrated some efficacy, although not as great as that found with GFZ at 0.4 mM (FIG. 28B).

DISCUSSION

The finding that GFZ inhibited $^{14}$C-acetate incorporation into lipids, as measured by TCA precipitation and by chloroform/methanol extraction of *L. pneumophila* cultures and lysates, was consistent with the hypothesis that GFZ inhibited fatty acid synthesis. The dose-response studies demonstrating that $^{14}$C-acetate incorporation is inversely and proportionately related to GFZ concentration, suggested that GFZ had a direct effect on fatty acid synthesis. The argument that GFZ has a direct effect on fatty acid synthesis is supported by the GFZ-mediated inhibition of $^{14}$C-acetate incorporation into lysates.

Cerulenin, an inhibitor of the β-ketoacyl synthase reaction in bacteria and eukaryotes [25,115] with MIC values ranging from 1 to 100 μg/ml }[116], was used as a positive control for the inhibition $^{14}$C-acetate into fatty acids [117]. The inhibitory action of cerulenin on β-ketoacyl synthase is irreversible; 1 mol of cerulenin binds to 1 mol of β-ketoacyl synthase when inhibition approaches 100% [115]. Cerulenin is also a potent inhibitor of the mammalian fatty acid synthetase enzyme (FAS) [25], which contains a β-ketoacyl synthase domain, and for this reason is not useful as an antibiotic in humans. However, it is being pursued as an anticancer drug since certain types of tumors (e.g. ovarian, endometrial, breast, colorectal, and prostate) overexpress FAS [118,119].

Similar to GFZ, cerulenin had an immediate and sustained inhibitory effect on the incorporation of $^{14}$C-acetate into *L. pneumophila* lipids. Cerulenin at 100 μg/ml (0.45 mM) was a slightly better inhibitor of $^{14}$C-acetate incorporation than GFZ at 100 μg/ml, 0.4 mM, in whole *L. pneumophila*. The observation that GFZ is nearly as potent as cerulenin in whole *L. pneumnophila* indicates that it may also have a one to one (drug to target) relationship. The observation that GFZ is not as potent as cerulenin in lysates, indicates that GFZ may need to be metabolized to an active form.

In our studies, GFZ caused a similar dose-dependent decrease in $^{14}$C-acetate incorporation into TCA precipitable material and into chloroform/methanol extractable material. Chloroform/methanol extraction is reported to selectively extract up to 99% of the total lipids from a sample [120,121]. Since bacteria do not synthesize sterols, the majority of the incorporated $^{14}$C-acetate in a chloroform/methanol extract will be found in phospholipids, free fatty acids bound to ACP or CoA, lipid A of the lipoploysaccharaide (LPS), the lipoproteins of the outer membrane, and polyhydroxyalkanoate. Other minor lipid species comprise less than 1% of total bacterial cell lipids. These include ubiquinone [5,24, 122–124] and the lipid containing coenzymes biotin and lipoic acid.

Chloroform/methanol extractions were performed using the method of Bligh and Dyer as this method required smaller volumes of chloroform and methanol, and had been used successfully in *L. pneumophila* and other bacteria [41,125]. Although TCA precipitation is not selective for lipids, it is often utilized to assess $^{14}$C-acetate incorporation into bacterial lipids [40,113,126–128]. Tesh et al [113] examined the incorporation of $^{14}$C-acetate into the TCA soluble and the chloroform/methanol soluble fractions of *L. pneumophila* over a 12–15 hour time period. They demonstrated that 72% of the total radioactivity was recovered in the chloroform/methanol soluble fraction, while 91% was recovered in the TCA precipitate [113].

Acetyl-CoA is utilized by many bacteria as a primer for PHB synthesis. Further, increased pools of acetyl CoA due to inhibition of the TCA cycle in the PHB producing bacteria *Azotobacter vinelandii* and *R. eutropha*, resulted in an increased flux of acetyl-CoA into PHB synthesis [129,130]. If *L. pneumophila* utilizes acetyl-CoA as a precursor for PHB synthesis, then the greater recovery of radiolabel in the TCA precipitable fraction may be due to a greater recovery of PHB in the TCA precipitate.

Due to our use of log phase *L. pneumophila*, which do not accumulate PHB, and the length of our incubations (i.e. 15–60 minutes of $^{14}$C-acetate exposure), it is unlikely that significant amounts of $^{14}$C-acetate were incorporated into PHB. However, a small percentage of the $^{14}$C label recovered in our TCA precipitable fractions, could be at least partially due to the incorporation of $^{14}$C-acetate into PHB. Incorporation of $^{14}$C-acetate into PHB would be expected to increase with time as precursors and intermediates accumulated, and the enzymes responsible for synthesizing PHB were induced. An experiment comparing $^{14}$C-acetate incorporation into PHB, in *L. pneumophila* incubated in the absence and presence of GFZ over a longer time period would address the hypothesis that inhibition of fatty acid synthesis by GFZ shunts fatty acid precursors/intermediates into PHB synthesis.

The lysate experiments were performed to confirm the results obtained from the whole cell experiments in which GFZ inhibited the incorporation of $^{14}$C-acetate into lipids. In addition to confirming these results, the lysate experiments revealed that BZF, a related fibric acid used to treat hypertriglyceridemia, also inhibits lipid synthesis in *L. pneumophila*. Since BZF does not inhibit growth of intact *L. pneumophila*, it is likely that BZF does not penetrate the membrane, or, is a substrate for an efflux transporter in the *L. pneumophila* membrane. Experiments to assess permeability and active transport using radioactive BZF might resolve these issues.

As a first step in determining what aspects of the GFZ molecule are important for the growth inhibitory effects of GFZ, the ability of other structurally similar compounds to inhibit lipid synthesis in whole *L. pneumoiphila* was examined. In general, a free carboxylate moiety linked to a hydrophobic moiety, such as an aliphatic chain, appeared most important. Hydrophobicity is likely to be important for membrane permeability. Substitutions on the aromatic ring that increased the hydrophobicity of TEVA analogs C and D, may have increased the membrane permeability thereby accounting for their increased antibacterial activity against *L. pneumophila*.

The presence of the carboxylate group is likely to be important for the activation of GFZ by *L. pneumophila*. GFZ, like free fatty acids contains a carboxylate group linked to analiphatic chain. Therefore, GFZ, like long chain fatty acids (e.g. $C_{12}$–$C_{18}$ fatty acids), may be converted to its CoA derivative concommitant with transport into bacteria [131–135]. Alternatively, GFZ may be converted to its ACP derivative, similar to short chain fatty acids (e.g. $C_6$–$C_{11}$ fatty acids), and a minor proportion (2%) of long chain fatty acids in *E. coli* [136]. Analog B, which contains an amide instead of a carboxylate, but is still capable of inhibiting fatty acid synthesis, may have a different mechanism of inhibiting fatty acid synthesis. Alternatively, it may be converted to a carboxylate by *L. pneumophila*. Experiments to test this possibility may yield insights into the mechanisms by which TEVA analog B acts to block $^{14}$C-acetate incorporation into lipids in *L. pneumophila*.

In conclusion, GFZ was found to be an inhibitor of lipid synthesis in *L. pneumophila*. This finding was consistent with reports that GFZ and other fibrates inhibit fatty acid elongation in mammalian systems [67,68].

MATERIALS AND METHODS
$^{14}$C-acetate Incorporation into Whole L. pneumophila.

L. pneumophila were grown to log phase (OD=0.6–1.0) in AYE broth at 37° C. 0.5–1.0 ml aliquots were pelleted and resuspended in an equivalent volume of fresh AYE medium. GFZ and other inhibitors were added to the cultures. $^{14}C$-acetate (specific activity 48.9 mCi/mmol) (Sigma) was added immediately thereafter (final concentration 5 μCi/ml) and the cultures were incubated at 37° C. At various time points, 100 μl aliquots of the culture were added to 600 μl 12% TCA on ice; final concentration 10% TCA. TCA precipitates were pipetted onto a Whatman GF/F glass microfibre filter and washed with 30 ml of cold 10% TCA. The filters were dried and radioactivity was assessed by scintillation counting [40,113126,127,139]. Alternatively, at various time points the bacteria were placed on ice, pelleted at 4° C., washed three times with 1 ml of ice cold AYE , and the pellet was extracted with 400 μl of chloroform/methanol (1:1 vol:vol). The extract was washed with 180 ml of water according to the method of Bligh and Dyer [113,120]. 5 μl of the chloroform layer was combined with 5 mls of CytoScint and counted in a scintillation counter. GFZ, salicylate, paraaminosalicylate, isoniazid, clofibrate, 4-hydroxypropionate were obatined from Sigma; 3,4-hydroxypropionate was obtained from Aldrich.

Thin Layer Chromatography.

50 μl of each chloroform/methanol extract was spotted onto EM Science™ Silica Gel 60 F254 plates (Fisher) and developed in chloroform:methanol:acetic acid (65:25:2) until the solvent front was halfway up the plate. The TLC plate was dried, and then developed in chloroform:methanol:sodium acetate pH 3.4 until the solvent from was 1 cm from the top of the plates. The plates were air dried, exposed to iodine vapors to visualize lipid bands. The presence of $^{14}C$-acetate labeled lipids was assessed by exposing the TLC plate to Fuji™ RX film for five days at −80° C.

$^{14}C$-acetate incorporation into Lysates.

One liter of log phase *L. pneumophila*, grown in AYE broth at 37° C., was pelleted, frozen, thawed, resuspended in 5 mls lysis buffer (5 mM Tris HCl pH 7.6, lysozyme 1 mg/ml, EDTA 1 mM, and one Complete™ protease inhibitor tablet) and sonicated at 4° C. The lysate was centrifuged for 10 minutes at 8,000×g at 4° C. to remove intact cells. 50 ul of lysate were combined with 50 ul of a cocktail consisting of 50 mM Tris HCl (pH 7.6), 5 mM $MgCl_2$, 5 mM ATP, 1 mM CoA, 1 mM DTT, 1 mM NADH, 1 mM NADPH, and $^{14}C$-acetate (10 μCi/ml) in 1.5 ml eppendorf tubes on ice. Boiled lysates were prepared by heating a 50 μl aliquot of the lysate for 10 minutes in a boiling water bath prior to the addition of the above cocktail. GFZ, BZE, CER, were added to the lysates to a final concentration of 2 mM. EDTA was added to the lysates to a final concentration of 10 mM. The reaction mixtures were incubated for 10–30 minutes at 37° C. At the times indicated, the 100 μl reaction were placed on ice and precipitated by the addition of 600 μl of ice cold 12% TCA. The precipitates were pelleted in a microfuge at 4° C., and washed 3× with 1 ml of 10% TCA in each wash. The washed TCA precipitated material was extracted with 200 μl of chloroform/methanol (1:1), and the extract was washed with 100 ul of water. The aqueous layer was removed, washed with 100 μl of chloroform/methanol (1:1), and the two organic extracts were combined. The entire organic extract was added to a scintillation tube, evaporated overnight and counted in 5 mls of CytoScint with a scintillation counter.

GFZ INHIBITS AN ENOYL REDUCTASE FROM *LEGIONELLA PNEUMOPHILA*

The finding that *L. pneumophila* accumulated polyhydroxybutyrate (PHB) in response to GFZ led us to hypothesize that GFZ inhibited enzyme(s) involved in fatty acid synthesis/elongation. Support for this hypothesis was obtained by studies of the ability of GFZ to inhibit $^{14}C$-acetate incorporation into *L. pneumophila* lipids. Since GFZ inhibited lipid synthesis in *L. pneumophila*, we reasoned that the most likely target would be a regulatory enzyme in fatty acid synthesis.

Putative targets included the β-ketoacyl synthase, the target of the fatty acid synthesis inhibitors cerulenin [115] and thiolactomycin [28]; b-hydroxydecenoyl dehydrase, the target for the unsaturated fatty acid synthesis inhibitor N-decenoyl-N-acetylcysteamine [33]; and enoyl reductase, the target for diazoborines [140], triclosan [40], and isoniazid [1] (FIG. 29).

Since the FabI enoyl reductase of *E. coli* was reported to be an essential enzyme involved in regulating the rate of fatty acid synthesis, we chose to examine this protein for sensitivity to GFZ. A second reason for the selection of enoyl reductase, was the observation that inhibition of the FabI enoyl reductase in *E. coli* stimulated the accumulation of 3-hydroxybutyryl-ACP (3-HB-ACP) [17]. Under normal conditions, crotonoyl-ACP, the substrate for *E. coli* FabI, is unstable and is present at 1/10 the level of 3-HB-ACP [14]. Therefore, inhibition of FabI in *E. coli* stimulates the accumulation of 3-HB-ACP rather than crotonoyl-ACP. If *L. pneumophila* contains a PhaG homolog capable of converting 3-HB-ACP to 3-HB-CoA, then GFZ-mediated enoyl reductase inhibition might result in the accumulation of a precursor for PHB synthesis.

References

1. Banerjee, A., E. Dubnau, A. Quemard, V. Balasubramanian, K. S. Um, T. Wilson, D. Collins, G. de Lisle and W. R. Jacobs Jr. 1994. inhA, a gene encoding a target for isoniazid and ethionamide in *Mycobacterium tuberculosis*. Science. 263:227–230.
2. Rozwarski, D. A., G. A. Grant, D. H. R. Barton, W. R. Jacobs, Jr. and J. C. Sacchettini. 1998. Modification of the NADH of the isoniazid target (InhA) from *Mycobacterium tuberculosis*. Science. 279:98–102.
3. Quemard, A., J. C. Sacchettini, A. Dessen, C. Vilcheze, R. Bittman, W. R. Jacobs and J. S. Blanchard. 1995. Enzymatic characterization of the target for isoniazid in *Mycobacterium tuberculosis*. Biochemistry. 34:8235–8241.
4. Smith, S. 1994. The animal fatty acid synthase: one gene, one polypeptide, seven enzymes. FASEB J. 8:1248–1259.
5. Cronan, J., J. E. and C. O. Rock. 1996. Biosynthesis of membrane lipids, 612–636. In F. C. Neidhardt (ed), *Escherichia coli* and Salmonella Cellular and Molecular Biology. ASM Press, Washington, D.C.
6. Barker, J., P. A. Lambert and M. R. Brown. 1993. Influence of intra-amoebic and other growth conditions on the surface properties of *Legionella pneumophila*. Infect Immun. 61:3503–10.
7. Moll, H., A. Sonesson, E. Jantzen, R. Marre and U. Zahringer. 1992. Identification of 27-oxo-octacosanoic acid and heptacosane-1,27-dioic acid in *Legionella pneumophila*. FEMS Microbiol. Lett. 97:1–6.
8. Dreher, P. K., K. Poralla and W. A. Kong. 1976. Synthesis of w-alicyclic fatty acids from cyclic precursors in *Bacillus subtilis*. J. Bacteriol. 127:1136–1140.
9. Clark, D. P., D. DeMendoza, M. L. Polacco and J. E. Cronan, Jr. 1983. Beta-hydroxydecanoyl thio ester dehydrase does not catalyze a rate-limiting step in Escherichia coli unsaturated fatty acid synthesis. Biochemistry. 22:5897–902.
10. Garwin, J. L., A. L. Klages and J. Cronan, J. E. 1980. β-ketcacyl-acyl carrier protein synthase II of *Escherichia*

*coli*. Evidence for function in the thermal regulation of fatty acid synthesis. J. Biol. Chem. 255:3263–3265.
11. Jackowski, S. and C. O. Rock. 1983. Ratio of active to inactive forms of acyl carrier protein in *Escherichia coli*. J Biol Chem. 258:15186–91.
12. Oku, H., N. Yagi, J. Nagata and I. Chinen. 1994. Precursor role of branched-chain amino acids in the biosynthesis of iso and anteiso fatty acids in rat skin. Biochim Biophys Acta. 1214:279–87.
13. Kaneda, T. 1991. Iso- and anteiso-fatty acids in bacteria: biosynthesis, function, and taxonomic significance. Microbiol. Rev. 55:288–302.
14. Heath, R. J. and C. O. Rock. 1995. Enoyl-acyl carrier protein reductase (fabI) plays a determinant role in competing cycles of fatty acid elongation in *Escherichia coli*. J. Biol. Chem. 270:26538–26542.
15. Heath, R. J. and C. O. Rock. 1996. Roles of the FabA and FabZ beta-hydroxyacyl-acyl carrier protein dehydratases in *Escherichia coli* fatty acid biosynthesis. J Biol Chem. 271:27795–801.
16. Heath, R. J., S. Jackowski and C. O. Rock. 1994. Guanosine tetraphosphate inhibition of fatty acid and phospholipid synthesis in *Escherichia coli* is relieved by overexpression of glycerol-3-phosphate acyltransferase (plsB). J Biol Chem. 269:26584–90.
17. Heath, R. J. and C. O. Rock. 1996. Regulation of fatty acid elongation and initiation by acyl—acyl carrier protein in Escherichia coli. J Biol Chem. 271:1833–6.
18. Magnuson, K., S. Jackowski, C. O. Rock and J. E. Cronan, Jr. 1993. Regulation of fatty acid biosynthesis in *Escherichia coli*. Microbiol Rev. 57:522–42.
19. Sinesky, M. 1971. Temperature control of phospholipid biosynthesis in *Escherichia coli*. J. Bact. 106:449–455.
20. Cronan, J. E., Jr. 1975. Thermal regulation of the membrane lipid composition of *Escherichia coli*. J. Biol. Chem. 250:7074–7077.
21. Black, P. N., C. C. DiRusso, A. K. Metzger and T. L. Heimert. 1992. Cloning, sequencing, and expression of the fadD gene of *Escherichia coli* encoding acyl coenzyme A synthetase. J Biol Chem. 267:25513–20.
22. DiRusso, C. C., T. L. Heimert and A. K. Metzger. 1992. Characterization of FadR, a global transcriptional regulator of fatty acid metabolism in *Escherichia coli*. Interaction with the fadb promoter is prevented by long chain fatty acyl coenzyme A [published erratum appears in J Biol Chem 1992 Nov 5;267(31):22693]. J Biol Chem. 267:8685–91.
23. DiRusso, C. C., A. K. Metzger and T. L. Heimert. 1993. Regulation of transcription of genes required for fatty acid transport and unsaturated fatty acid biosynthesis in *Escherichia coil* by FadR. Mol Microbiol. 7:311–22.
24. DiRusso, C. C. and T. Nystrom. 1998. The fats of *Escherichia coli* during infancy and old age: regulation by global regulators, alarmones and lipid intermediates. Mol Microbiol. 27:1–8.
25. Vance, D., I. Goldberg, O. Mitsuhashi and K. Bloch. 1972. Inhibition of fatty acid synthetases by the antibiotic cerulenin. Biochem Biophys Res Commun. 48:649–56.
26. Pizer, E. S., F. D. Wood, H. H. S., F. E. Romantsev, G. R. Pasternack and F. P. Kuhajda. 1996. Inhibition of fatty acid synthesis delays disease progression in a xenograft model of ovarian cancer. Cancer Res. 56:1189–1193.
27. Pizer, E. S., C. Jackisch, F. D. Wood, G. R. Pasternack, N. E. Davidson and F. P. Kuhajda. 1996. Inhibition of fatty acid synthesis induces programmed cell death in human breast cancer cells. Cancer Res. 56:2745–2747.
28. Jackowski, S., C. M. Murphy, J. E. Cronan, Jr. and C. O. Rock. 1989. Acetoacetyl-acyl carrier protein synthase. A target for the antibiotic thiolactomycin. J Biol Chem. 264:7624–9.
29. Noto, T., S. Miyakawa, H. Oishi, H. Endo and H. Okazaki. 1982. Thiolactomycin, a new antibiotic. III. In vitro antibacterial activity. J Antibiot (Tokyo). 35:401–10.
30. Lomovskaya, O., K. Lewis and A. Matin. 1995. EmrR is a negative regulator of the *Escherichia coli* multidrug resistance pump EmrAB. J Bacteriol. 177:2328–34.
31. Furukawa, H., J. T. Tsay, S. Jackowski, Y. Takamura and C. O. Rock. 1993. Thiolactomycin resistance in *Escherichia coli* is associated with the multidrug resistance efflux pump encoded by emrAB. J Bacteriol. 175:3723–9.
32. Kass, L. R. 1968. The antibacterial activity of 3-decynoyl-N-acetylcysteamine. J. Biol. Chem. 243:3223–3228.
33. Helmkamp, G. M., Jr., D. J. Brock and K. Bloch. 1968. Beta-hydroxydecanoyl thioester dehydrase. Specificity of substrates and acetylenic inhibitors. J Biol Chem. 243:3229–31.
34. Mandell, G. L. and M. A. Sande. 1990. Drugs used in the chemotherapy of tuberculosis and leprosy, In A. G. Gilman, T. W. Rail, A. S. Nies and P. Taylor (ed), The pharmacalogical basis of therapeutics. Pergamon Press, New York.
35. Dessen, A., A. Quemard, W. R. Blanchard and J. C. Sacchettini. 1995. Crystal structure and function of the isoniazid target of *Mycobacterium tuberculosis*. Science. 267:1638–1641.
36. Miesel, L., T. R. Weisbrod, J. A. Marcinkeviciene, R. Bittman and W. R. Jacobs, Jr. 1998. NADH dehydrogenase defects confer isoniazid resistance and conditional lethality in Mycobacterium smegmatis. J Bacteriol. 180:2459–67.
37. iszhang, Y., T. Garbe and D. Young. 1993. Transformation with katG restores isoniazid-sensitivity in *Mycobacterium tuberculosis* isolates resistant to a range of drug concentrations. Mol Microbiol. 8:521–4.
38. Grassberger, M. A., F. Turnowsky and J. Hildebrandt. 1984. Preparation and antibacterial activities of new 1,2, 3-diazaborine derivatives and analogues. J Med Chem. 27:947–53.
39. Baldock, C., J. B. Rafferty, S. E. Sedelnikova, P. J. Baker, A. R. Stuitje, A. R. Slabas, T. R. Hawkes and D. W. Rice. 1996. A mechanism of drug action revealed by stuctural studies of enoyl reductase. Science. 274:2107–2110.
40. McMurry, L. M., M. Oethinger and S. B. Levy. 1998. Triclosan targets lipid synthesis [letter]. Nature. 394:531–2.
41. Heath, R. J., Y. T. Yu, M. A. Shapiro, E. Olson and C. O. Rock. 1998. Broad spectrum antimicrobial biocides target the FabI component of fatty acid synthesis. J Biol Chem. 273:30316–20.
42. Turnowsky, F., K. Fuchs, C. Jeschek and G. Hogenauer. 1989. envM Genes of *Salmonella typhimurium* and *Escherlchia coli*. J. Bacteriol. 171:6555–6565.
43. Cao, C., S. C. Silverstein, H. C. Neu and T. Steinberg. 1992. J774 Macrophages secrete antibiotics via organic anion transporters. J. Infect. Dis. 165:322–328.
44. Cao, C. X., H. C. Neu and S. C. Silverstein. 1991. Gemfibrozil inhibits organic anion secretion and enhances norfloxacin accumulation in J774 macrophage-like cells. J Cell Biol. 115:476a (Abstr.).
45. Cao, C. X. 1991. Organic anion transporters in white blood cells. Ph.D. thesis. Dept. Physiology. 119.
46. Rudin, D. E., P. X. Gao, C. X. Cao, H. C. Neu and S. C. Silverstein. u1992. Gemfibrozil enhances the Listeriacidal effects of fluoroquinolone antibiotics in J774 macrophages. J. Exp. Med. 176:1439–1447.
47. Stout, J. E. and V. L. Yu. 1997. Legionellosis. New Eng. J. Med. 337:682–687.

48. Horwitz, M. A. 1984. Phagocytosis of the Legionnaires' disease bacterium (*Legionella pneumophila*) occurs by a novel mechanism: engulfment within a pseudopod coil. Cell. 36:27–33.
49. Swanson, M. S. and R. R. Isberg. 1995. Association of *Legionella pneumophila* with the macrophage endoplasmic reticulum. Infect Immun. 63:3609–20.
50. Horwitz, M. A. 1983. Formation of a novel phagosome by the Legionnaires' disease bacterium (*Legionella pneumophila*) in human monocytes. J Exp Med. 158:1319–31.
51. Horwitz, M. A. 1983. The Legionnaires' disease bacterium (*Legionelia pneumophila*) inhibits phagosome-lysosome fusion in human monocytes. J Exp Med. 158:2108–26.
52. Horwitz, M. A. and F. R. Maxfield. 1984. *Legionella pneumophila* inhibits acidification of its phagosome in human monocytes. J Cell Biol. 99:1936–43.
53. Marra, A., M. A. Horwitz and H. A. Shuman. 1990. The HL-60 model for the interaction of human macrophages with the Legionnaires' disease bacterium. J. Immunol. 144:2738–2744.
54. Horwitz, M. A. and S. C. Silverstein. 1980. Legionnaire's disease bacterium (*Legionella pneumophila*) multiplies Intracellularly in human monocytes. J. Clin. Invest. 66:441–450.
55. Muller, A., J. Hacker and B. C. Brand. 1996. Evidence for apoptosis of human macrophage-like HL-60 cells by *Legionelia pneumophila*. Infect. Immun. 64:4900–4906.
56. Peck, R$_{1985}$. A one-plate assay for macrophage bactericidal activity. J Immunol Methods. 82:131–40.
57. Denizot, F. and R. Lang. 1986. Rapid calorimetric assay for cell growth and survival. Modifications to the tetrazolium dye procedure giving improved sensitivity and reliability. J Immunol Methods. 89:271–7.
58. Sadosky, A. B., L. A. Wiater and H. A. Shuman. 1993. Identification of Legionella pneumophila genes required for growth within and killing of human macrophages. Infect. Immun. 61:5361–5373.
59. Jin, F. Y., V. S. Kamanna, M. Y. Chuang, K. Morgan and M. L. Kashyap. 1996. Gemfibrozil stimulates apolipoprotein A-I synthesis and secretion by stabilization of mRNA transcripts in human hepatoblastoma cell line (Hep G2). Arterioscler. Thromb. Vasc. Biol. 16:1052–1062.
60. Hemingway, C. J., K. K. Tey and M. R. Munday. 1995. Short-term inhibition of fatty acid and cholesterol biosynthesis by the lipid-lowering drug gemfibrozil in primary rat hepatocyte cultures and rat liver in vivo. Biochem Soc Trans. 23:496S.
61. Kahri, J., T. Sane, A. van Tol and M. R. Taskinen. 1995. Effect of gemfibrozil on the regulation of HDL subfractlons in hypertriglyceridaemic patients. J Intern Med. 238:429–36.
62. Latruffe, N. and J. Vamecq. 1997. Peroxisome proliferators and peroxisome proliferator activated receptors (PPARs) as regulators of lipid metabolism. Biochimie. 79:81–94.
63. Schoonjans, K., B. Staels and J. Auwerx. 1996. The peroxisome proliferator activated receptors (PPAPS) and their effects on lipid metabolism and adipocyte differentiation. Biochim Biophys Acta. 1302:93–109.
64. Miller, M., P. S. Bachorik, B. W. McCrindle and P. O. Kwiterovich, Jr. 1993. Effect of gemfibrozil in men with primary isolated low high-density lipoprotein cholesterol: a randomized, double-blind, placebo-controlled, crossover study. Am J Med. 94:7–12.
65. Baldo, A., A. D. Sniderman and K. Cianflone. 1994. Increase in intracellular triglyceride synthesis induced by gemfibrozil. Metabolism. 43:257–262.
66. Schoonjans, K., B. Staels, P. Grimaldi and J. Auwerx. 1993. Acyl-CoA synthetase mRNA expression is controlled by fibric acid derivatives, feeding and liver proliferation. Eur. J. Biochem. 216:615–622.
67. Sánchez, R. M., M. Viñals, M. Alegret, M. Vazquez, T. Adzet, M. Merlos and J. C. Laguna. 1992. Inhibition of rat liver microsomal fatty acid chain elongation by gemfibrozil in vitro. FEBS. 300:89–92.
68. Sánchez, R. M., M. Viñals, M. Alegret, M. Vázauez, A. Adzet, M. Merlos and J. C. Laguna. 1993. Fibrates modify rat hepatic fatty acid chain elongation and desaturation in vitro. Biochem. Pharm. 46:1791–1796.
69. Tam, S. P., L. Dory and D. Rubinstein. 1981. Fate of apolipoproteins C-1, C-iii, and E during lipolysis of human very low density lipoproteins in vitro. J Lipid Res. 22:641–51.
70. Havlichek, D., L. Saravolatz and D. Pohold. 1987. Effect of quinolones and other antimicrobial agents on cell-associated *Legionella pneumophila*. Antimicrob. Agents. Chemother. 31:1529–1534.
71. Horwitz, M. A. and S. C. Silverstein. 1983. Intracellular multiplication of Legionnaires' disease bacteria (*Legionella pneumophila*) in human monocytes is reversibly inhibited by erythromycin and rifampin. J Clin Invest. 71:15–26.
72. Barker, J. E. and I. D. Farrell. 1990. The effects of single and combined antibiotics on the growth of *Legionella pneumophila* using time-kill studies. J. Antimicrob. Chemother. 26:45–53.
73. Vilde, J. L., E. Dournon and P. Rajagopalan. 1986. Inhibition of *Legionella pneumophila* multiplication within human macrophages by antimicrobial agents. Antimicrob. Agents Chemother. 30:743–748.
74. Silverstein, S. C. and C. A. Kabbash. 1994. Penetration, retention, intracellular localization, and antimicrobial activity of antibiotics within phagocytes. Current Ooinion in Hematology, Functions and Disorders of Leukocytes, 1993, 1(1):85–92.
75. Feeley, J. C., R. J. Gibson, G. W. Gorman, N. C. Langford, J. K. Rasheed, D. C. Mackel and W. B. Baine. 1979. Charcoal-yeast extract agar: primary isolation medium for *Legionella pneumophila*. J Clin Microbiol. 10:437–41.
76. Liebers, D. M., A. L. Baltech, R. P. Smith, M. C. Hammer and J. V. Conroy. 1989. Susceptibility of *Legionella pneumophila* to eight antimicrobial agents including four macrolides under different assay conditions. J. Antimicrob. Chemother. 23:37–41.
77. Barker, J., H. Scaife and M. R. Brown. 1995. intraphagocytic growth induces an antibiotic-resistant phenotype of *Legionella pneumophila*. Antimicrob. Agents Chemother. 39:2684–2688.
78. FDA Summary Basis of Approval, N.-W. -. L. C., p.1–9. FDA Summary Basis of Approval, NDA 18 422. Warner-Lambert Co., p.1–9.
79. Pharmacologist Review of NDA 1-422, 0. S. S. t. F. b. W.-L. C., Mar. 12, 1981, p1–18. Pharmacologist Review of NDA 1-422, Original Summary. Submitted to FDA by Warner-Lambert Co., Mar. 12, 1981, p1–18.
80. Brown, M. S. and J. L. Goldstein. 1990. Drugs used in the treatment of hyperlipoproteinemias, 874–896. In A. G. Gilman, T. W. Rall, A. S. Nies and P. Taylor (ed), The pharmalogical basis of therapeutics. Pergamon Press, New York.
81. Nakagawa, A., A. Shigeta, H. Iwabuchi, M. Horiguchi, K. Nakamura and H. Takahagi. 1991. Simultaneous determination of gemfibrozil and its metabolites in plasma and 81. urine by a fully automated high performance liquid chromatographic system. Biomed Chromatogr. 5:68–73.
82. Cayen, M. N. 1985. DisDosition, metabolism, and pharmacokinetics of antihyperlipidemic agents in laboratory animals and man. Pharmac. Ther. 29:157–204.
83. Horwitz, M. A. 1983. Symbiotic interactions between *Legionella pneumophila* and human leukocytes. Int Rev Cytol Suppl. 14:307–28.
84. W. H. O. Ed. 1996. The World Health Report.
85. McCray, E., C. M. Weinbaum, C. R. Braden and I. M. Onorato. 1997. The epidemiology of tuberculosis in the United States. Clin Chest Med. 18:99–113.
86. Raviglione, M. C., D. E. Snider, Jr. and A. Kochi. 1995. Global epidemiology of tuberculosis. Morbidity and mortality of a worldwide epidemic [see comments]. Jama. 273:220–6.
87. Antonucci, G., E. Girardi, M. C. Raviglione and G. Ippolito. 1995. Risk factors for tuberculosis in HIV-infected persons. A prospective cohort study. The Gruppo Italiano di Studio Tubercolosi e AIDS (GISTA). Jama. 274:143–8.
88. Markowitz, N., N. I. Hansen, P. C. Hopewell, J. Glassroth, P. A. Kvale, B. T. Mangura, T. C. Wilcosky, J. M. Wallace, M. J. Rosen and L. B. Reichman. 1997. Incidence of tuberculosis in the United States among HIV-infected persons. The Pulmonary Complications of HIV Infection Study Group. Ann Intern Med. 126:123–32.
89. Bifani, P. J., B. B. Plikaytis, V. Kapur, K. Stockbauer, X. Pan, M. L. Lutfey, S. L. Moghazeh, W. Eisner, T. M. Daniel, M. H. Kaplan, J. T. Crawford, J. M. Musser and B. N. Kreiswirth. 1996. Origin and interstate spread of a New York City multidrug-resistant *Mycobacterium tuberculosis* clone family [see comments]. Jama. 275:452–7.
90. Awaya, J., T. Ohno, H. Ohno and S. Omura. 1975. Substitution of cellular fatty acids in yeast cells by the antibiotic cerulenin and exogenous fatty acids. Biochim Biophys Acta. 409:267–73.
91. Greenspan, M. D. and R. C. Mackow. 1977. The effect of cerulenin on sterol biosynthesis in *Saccharomyces cerevisiae*. Lipids. 12:729–40.
92. Hayashi, T., O. Yamamoto, H. Sasaki, H. Okazaki and A. Kawaguchi. 1984. Inhibition of fatty acid synthesis by the antibiotic thiolactomycin. J Antibiot (Tokyo). 37:1456–61.
93. Cole, S. T., R. Brosch, J. Parkhill, T. Garnier, C. Churcher, D. Harris, S. V. Gordon, K. Eiglmeier, S. Gas, C. E. Barry, 3rd, F. Tekaia, K. Badcock, D. Basham, D. Brown, T. Chillingworth, R. Connor, R. Davies, K. Devlin, T. Feltwell, S. Gentles, N. Hamlin, S. Holroyd, T. Hornsby, K. Jagels, B. G. Barrell and et al. 1998. Deciphering the biology of *Mycobacterium tuberculosis* from the complete genome sequence [see comments] [published erratum appears in Nature 1998 Nov 12;396 (6707):190]. Nature. 393:537–44.
94. Chandler, F. W., R. M. Cole, M. D. Hicklin, J. A. Blackmon and B. S. Callaway. 1979. Ultrastructure of the Legionnaire's disease bacterium. Ann. Int. Med. 90:642–647.
95. Rodgers, F. G. and M. R. Davey. 1982. Ultrastructure of the cell envelope layers and surface details of *Legionella pneumophila*. J. Gen. Microbiol. 128:1547–1557.
96. Mauchline, W. S. and K. C. W. 1991. Development of the BIOLOG substrate utilization system for identification of Legionella spp. Appl. Environ. Microbiol. 57:3345–3349.
97. Moffie, B. G. and R. P. Mouton. 1988. Sensitivity and resistance of *Legionella pneumophila* to some antibiotics and combinations of antibiotics. J Antimicrob Chemother. 22:457–62.
98. Ostle, A. G. and J. G. Holt. 1982. Nile Blue: A as a fluorescent stain for poly-β hydroxybutyrate. Appl. Environ. Microbiol. 44:238–241.
99. de Smet, M. J., G. Eggink, B. Witholt, J. Kingma and H. Wynberg. 1983. Characterization of intracellular inclusions formed by *Pseudomonas oleovorans* during growth on octane. J Bacteriol. 154:870–8.
100. Findlay, R. H. and D. C. White. 1983. Polymericβ-hydroxyalkanoates from environmental samples and *Bacillus megaterium*. Appl. Environ. Microbiol. 45:71–78.
101. Riis, W. and W. Mai. 1988. Gas chromatographic determination of poly-8-hydroxybutyric acid in microbial biomass after hydrochloric acid propanolysis. J. Chromatog. 445:285–289.
102. Anderson, A. J. and E. A. Dawes. 1990. Occurrence, metabolism, metabolic rate, and industrial uses of bacterial polyhydroxyalkanoates. Microbiol. Rev. 54:450–472.
103. Madison, L. L. and G. W. Huisman. 1999. Metabolic engineering of poly(3-hydroxyalkanoates): from DNA to plastic. Microbiol Mol Biol Rev. 63:21–53.
104. West, A. A., J. Rogers, J. V. Lee and C. W. Keevil. 1993. Lack of dormancy in *Legionella pneumophila*?, 201–203. In J. M. Barbaree, R. F. Breiman and A. P. Dufour (ed), Legionella: current status and emerging perspectives. American Society for Microbiology, Washington D.C.
105. James, B. W., W. S. Mauchline, P. J. Dennis, C. W. Keevil and R. Wait. 1999. Poly-3-hydroxybutyrate in *Legionella pneumophila*, an energy source for survival in low-nutrient environments. Appl. Environ. Microbiol. 65:822–827.
106. Hrabak, O. 1992. Industrial production of poly-b-hydroxybutyrate. FEMS Microbiol Rev. 103:251–256.
107. Wallace, K. K., S. Lobo, L. Han, H. A. McArthur and K. A. Reynolds. 1997. In vivo and in vitro effects of thiolactomycin on fatty acid biosynthesis in *Streptomyces collinus*. J Bacteriol. 179:3884–91.
108. Kaneda, T. and E. J. Smith. 1980. Relationship of primer specificity of fatty acid de novo synthetase to fatty acid composition in 10 species of bacteria and yeasts. Can J Microbiol. 26:893–8.
109. Doi, Y., A. Tamaki, M. Kunioka and K. Soga. 1988. Production of copolyesters of 3-hydroxybutyrate and 3-hydroxyvalerate by *Alcaligenes eutrophus* from butyric and pentanoic acids. Appl. Microbiol. Biotechnol. 28:330–334.
110. Rehm, B. H. A., N. Kruger and A. Steinbuchel. 1998. A new metabolic link between fatty acid de novo synthesis and polyhydroxyalkanoic acid synthesis. J Biol Chem. 273:24044–24051.
111. Fukui, T., N. Shiomi and Y. Doi. 1998. Expression and characterization of (R)-specific enoyl coenzyme A hydratase involved in polyhydroxyalkanoate biosynthesis by *Aeromonas caviae*. J Bacteriol. 180:667–73.
112. Clark, D. P. and J. E. Cronan, Jr. 1996. Two-carbon compounds and fatty acids as carbon sources, 343–357. In F. C. Neidhardt (ed), *Escherichia coli* and Salmonella Cellular and Molecular Biology. ASM Press, Washington, D.C.
113. Tesh, M. J., S. A. Morse and R. D. Miller. 1983. Intermediary metabolism in *Legionella pneumophila*: utilization of amino acids and other compounds as energy sources. J. Bacteriol. 154:1104–1109.
114. Cronan, J. E., Jr. and S. Subrahmanyam. 1998. FadR, transcriptional co-ordination of metabolic expediency. Mol Microbiol. 29:937–43.
115. D'Agnolo, G., I. S. Rosenfeld, A. J., S. Omura and P. R. Vagelos. 1973. Inhibition of fatty acid synthesis by the antibiotic cerulenin. Specific inactivation of β-ketoacyl-acyl carrier protein synthetase. Biochim. Biophys. Acta. 326:155–166.

116. Omura, S. 1981. Cerulenin. Methods Enzymol. 72:520–32.
117. Nomura, S., T. Horiuchi, S. Omura and T. Hata. 1972. J. Antibiot. 25:365–368.
118. Kuhajda, F. P., K. Jenner, F. D. Wood, R. A. Hennigar, L. B. Jacobs, J. D. Dick and G. R. Pasternack. 1994. Fatty acid synthesis: a potential selective target for antineoplastic therapy. Proc Natl Acad Sci U S A. 91:6379–83.
119. Pizer, E. S., F. D. Wood, G. R. Pasternack and F. P. Kuhajda. 1996. Fatty acid synthase (FAS): a target for cytotoxic antitetabolites in HL60 promyelocytic leukemia cells. Cancer Res. 56:745–51.
120. Bligh, E. G. and W. J. Dyer. 1959. A rapid method of total lipid extraction and purification. Can J Biochem Physiol. 37:911–917.
121. Folch, J., M. Lees and G. H. Stanley. 1957. A simple method for the isolation and purification of total lipides from animal tissues. J. Biol. Chem. 226:497–509.
122. Helander, I. M., B. Lindner, U. Seydel and M. Vaara. 1993. Defective biosynthesis of the lipid A component of temperature-sensitive firA (omsA) mutant of *Escherichia coli*. Eur J Biochem. 212:363–9.
123. Lambert, M. A. and W. Moss. 1989. Cellular fatty acid compositions and isoprenoid quinone contents of 23 Legionella species. J. Clin. Microbiol. 27:465–473.
124. Henry, A., C. M. Allen and P. W. Stacpoole. 1992. Fibric acid derivatives: effects on the synthesis of isoprenoid lipids in cultured human lymphocytes. Biochim. Biophys. Acta. 1127(2): 168–173.
125. Mindich, L. 1972. Control of fatty acid synthesis in bacteria. J Bacteriol. 110:96–102.
126. Letts, V., P. Shaw, L. Shapiro and S. Henry. 1982. Synthesis and utilization of fatty acids by wild-type and fatty acid auxotrophs of *Caulobacter crescentus*. J Bacteriol. 151:1269–78.
127. Harder, M. E., R. C. Ladenson, S. D. Schimmel and D. F. Silbert. 1974. Mutants of *Escherichia coli* with temperature-sensitive malonyl coenzyme A-acyl carrier protein transacylase. J. Biol. Chem. 249:7468–7475.
128. Weiss, E., M. G. Peacock and J. C. Williams. 1980. Glucose and glutamate metabolism of *Legionella pneumophila*. Curr Microbiol. 4:1–6.
129. Manchak, J. and W. J. Page. 1994. Control of polyhydroxyalkanoate synthesis in *Azobacteri vinelandii* strain UWD. Microbiology. 140:953–963.
130. Park, J. S. and Y. H. Lee. 1996. Metabolic characteristics of the isocitrate dehydrogenase leaky mutant of *Alcaligenes eutrophus* and its utilization for poly-β-hydroxybutyrate production. J. Ferment. Bioeng. 81:197–205.
131. Overath, P., G. Pauli and H. U. Schairer. 1969. Fatty acid degradation in *Escherichia coli*. An inducible acyl-CoA synthetase, the mapping of old-mutations, and the isolation of regulatory mutants. Eur J Biochem. 7:559–74.
132. Klein, K., R. Steinberg, B. Fiethen and P. Overath. 1971. Fatty acid degradation in *Escherichia coli*. An inducible system for the uptake of fatty acids and further characterization of old mutants. Eur J Biochem. 19:442–50.
133. Cronan, J. E., Jr. 1997. In vivo evidence that acyl coenzyme A regulates DNA binding by the *Escherichia coli* FadR global transcription factor. J Bacteriol. 179:1819–23.
134. Elovson, J. and P. R. Vagelos. 1968. Acyl carrier protein. X. Acyl carrier protein synthetase. J Biol Chem. 243:3603–11.
135. Rock, C. O. and S. Jackowski. 1982. Regulation of phospholipid synthesis in *Escherichia coli*. Composition of the acyl-acyl carrier protein pool in vivo. J Biol Chem. 257:10759–65.
136. Rock, C. O. and S. Jackowski. 1985. Pathways for the incorporation of exogenous fatty acids into phosphatidylethanolamine in *Escherichia coli*. J Biol Chem. 260:12720–4.
137. Horsmans, Y., J. P. Desager and C. Harvengt. 1993. Effects of gemfibrozil on the activities of plasma lipolytic enzymes in normolipidemic subjects. Clinca Chimica Acta. 218:223–228.
138. Gnasso, A., B. Lehner, W. Haberbosch, O. Leiss, K. von Bergmann and J. Augustin. 1986. Effect of gemfibrozil on lipids, apoproteins, and postheparin lipolytic activities in normolipidemic subjects. Metabolism. 35:387–93.
139. Heath, R. J. and C. O. Rock. 1996. Inhibition of beta-ketoacyl-acyl carrier protein synthase III (FabH) by acyl—acyl carrier protein in *Escherichia coli*. J Biol Chem. 271:10996–1000.
140. Bergler, H., P. Wallner, A. Ebeling, B. Leitinger, S. Fuchsbichler, H. Aschauer, G. Kollenz, G. Högenauer and F. Turnowsky. 1994. Protein EnvM is the NADH-dependent enoyl-ACP reductase (FabI) of *Escherichia coli*. J. Biol. Chem. 269:5493–5496.
141. Bergler, H., S. Fuchsbichler, G. Högenauer and F. Turnowsky. 1996. The enoyl-[acyl-carrier-protein] reductase (FabI) of *Escherichia coli*, which catalyzes a key regulatory step in fatty acid biosynthesis, accepts NADH and NADPH as cofactors and is inhibited by palmitoyl-CoA. Eur. J. Biochem. 242:689–694.
142. Baldock, C., J. B. Rafferty, A. R. Stuitje, A. R. Slabas and D. W. Rice. 1998. The X-ray structure of *Escherichia coli* enoyl reductase with bound NAD+ at 2.1 A resolution. J Mol Biol. 284:1529–46.
143. Gibson, T., D. Higgins and J. Thompson. 1996. ClustalW.
144. Maloy, S. R., C. L. Ginsburgh, R. W. Simons and W. D. Nunn. 1981. Transport of long and medium chain fatty acids by *Escherichia coli* K12. J Biol Chem. 256:3735–42.
145. Ginsburgh, C. L., P. N. Black and W. D. Nunn. 1984. Transport of long chain fatty acids in *Escherichia coli*. Identification of a membrane protein associated with the fadl gene. J Biol Chem. 259:8437–43.
146. Kameda, K. 1986. Partial purification and characterization of fatty acid binding protein(s) in *Escherichia coli* membranes and reconstitution of fatty acid transport system. Biochem Int. 13:343–50.
147. McClain, M. S., M. C. Hurley, J. K. Brieland and E. N. C. 1996. The *Legionella pneumophila* hel locus encodes intracellularly induced homologs of heavy-metal ion transporters of Alcaligenes spp. Infect. Immun. 64:1532–1540.
148. Arroyo, J., M. C. Hurley, M. Wolf, M. S. McClain, B. I. Eisenstein and N. C. Engleberg. 1994. Shuttle mutagenesis of *Legionella pneumophila*: Identification of a gene associated with host cell cytopathocity. Infect. Immun. 62:4075–4080.
149. Goldman, P. and R. P. Vagelos. 1961. J Biol Chem. 236:2620.
150. Fernandes, N. D. and P. E. Kolattukudy. 1998. A newly identified methyl-branched chain fatty acid synthesizing enzyme from *Mycobacterium tuberculosis* var. bovis BCG. J Biol Chem. 273:2823–8.
151. Cornick, N. A., M. Silva and S. L. Gorbach. 1990. In vitro antibacterial activity of bismuth subsalicylate. Rev. Inf. Dis. 12[Suppl 1]:S9–S10.
152. Manhart, M. D. 1990. In vitro antimicrobial activity of bismuth subsalicylate and other bismuth salts. Rev. Inf. Dis. 12[Suppl 1]:S11–S15.
153. Levy, C. W., A. Roujeinikova, S. Sedelnikova, P. J. Baker, A. R. Stuitje, A. R. Slabas, D. W. Rice and J. B. Rafferty. 1999. Molecular basis of triclosan activity [letter]. Nature. 398:383–4.
154. Black, P. N. and C. C. DiRusso. 1994. Molecular and biochemical analyses of fatty acid transport, metabolism, and gene regulation in *Escherichia coli*. Biochim Biophys Acta. 1210:123–45.

155. Cleland, W. W. 1979. Statistical analysis of enzyme kinetic data. Methods Enzymol. 63:103–38.
156. Martinez-Blanco, H., A. Reglero, L. B. Rodriguez-Aparicio and J. M. Luengo. 1990. Purification and biochemical characterization of phenylacetyl-CoA ligase from *Pseudomonas putida*. A specific enzyme for the catabolism of phenylacetic acid. J Biol Chem. 265:7084–90.

---

What is claimed is:

1. A method of selecting a compound which inhibits the enzymatic activity of enoyl reductase which comprises:

(A) contacting enoyl reductase with the compound;

(B) measuring the enzymatic activity of the enoyl reductase of step (A) compared with the enzymatic activity of enoyl reductase in the absence of the compound, and selecting the compound which inhibits the enzymatic activity of enoyl reductase, wherein the compound has the structure:

or a pharmaceutically acceptable salt or ester thereof, wherein (i) each of $R_1$, $R_2$, $R_3$, $R_4$, $R_5$ and $R_6$ is independently selected from the group consisting of —H, —F, —Cl, —Br, —I, —OH, —$OR_7$, —CN, —$COR_7$, —$SR_7$, —$N(R_7)_2$, —$NR_7$—$COR_8$, —$NO_2$, —$(CH_2)_p$—$OR_7$, —$COSR_7$, —C(=O)—OH, —$CONH_2$, —$NH_2$, a straight chain or branched, substituted or unsubstituted $C_1$–$C_{10}$ alkyl, $C_2$–$C_{10}$ alkenyl, $C_2$–$C_{10}$ alkynyl, $C_3$–$C_{10}$ cycloalkyl, $C_3$–$C_{10}$ cycloalkenyl, thioalkyl, methylene thioalkyl, acyl, phenyl, substituted phenyl and heteroaryl;

(ii) the compound is in the form of an acyl carrier protein metabolite;

(iii) L is —N—, —S—, —O—, —C≡C— or —$CH_2$—;

(iv) $R_7$ is independently selected from the group consisting of —H, —F, —Cl, —Br, —I, —OH, —CN, —COH, —SH, —$NH_2$, —NHCOH, —$(CH_2)_p$OH, a straight chain or branched, substituted or unsubstituted $C_1$–$C_{10}$ alkyl, $C_2$–$C_{10}$ alkenyl, $C_2$–$C_{10}$ alkynyl, $C_3$–$C_{10}$ cycloalkyl, $C_3$–$C_{10}$ cycloalkenyl, thioalkyl, methylene thioalkyl, acyl, phenyl, substituted phenyl and heteroaryl;

(v) A is selected from the group consisting of —$N_2$—, —NH—, —CH=C=CH—, —C≡C—CH(OH)—, —C≡C—$CH_2$—, —$CH_2$—$CH_2$—O—, —$CH_2$—$CH_2$—$CH_2$—O—, —S—, —S(=O)$_2$—, —C(=O)—, —C(=O)—O—, —NH—C(=O)— and —C(=O)—NH—;

(vi) Q is independently an integer from 1 to 10, and if Q is 1, A may be a ($C_1$–$C_{10}$)-alkyl chain, ($C_1$–$C_{10}$)-alkenyl chain or ($C_1$–$C_{10}$)-alkynyl chain which is branched or unbranched, substituted or unsubstituted and is optionally interrupted 1 to 3 times by —O— or —S— or —N—; and (vii) X is —C(=O)O—, —CH=CH—, phenyl, substituted phenyl, heteroaryl, —O-phenyl($CH_3$)$_2$—, —C($CH_3$)$_2$—C(=O)—NH— or —C($CH_3$)$_2$—C(=O)—O—.

2. The method of claim 1, wherein the compound contacts enoyl reductase at the site at which gemfibrozil contacts enoyl reductase.

3. The method of claim 1, wherein the compound is

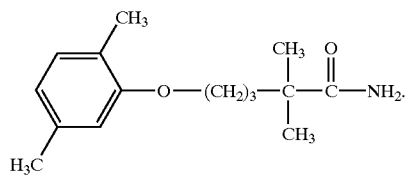

4. The method of claim 1, wherein the compound is

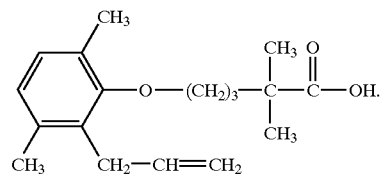

5. The method of claim 1, wherein the compound is

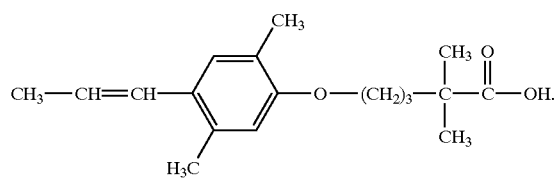

6. The method of claim 1, wherein the compound is

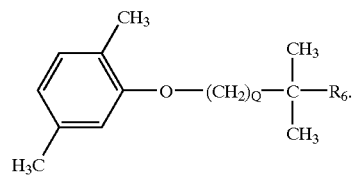

7. A method of selecting a compound which inhibits the enzymatic activity of enoyl reductase which comprises:

(A) contacting enoyl reductase with the compound;

(B) measuring the enzymatic activity of the enoyl reductase of step (A) compared with the enzymatic activity of enoyl reductase in the absence of the compound, and selecting the compound which inhibits the enzymatic activity of enoyl reductase, wherein the compound has the structure:

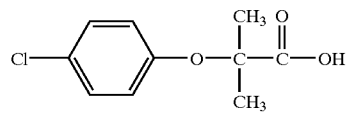

in the form of an acyl carrier protein metabolite.

* * * * *

UNITED STATES PATENT AND TRADEMARK OFFICE
CERTIFICATE OF CORRECTION

PATENT NO. : 6,531,291 B1
DATED : March 11, 2003
INVENTOR(S) : Christina Kabbash et al.

It is certified that error appears in the above-identified patent and that said Letters Patent is hereby corrected as shown below:

Column 2,
Lines 12 and 13, should read -- Q is 1, A may be a $(C_1-C_{10})$ -alkyl chain, $(C_2-C_{10})$ -alkenyl chain or $(C_2-C_{10})$ -alkynyl chain which is --

Column 11,
Lines 24 and 25, should read -- Q is 1, A may be a $(C_1-C_{10})$ -alkyl chain, $(C_2-C_{10})$ -alkenyl chain or $(C_2-C_{10})$ -alkynyl chain which is --
Lines 36 and 37, should read -- of $(C_1-C_{10})$ -alkylene chain, $(C_1-C_{10})$ -alkyl chain, $(C_2-C_{10})$ -alkenyl chain or $(C_2-C_{10})$ -alkynyl chain which is --

Column 13,
Lines 8 and 9, should read -- Q is 1, A may be a $(C_1-C_{10})$ -alkyl chain, $(C_2-C_{10})$ -alkenyl chain or $(C_2-C_{10})$ -alkynyl chain which is --
Line 21, should read -- $(C_2-C_{10})$ -alkenyl chain or $(C_2-C_{10})$ -alkynyl chain which is --

Column 14,
Lines 8 and 9, should read -- Q is 1, A may be a $(C_1-C_{10})$ -alkyl chain, $(C_2-C_{10})$ -alkenyl chain or $(C_2-C_{10})$ -alkynyl chain which is --

Column 15,
Lines 13 and 14, should read -- Q is 1, A may be a $(C_1-C_{10})$ -alkyl chain, $(C_2-C_{10})$ -alkenyl chain or $(C_2-C_{10})$ -alkynyl chain which is --

Column 61,
Lines 32 and 33, should read -- is 1, A may be a $(C_1-C_{10})$ -alkyl chain, $(C_2-C_{10})$ -alkenyl chain or $(C_2-C_{10})$ -alkynyl chain which is --

Signed and Sealed this

Twenty-third Day of September, 2003

JAMES E. ROGAN
*Director of the United States Patent and Trademark Office*